(12) United States Patent
Lackey et al.

(10) Patent No.: US 6,498,176 B1
(45) Date of Patent: Dec. 24, 2002

(54) 3-(ANILINOMETHYLENE) OXINDOLES AS PROTEIN TYROSINE KINASE AND PROTEIN SERINE/THREONINE KINASE INHIBITORS

(75) Inventors: Karen Elizabeth Lackey, Durham, NC (US); Robert Walton McNutt, Jr., Durham, NC (US)

(73) Assignee: SmithKlineBeecham Corporation, Philadelphia, PA (US)

( * ) Notice: Subject to any disclaimer, the term of this patent is extended or adjusted under 35 U.S.C. 154(b) by 0 days.

(21) Appl. No.: 09/914,063

(22) PCT Filed: Feb. 28, 2000

(86) PCT No.: PCT/US00/05057

§ 371 (c)(1),
(2), (4) Date: Aug. 22, 2001

(87) PCT Pub. No.: WO00/56710

PCT Pub. Date: Sep. 28, 2000

(30) Foreign Application Priority Data

Mar. 4, 1999 (GB) .............................................. 9904933

(51) Int. Cl.$^7$ ..................... A61K 31/426; C07D 513/02
(52) U.S. Cl. ..................... 514/366; 548/151; 548/236; 548/259; 548/302.1; 548/483; 546/84; 546/268.4; 514/292; 514/338; 514/374; 514/384; 514/418

(58) Field of Search ................................. 514/384, 374, 514/386, 338, 418, 292; 548/259, 236, 151, 483, 302.1; 546/268.4, 84

(56) References Cited

PUBLICATIONS

RN 130020–27–8 and RN 130020–28–9.*

* cited by examiner

Primary Examiner—Charanjit S. Aulakh
(74) Attorney, Agent, or Firm—John L. Lemanowicz

(57) ABSTRACT

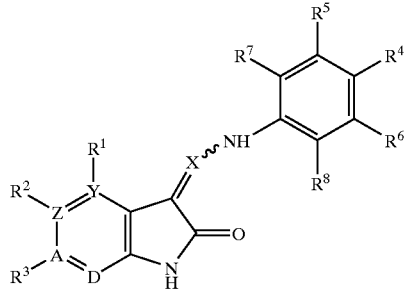

Compounds of formula (I) wherein R1, R2, R3, R4, R5, R6, R7, R8, A, D, X, Y and Z have the meaning as defined in the claims exhibit protein tyrosine kinase and protein serin/threonine kinase inhibitory activity.

17 Claims, No Drawings

3-(ANILINOMETHYLENE) OXINDOLES AS PROTEIN TYROSINE KINASE AND PROTEIN SERINE/THREONINE KINASE INHIBITORS

This application is filed pursuant to 35 U.S.C. §371 as a U.S. National Phase Application of International Application No. PCT/US00/05057 filed Feb. 28, 2000 now WO 06/56710 Sep. 28, 2000, which claims priority from 9904933.0 filed Mar. 4, 1999.

The present invention relates generally to novel amine substituted oxindole compounds and compositions having utility as pharmacological agents in treating diseases or conditions alleviated by the inhibition or antagonism of protein kinase activated signalling pathways in general, and in particular in the pathological processes which involve aberrant cellular proliferation, such as tumor growth, restenosis, atherosclerosis, and thrombosis and methods for using and manufacturing such compounds. In particular, the present invention relates to a series of substituted oxindole compounds, which exhibit protein tyrosine kinase and protein serine/threonine kinase inhibition, and which are useful in inhibiting tumor growth via inhibition of tumor-related angiogenesis.

BACKGROUND OF THE INVENTION

Protein kinases play a critical role in the control of cell growth and differentiation and are key mediators of cellular signals leading to the production of growth factors and cytokines. See, for example, Schlessinger and Ullrich, *Neuron* 1992, 9, 383. A partial non-limiting list of such kinases includes abl, ARaf, ATK, ATM, bcr-abl, Blk, BRaf, Brk, Btk, CDK1, CDK2, CDK3, CDK4, CDK5, CDK6, CDK7, CDK8, CDK9, cfms, c-fms, c-kit, c-met, cRaf1, CSF1R, CSK, c-src, EGFR, ErbB2, ErbB3, ErbB4, ERK, ERK1, ERK2, Fak, fes, FGFR1, FGFR2, FGFR3, FGFR4, FGFR5, Fgr, FLK-4, Fps, Frk, Fyn, GSK, gsk3a, gsk3b, Hck, IGF-1R, IKK, IKK1, IKK2, IKK3, INS-R, Integrin-linkedkinase, Jak, JAK1, JAK2, JAK3, JNK, JNK, Lck, Lyn, MEK, MEK1, MEK2, p38, PDGFR, PIK, PKB1, PKB2, PKB3, PKC, PKCα, PKCβ, PKCδ, PKCε, PKCγ, PKCλ, PKCμ, PKCζ, PLK1, Polo-like kinase, PYK2, tie1, tie2, TrkA, TrkB, TrkC, UL13, UL97, VEGF-R1, VEGF-R2, Yes and Zap70. Protein kinases have been implicated as targets in central nervous system disorders such as Alzheimer's (Mandelkow, E. M. et al. *FEBS Lett.* 1992, 314, 315. Sengupta, A. et al. *Mol. Cell. Biochem.* 1997, 167,99), pain sensation (Yashpal, K. *J. Neurosci.* 1995, 15, 3263-72), inflammatory disorders such as arthritis (Badger, *J. Pharm. Exp. Ther.* 1996, 279, 1453), psoriasis (Dvir, et al, *J. Cell Biol.* 1991, 113, 857), and chronic obstructive pulmononary disease, bone diseases such as osteoporosis (Tanaka et al, *Nature*, 1996, 383, 528), cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al *Cancer Res.* 1996, 56, 3540; Jackson et al *J. Pharm. Exp. Ther.* 1998, 284, 687), restenosis (Buchdunger et al, *Proc, Nat Acad. Sci USA* 1991, 92, 2258), autoimmune diseases and transplant rejection (Bolen and Brugge, *Ann. Rev. Immunol.* 1997, 15, 371) and infectious diseases such as viral (Littler, E. *Nature* 1992, 358, 160), and fungal infections (Lum, R. T. PCT Int. Appl., WO 9805335 A1 980212).

The VEGF-R2 kinase is a receptor tyrosine kinase found in endothelial cells and is involved in angiogenesis—the growth and proliferation of blood vessels from existing capillaries. Angiogenesis plays an important role in development, homeostasis, wound healing, the female reproductive cycle, and in pathological conditions such as rheumatoid arthritis, diabetic retinopathy, macular degeneration, psoriasis and cancer. VEGF-R2 kinase transmits the signal initiated by binding of Vascular Endothelial Growth Factor (VEGF) to the extracellular receptor. Signal transmission to the cell interior is accomplished via tyrosine phosphorylation by VEGF-R2, which prompts proliferation of endothelial cells and the release of cytokines and other cellular processes that result in the growth of new blood vessels. Angiogenesis is critical to the growth of cancerous tumors. Solid tumors will not grow beyond 1–2 mm in size without the support of additional vascularization. Most tumor types, if not all, secrete VEGF in order to stimulate angiogenesis. Inhibition of VEGF-R2 kinase would therefore interrupt a critical process involved in tumor growth and metastasis as well as other pathologic angiogenic conditions.

SUMMARY OF THE INVENTION

In brief summary, the invention comprises compounds of the formula (I):

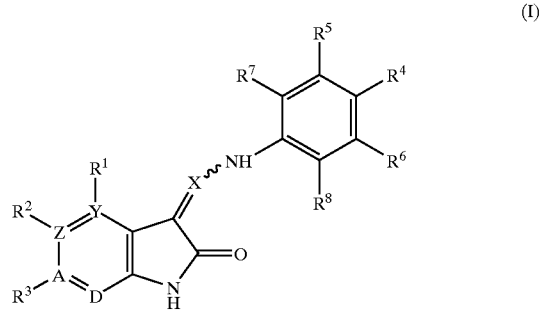

wherein

Y, Z, A, and D are independently selected from the group consisting of: carbon and nitrogen, with the provisos that: (1) Z and D may be nitrogen, but otherwise no more than one of Y, Z, A, and D may be nitrogen, and (2) when Y, Z, or A are nitrogen, substituent $R^1$, $R^2$, or $R^3$ designated for the respective nitrogen atom is non-existent;

X is selected from the group consisting of: N, CH, $CCF_3$, and $C(C_{1-12}$ aliphatic);

$R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, fluoro, bromo, iodo, cyano, sulfonamide, or nitro, where $R^9$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^9$-Aryl-oxycarbonyl, $R^9$-oxycarbonyl-Aryl, Het, aminocarbonyl, $C_{1-12}$ aliphatic-aminocarbonyl, Aryl-$C_{1-12}$ aliphatic-aminocarbonyl, $R^9$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, $C_{1-12}$ aliphatic-sulfonyl, aminosulfonyl, and $C_{1-12}$ aliphatic-aminosulfonyl, where $R^9$, Aryl and Het are as defined below, with the proviso that where X is nitrogen, $R^2$ is not chloro or 3,6-dihydro-6-methyl-2-oxo-2H-1,3,4-thiadiazin-5-yl;

$R^1$ and $R^2$ are optionally joined to form a fused ring selected from the group as defined for Het below, and said fused ring is optionally substituted by a substituent selected from the group consisting of: $C_{1-12}$ aliphatic, halogen, nitro, cyano, $C_{1-12}$ alkoxy, amino, hydroxyl, $(R^{10},R^{11})$-amino, and oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below, with the proviso that where X is nitrogen $R^3$ is not fluoro;

$R^2$ and $R^3$ are optionally joined to form a fused ring selected from the group as defined for Het below, and said fused ring is optionally substituted by $C_{1-6}$ aliphatic or $C_{1-6}$ aliphatic-carbonyl;

with the proviso that $R^1$, $R^2$, and $R^3$ cannot simultaneously be hydrogen;

$R^4$, $R^5$ and $R^6$ may be the same or different and are independently selected from the group consisting of: hydrogen, $C_{1-12}$ aliphatic, thiol, $C_{1-6}$aliphatic-thio, di(trifluoromethyl)hydroxymethyl, carboxamide, mono-$C_{1-12}$aliphatic aminocarbonyl, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, $(R^{10},R^{11})$-amino-$C_{1-12}$ aliphatic aminocarbonyl, $(R^{10},R^{11})$-amino-$C_{1-12}$ aliphatic alkoxycarbonyl, $(R^{10},R^{11})$-amino-$C_{1-12}$ aliphatic aminocarbonylamino, $(R^{10},R^{11})$-amino-$C_{1-6}$ aliphatic alkoxycarbonylamino, $(R^{10},R^{11})$-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{1-6}$ alkoxycarbonyl, $C_{1-6}$ aliphatic carbonylamino, ($C_{1-6}$ aliphatic carbonyl)($C_{1-6}$ aliphatic)amino, $(R^{10},R^{11})$-amino-$C_{1-6}$ aliphatic carbonylamino, $[(R^{10},R^{11})$-amino-$C_{1-6}$ aliphatic carbonyl][$C_{1-6}$ aliphatic]amino, $(R^{10},R^{11})$-amino-$C_{1-6}$ aliphatic sulfonylamino, $[(R^{10,R11})$-amino-$C_{1-6}$ aliphaticsulfonyl][$C_{1-6}$ aliphatic]amino, halogen, cyano, diethoxyphosphorylmethyl, nitro, trifluromethyl, and trifluoromethoxy, where $R^9$, $R^{10}$, $R^{11}$, Aryl, Cyc and Het are as defined below, with the proviso that where X is nitrogen, $R^4$, $R^5$ and $R^6$ is not nitro;

$R^7$ and $R^8$ may be the same or different and are independently selected from the group consisting of: hydrogen, halogen, $C_{1-12}$ alkoxy, hydroxy, $C_{1-3}$-aliphatic, and $C_{1-3}$ aliphatic;

with the proviso that $R^4$, $R^5$, $R^6$, $R^7$, and $R^8$ cannot simultaneously be hydrogen;

wherein $R^7$ may additionally be optionally fused to $R^5$ so as to form a fused benzo ring from the $R^5$ to the $R^7$ positions;

$R^9$ is selected from the group consisting of: $C_{1-12}$ aliphatic, hydroxy, $C_{1-12}$ alkoxy and halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazote, thiazine, thiazole, thiomorpholine, thiophene, thiopyran, triazine and triazole, where any of said heterocyclic rings may be optionally substituted by a substituent selected from the group consisting of: $C_{1-12}$ aliphatic, hydroxy, $C_{1-12}$ alkoxy, $(R^{10},R^{11})$-amino, $(R^{10},R^{11})$-amino-$C_{1-12}$ aliphatic, $(R^{10},R^{11})$-amino-$C_{1-12}$ aliphatic amino, oxo and dioxo;

and the pharmaceutically acceptable salts, polymorphs, esters, amides, carbamates, solvates, hydrates, affinity reagents and prodrugs thereof in either crystalline or amorphous form. The esters, amides and carbamates, are preferably hydrolyzable and more preferably are biohydrolyzable.

A more preferred genus of compounds of the present invention includes compounds of formula (II), defined as follows:

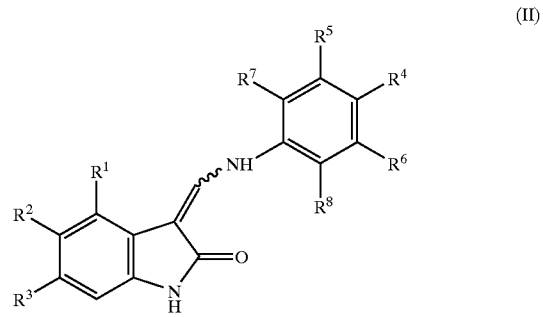

wherein $R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, fluoro, bromo, iodo, cyano, sulfonamide, or nitro, where $R^9$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^9$-Aryl-oxycarbonyl, $R^9$-oxycarbonyl-Aryl, Het, aminocarbonyl, $C_{1-12}$ aliphatic-aminocarbonyl, Aryl-$C_{1-12}$ aliphatic-aminocarbonyl, $R^9$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, $C_{1-12}$ aliphatic-sulfonyl, aminosulfonyl, or one or more substituents selected from the group consisting of: $C_{1-12}$ aliphatic-aminosulfonyl, where $R^9$, Aryl and Het are as defined below;

$R^1$ and $R^2$ are optionally joined to form a fused ring selected from the group as defined for Het below, and said fused ring is optionally substituted by $C_{1-12}$ aliphatic, halogen, nitro, cyano, $C_{1-12}$ alkoxy, amino, hydroxyl, $(R^{10}, R^{11})$-amino, or oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

$R^2$ and $R^3$ are optionally joined to form a fused ring selected from the group as defined for Het below, and said fused ring is optionally substituted by $C_{1-6}$ aliphatic or $C_{1-6}$ aliphatic-carbonyl;

with the proviso that $R^1$, $R^2$ and $R^3$ cannot simultaneously be hydrogen;

$R^4$, $R^5$ and $R^6$ may be the same or different and are independently selected from the group consisting of: hydrogen, $C_{1-12}$ aliphatic, thiol, $C_{1-6}$aliphatic-thio, di(trifluoromethyl)hydroxymethyl, carboxamide, mono-$C_{1-12}$aliphatic aminocarbonyl, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, $(R^{10},R^{11})$-amino-$C_{1-12}$ aliphatic aminocarbonyl, $(R^{10},R^{11})$-amino-$C_{1-12}$ aliphatic alkoxycarbonyl, $(R^{10},R^{11})$-amino-$C_{1-12}$ aliphatic aminocarbonylamino, $(R^{10},R^{11})$-amino-$C_{1-6}$ aliphatic alkoxycarbonylamino, $(R^{10},R^{11})$-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{1-6}$ alkoxycarbonyl, $C_{1-6}$ aliphatic carbonylamino, $(C_{1-6}$ aliphatic carbonyl)$(C_{1-6}$ aliphatic)amino, $(R^{10},R^{11})$amino-$C_{1-6}$ aliphatic carbonylamino, $[(R^{10},R^{11})$-amino-$C_{1-6}$ aliphatic carbonyl]$[C_{1-6}$ aliphatic]amino, $(R^{10},R^{11})$-amino-$C_{1-6}$ aliphatic sulfonylamino, $[(R^{10},R^{11})$-amino-$C_{1-6}$ aliphaticsUlfonyl]$[C_{1-6}$ aliphatic]amino, halogen, cyano, diethoxyphosphorylmethyl, nitro, trifluromethyl, or trifluoromethoxy, where $R^9$, $R^{10}$, $R^{11}$, Aryl, Cyc and Het are as defined below;

$R^7$ and $R^8$ may be the same or different and are independently selected from the group consisting of: hydrogen, halogen, $C_{1-12}$ alkoxy, hydroxy, $C_{1-3}$-aliphatic and $C_{1-3}$ aliphatic;

with the proviso that $R^4$, $R^5$, $R^6$, $R^7$ and $R^8$ cannot simultaneously be hydrogen;

wherein $R^7$ may additionally be optionally fused to $R^5$ so as to form a fused benzo ring from the $R^5$ to the $R^7$ positions;

$R^9$ is selected from the group consisting of: $C_{1-12}$ aliphatic, hydroxy, $C_{1-12}$ alkoxy, or halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of: $C_{1-12}$ aliphatic, hydroxy, $C_{1-12}$ alkoxy, $(R^{10},R^{11})$-amino, $(R^{10},R^{11})$-amino-$C_{1-12}$ aliphatic, $(R^{10},R^{11})$-amino-$C_{1-12}$ aliphatic amino, oxo or dioxo;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are biohydrolyzable.

Another preferred genus of compounds of the present invention includes compounds of formula (III), defined as follows:

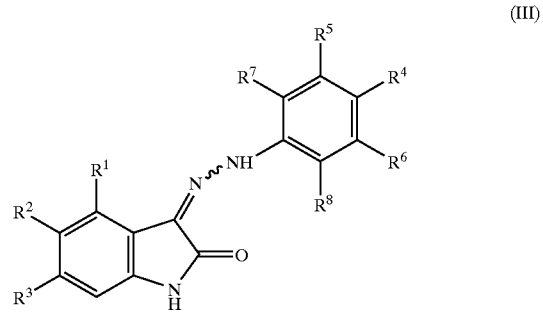

(III)

wherein $R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, fluoro, bromo, iodo, cyano, sulfonamide, or nitro, where $R^9$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^9$-Aryl-oxycarbonyl, $R^9$-oxycarbonyl-Aryl, Het, aminocarbonyl, $C_{1-12}$ aliphatic-aminocarbonyl, Aryl-$C_{1-12}$ aliphatic-aminocarbonyl, $R^9$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, $C_{1-12}$ aliphatic-sulfonyl, aminosulfonyl, or one or more substituents selected from the group consisting of: $C_{1-12}$ aliphatic-aminosulfonyl, where $R^9$, Aryl and Het are as defined below, with the proviso that $R^2$ is not chloro or 3,6-dihydro-6-methyl-2-oxo-2H-1,3,4-thiadiazin-5-yl;

$R^1$ and $R^2$ are optionally joined to form a fused ring selected from the group as defined for Het below, and said fused ring is optionally substituted by $C_{1-12}$ aliphatic, halogen, nitro, cyano, $C_{1-12}$ alkoxy, amino, hydroxyl, $(R^{10}, R^{11})$-amino, or oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below, with the proviso $R^3$ is not fluoro;

$R^2$ and $R^3$ are optionally joined to form a fused ring selected from the group as defined for Het below, and said fused ring is optionally substituted by $C_{1-6}$ aliphatic or $C_{1-6}$ aliphatic-carbonyl;

with the proviso that $R^1$, $R^2$ and $R^3$ cannot simultaneously be hydrogen;

$R^4$, $R^5$ and $R^6$ may be the same or different and are independently selected from the group consisting of: hydrogen, $C_{1-12}$ aliphatic, thiol, $C_{1-6}$aliphatic-thio, di(trifluoromethyl)hydroxymethyl, carboxamide, mono-$C_{1-12}$aliphatic aminocarbonyl, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, $(R^{10},R^{11})$-amino-$C_{1-12}$ aliphatic aminocarbonyl, $(R^{10},R^{11})$-amino-$C_{1-12}$ aliphatic alkoxycarbonyl, $(R^{10},R^{11})$-amino-$C_{1-12}$ aliphatic aminocarbonylamino, $(R^1,R^{11})$-amino-$C_{1-6}$ aliphatic alkoxycarbonylamino, $(R^{10},R^{11})$-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{-1-6}$ alkoxycarbonyl, $C_{1-6}$ aliphatic carbonylamino, ($C_{1-6}$ aliphatic carbonyl)($C_{1-6}$ aliphatic)amino, $(R^{10},R^{11})$-amino-$C_{1-6}$ aliphatic carbonylamino, $[(R^{10},R^{11})$-amino-$C_{1-6}$ aliphatic carbonyl][$C_{1-6}$ aliphatic]amino, $(R^{10},R^{11})$-amino-$C_{1-6}$ aliphatic sulfonylamino, $[(R^{10},R^{11})$-amino-$C_{1-6}$ aliphaticsulfonyl][$C_{1-6}$ aliphatic]amino, halogen, cyano, diethoxyphosphorylmethyl, nitro, trifluromethyl, or trifluoromethoxy, where $R^9$, $R^{10}$, $R^{11}$, Aryl, Cyc and Het are as defined below, with the proviso that $R^4$, $R^5$ and $R^6$ is not nitro;

$R^7$ and $R^8$ may be the same or different and are independently selected from the group consisting of: hydrogen, halogen, $C_{1-12}$ alkoxy, hydroxy, $C_{1-3}$-aliphatic and $C_{1-3}$ aliphatic;

with the proviso that $R^4$, $R^5$, $R^6$, $R^7$ and $R^8$ cannot simultaneously be hydrogen;

$R^9$ is selected from the group consisting of $C_{1-12}$ aliphatic, hydroxy, $C_{1-12}$ alkoxy, or halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of $C_{1-12}$ aliphatic, hydroxy, $C_{1-12}$ alkoxy, $(R^{10},R^{11})$-amino, $(R^{10},R^{11})$-amino-$C_{1-12}$ aliphatic, $(R^{10},R^1)$-amino-$C_{1-12}$ aliphatic amino, oxo or dioxo;

and the pharmaceutically acceptable salts, esters, amides, carbamates, solvates, hydrates, affinity reagents and pro-drugs thereof in either crystalline or amorphous form. The esters, amides and carbamates, are preferably hydrolyzable and more preferably are biohydrolyzable.

Another preferred genus of compounds of the present invention includes compounds of formula (IV), defined as follows:

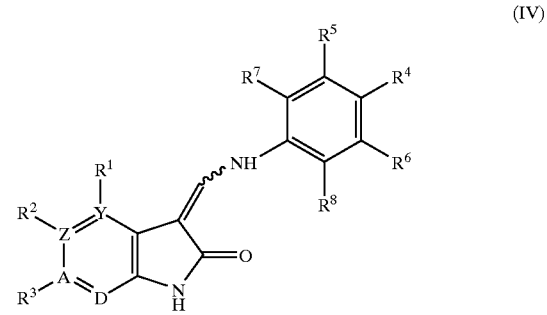

(IV)

wherein

Y, Z, A, and D are independently selected from the group consisting of: carbon and nitrogen, with the provisos that: (1) Z and D may be nitrogen, but otherwise no more than one of Y, Z, A, and D may be nitrogen, and (2) when Y, Z, or A are nitrogen, substituent $R^1$, $R^2$, or $R^3$ designated for the respective nitrogen atom is non-existent;

$R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, fluoro, bromo, iodo, cyano, sulfonamide, or nitro, where $R^9$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^9$-Aryl-oxycarbonyl, $R^9$-oxycarbonyl-Aryl, Het, aminocarbonyl, $C_{1-12}$ aliphatic-aminocarbonyl, Aryl-$C_{1-12}$ aliphatic-aminocarbonyl, $R^9$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, $C_{1-12}$ aliphatic-sulfonyl, aminosulfonyl, or one or more substituents selected from the group consisting of: $C_{1-12}$ aliphatic-aminosulfonyl, where Re, Aryl and Het are as defined below;

$R^1$ and $R^2$ are optionally joined to form a fused ring selected from the group as defined for Het below, and said fused ring is optionally substituted by $C_{1-12}$ aliphatic, halogen, nitro, cyano, $C_{1-12}$ alkoxy, amino, hydroxyl, $(R^{10}, R^{11})$-amino, or oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

$R^2$ and $R^3$ are optionally joined to form a fused ring selected from the group as defined for Het below, and said fused ring is optionally substituted by $C_{1-6}$ aliphatic or $C_{1-6}$ aliphatic-carbonyl;

with the proviso that $R^1$, $R^2$ and $R^3$ cannot simultaneously be hydrogen;

$R^4$, $R^5$ and $R^6$ may be the same or different and are independently selected from the group consisting of hydrogen, $C_{1-12}$ aliphatic, thiol, $C_{1-6}$aliphatic-thio, di(trifluoromethyl)hydroxymethyl, carboxamide, mono-$C_{1-12}$aliphatic aminocarbonyl, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, $(R^{10},R^{11})$-amino-$C_{1-12}$ aliphatic aminocarbonyl, $(R^{10},R^{11})$-amino-$C_{1-12}$ aliphatic alkoxycarbonyl, $(R^{10},R^{11})$-amino-$C_{1-12}$ aliphatic aminocarbonylamino, $(R^{10},R^{11})$-amino-$C_{1-6}$ aliphatic alkoxycarbonylamino, $(R^{10},R^1)$-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{1-6}$ alkoxycarbonyl, $C_{1-6}$ aliphatic carbonylamino, $(C_{1-6}$ aliphatic carbonyl)($C_{1-6}$ aliphatic)amino, $(R^{10},R^{11})$amino-$C_{1-6}$ aliphatic carbonylamino, $[(R^{10},R^{11})$-amino-$C_{1-6}$ aliphatic carbonyl]$[C_{1-6}$ aliphatic]amino, $(R^{10},R^{11})$-amino-$C_{1-6}$ aliphatic sulfonylamino, $[(R^{10},R^{11})$-amino-$C_{1-6}$ aliphaticsulfonyl]$[C_{1-6}$ aliphatic]amino, halogen, cyano, diethoxyphosphorylmethyl, nitro, trifluromethyl, or trifluoromethoxy, where $R^9$, $R^{10}$, $R^{11}$, Aryl, Cyc and Het are as defined below;

$R^7$ and $R^8$ may be the same or different and are independently selected from the group consisting of: hydrogen, halogen, $C_{1-12}$ alkoxy, hydroxy, $C_{1-3}$-aliphatic and $C_{1-3}$ aliphatic;

with the proviso that $R^4$, $R^5$, $R^6$, $R^7$ and $R^8$ cannot simultaneously be hydrogen;

wherein $R^7$ may additionally be optionally fused to $R^5$ so as to form a fused benzo ring from the $R^5$ to the $R^7$ positions;

$R^9$ is selected from the group consisting of: $C_{1-12}$ aliphatic, hydroxy, $C_{1-12}$ alkoxy, or halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl or cyclooctyl, and optionally has one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of: $C_{1-12}$ aliphatic, hydroxy, $C_{-1-12}$ alkoxy, $(R^{10},R^{11})$-amino, $(R^{10},R^{11})$amino-$C_{1-12}$ aliphatic, $(R^{10},R^{11})$-amino-$C_{1-12}$ aliphatic amino, oxo or dioxo;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are biohydrolyzable.

While the ensuing discussion refers to the compound of formula (I), it will be understood that the compounds of formula (I) includes the compounds of formulas (II), (III) and (IV); accordingly, references hereafter to formula (I) should hereafter be understood to includes the compounds of formulas (II), (III) and (IV) as well as the compounds of formula (I). Furthermore, references in the ensuing discussion to the formula (I) should also be understood as referring to the compounds of Examples 163–212 of Table 5 below which, while not included within the general formula (I), have been found by the inventors to have Kinase inhibiting properties.

Due to the presence of an oxindole exocyclic double bond, also included in the compounds of the invention are their respective pure E and Z geometric isomers as well as mixtures of E and Z isomers. The invention as described and claimed does not set any limiting ratios on prevalence of Z to E isomers.

Likewise, it is understood that compounds of formula (I) as used herein includes all tautomeric forms other than the specific tautomer represented by the formula.

Certain of the compounds as described contain one or more chiral, or asymmetric, centers and are therefore be capable of existing as optical isomers that are either dextrorotatory or levorotatory. Also included in the compounds of the invention are the respective dextrorotatory or levorotatory pure preparations, and mixtures thereof.

Certain compounds of formula (I) above are optionally provided in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) are optionally provided in various tautomeric forms within the scope of the present invention.

The present invention also provides compounds of formula (I) and pharmaceutically acceptable salts thereof (hereafter collectively referred to as the "active compounds") for use in medical therapy, and particularly in the treatment of disorders mediated by a Kinase, such as VEGF-R2 tyrosine kinase, including, for example, as angiogenesis accompanying malignant tumor growth.

A further aspect of the invention provides a method of treatment of a human or animal suffering from a disorder mediated by a protein kinase, said treatment comprising administering an effective amount of an active compound of formula (I) to the human or animal patient.

In a related aspect the present invention comprises a method for inhibiting a kinase comprising bringing said kinase into contact with a compound of formula (I).

Another aspect of the present invention provides a method for using an active compound of formula (I), in the preparation of a medicament for the treatment of malignant tumors, or for the treatment of disorders involving abnormal angiogenesis, such as arthritis, diabetic retinopathy, macular degeneration and psoriasis. Alternatively, compounds of formula (I) can be used in the preparation of a medicament for the treatment of a disease mediated by a kinase selected from the group consisting of: abl, ARaf, ATK, ATM, bcr-abl, Blk, BRaf, Brk, Btk, CDK1, CDK2, CDK3, CDK4, CDK5, CDK6, CDK7, CDK8, CDK9, cfms, c-fms, c-kit, c-met, cRaf1, CSF1R, CSK, c-src, EGFR, ErbB2, ErbB3, ErbB4, ERK, ERK1, ERK2, Fak, fes, FGFR1, FGFR2, FGFR3, FGFR4, FGFR5, Fgr, FLK4, Fps, Frk, Fyn, GSK, gsk3a, gsk3b, Hck, IGF-1R, IKK, IKK1, IKK2, IKK3, INS-R, Integrin-linkedkinase, Jak, JAK1, JAK2, JAK3, JNK, JNK, Lck, Lyn, MEK, MEK1, MEK2, p38, PDGFR, PIK, PKB1, PKB2, PKB3, PKC, PKCα, PKCβ, PKCδ, PKCε, PKCγ, PKCλ, PKCμ, PKCζ, PLK1, Polo-like kinase, PYK2, tie1, tie2, TrkA, TrkB, TrkC, UL13, UL97, VEGF-R1, VEGF-R2, Yes and Zap70.

Additionally, compounds of formula (I) can be used in the preparation of a medicament for the treatment of organ transplant rejection, tumor growth, chemotherapy-induced mucositis, radiation-induced mucositis, plantar-palmar syndrome, chemotherapy-induced alopecia, chemotherapy-induced thrombocytopenia, chemotherapy-induced leukopenia and hirsutism or of treating a disease state selected from the group consisting of: mucocitis, restenosis, atherosclerosis, rheumatoid arthritis, angiogenesis, hepatic cirrhosis, glomerulonephritis, diabetic nephropathy, malignant nephrosclerosis, chronic obstructive pulmonary disease, thrombotic microangiopathy, aglomerulopathy, psoriasis, diabetes mellitus, inflammation, a neurodegenerative disease, macular degeneration, actinic keratosis and hyperproliferative disorders.

Another aspect of the present invention provides the use of an active compound of formula (I), in coadministration or alternating administration with previously known anti-tumor therapies for more effective treatment of such tumors.

Another aspect of the present invention provides the use of an active compound of formula (I) in the preparation of a medicament for the treatment of viral or eukaryotic infections.

Other aspects of the present invention related to the inhibition of protein kinases are discussed in more detail below.

Compounds synthesized as part of the present invention which are currently preferred are listed in Tables 1–3 below. Compounds are identified by the numbers shown in the first column; variables below in the rest of the columns are with reference to the generic structure (I). Corresponding IUPAC nomenclature are disclosed in Table 4. Since all substituents at each point of substitution are capable of independent synthesis of each other, the tables are to be read as a matrix in which any combination of substituents is within the scope of the disclosure and claims of the invention.

TABLE 1

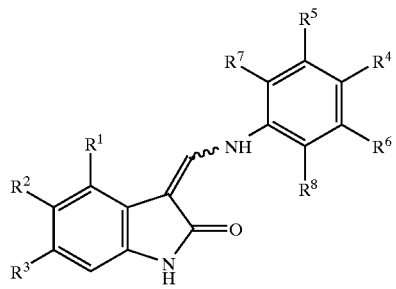

(II)

| Example | R¹ | R² | R³ | R⁴ | R⁵ | R⁶ | R⁷ | R⁸ |
|---|---|---|---|---|---|---|---|---|
| 1 | H | H | Br | 4-morpholino | H | H | H | H |
| 2 | H | H | Br | 4-pyridylmethyl | H | H | H | H |
| 3 | —NH—C=N— | | H | CH₃ | H | H | H | H |
| 4 | —NH—N=N— | | H | NO₂ | CH₃ | H | H | H |
| 5 | —NH—N=N— | | H | NO₂ | CF₃ | H | H | H |
| 6 | —NH—N=N— | | H | NO₂ | Cl | H | H | H |
| 7 | —NH—N=N— | | H | NO₂ | CH₃ | CH₃ | H | H |
| 8 | —NH—N=N— | | H | —C(OH)(CF₃)₂ | H | H | H | H |

TABLE 1-continued

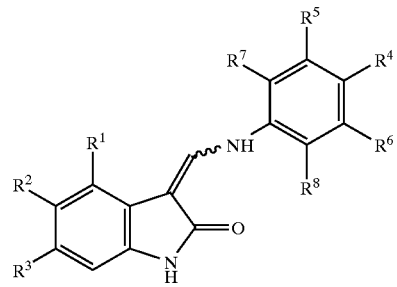

(II)

| Example | R¹ | R² | R³ | R⁴ | R⁵ | R⁶ | R⁷ | R⁸ |
|---|---|---|---|---|---|---|---|---|
| 9 | —NH—N=N— | | H | —CH₂CH₂OH | H | H | H | H |
| 10 | —S—CH=N— | | H | Sme | H | H | H | H |
| 11 | —S—CH=N— | | H | H | OMe | OMe | H | H |
| 12 | —S—CH=N— | | H | OH | H | H | H | H |
| 13 | —CH=CH—CH=N— | | H | H | OMe | H | H | H |
| 14 | —CH=CH—CH=N— | | H | H | CN | OMe | H | H |
| 15 | —CH=CH—CH=N— | | H | CH₃ | H | H | H | H |
| 16 | —CH=CH—CH=N— | | H | OMe | H | H | H | H |
| 17 | —NH—N=N— | | H | H | CN | H | H | H |
| 18 | —NH—N=N— | | H | CH₃ | H | H | H | H |
| 19 | —NH—N=N— | | H | OMe | H | H | H | H |
| 20 | —S—CH=N— | | H | 4-morpholino | H | H | H | H |
| 21 | —S—CH=N— | | H | NHAc | H | H | H | H |
| 22 | —S—CH=N— | | H | —CH₂CH₂OH | H | H | H | H |
| 23 | —S—CH=N— | | H | 4-pyridylmethyl | H | H | H | H |
| 24 | —S—CH=N— | | H | CONH₂ | H | H | H | H |
| 25 | H | H | Br | 4-morpholino | H | H | H | H |
| 26 | H | H | Br | CONH₂ | H | H | H | H |
| 27 | H | H | Br | NHAc | H | H | H | H |
| 28 | H | H | Br | —CH₂CH₂OH | H | H | H | H |
| 29 | —CH=CH—CH=N— | | H | 4-morpholino | H | H | H | H |
| 30 | —CH=CH—CH=N— | | H | 4-pyridylmethyl | H | H | H | H |
| 31 | —CH=CH—CH=N— | | H | NHAc | H | H | H | H |
| 32 | —CH=CH—CH=N— | | H | —CH₂CH₂OH | H | H | H | H |
| 33 | —CH=CH—CH=N— | | H | CONH₂ | H | H | H | H |
| 34 | —CH=CH—CH=N— | | H | OH | H | H | H | H |
| 35 | H | H | 2-furanyl | 4-morpholino | H | H | H | H |
| 36 | H | H | 2-furanyl | NHAc | H | H | H | H |
| 37 | H | H | 2-furanyl | —CH₂CH₂OH | H | H | H | H |
| 38 | H | H | —CH=CH₂ | 4-morpholino | H | H | H | H |
| 39 | H | H | —CH=CH₂ | 4-pyridylmethyl | H | H | H | H |
| 40 | H | H | —CH=CH₂ | NHAc | H | H | H | H |
| 41 | H | H | —CH=CH₂ | —CH₂CH₂OH | H | H | H | H |
| 42 | H | H | 2-furanyl | 4-pyridylmethyl | H | H | H | H |
| 43 | H | H | 2-furanyl | OH | H | H | H | H |
| 44 | H | H | 2-thienyl | 4-morpholino | H | H | H | H |
| 45 | H | H | 2-thienyl | NHAc | H | H | H | H |
| 46 | H | H | Br | H | —CH₂OH | H | H | H |
| 47 | H | H | Br | 5-methyl-3-pyrazolon-1-yl | H | H | H | H |
| 48 | —S—CH=N— | | H | 3-ethyl-piperidine-2,6-dion-3-yl | H | H | H | H |
| 49 | —S—CH=N— | | H | OPh | H | H | H | H |
| 50 | —S—CH=N— | | H | OCH₂Ph | H | H | H | H |
| 51 | —S—CH=N— | | H | 4-(methoxycarbonyl)phenoxy | H | H | H | H |
| 52 | —S—CH=N— | | H | 3-(methoxycarbonyl)phenoxy | H | H | H | H |
| 53 | —S—CH=N— | | H | H | —CH₂OH | H | H | H |
| 54 | —S—CH=N— | | H | H | CONH₂ | H | H | H |
| 55 | —S—CH=N— | | H | 5-methyl-3-pyrazolon-1-yl | H | H | H | H |
| 56 | —S—CH=N— | | H | CO₂Me | H | H | H | H |
| 57 | —S—CH=N— | | H | CN | H | H | H | H |
| 58 | —S—CH=N— | | H | NMeAc | H | H | H | H |
| 59 | —CH=CH—CH=N— | | H | OPh | H | H | H | H |
| 60 | —CH=CH—CH=N— | | H | OCH₂Ph | H | H | H | H |
| 61 | —CH=CH—CH=N— | | H | 4-(methoxycarbonyl)phenoxy | H | H | H | H |
| 62 | —CH=CH—CH=N— | | H | 3-(methoxycarbonyl)phenoxy | H | H | H | H |
| 63 | —CH=CH—CH=N— | | H | 3-ethyl-piperidine-2,6-dion-3-yl | H | H | H | H |
| 64 | —CH=CH—CH=N— | | H | benzoyl | H | H | H | H |
| 65 | —CH=CH—CH=N— | | H | H | —CH₂OH | H | H | H |
| 66 | —CH=CH—CH=N— | | H | 5-methyl-3-pyrazolon-1-yl | H | H | H | H |
| 67 | —CH=CH—CH=N— | | H | 2-(4-hydroxyphenyl)ethenyl | H | H | H | H |
| 68 | —CH=CH—CH=N— | | H | H | CONH₂ | H | H | H |
| 69 | —CH=CH—CH=N— | | H | CN | H | H | H | H |

TABLE 1-continued

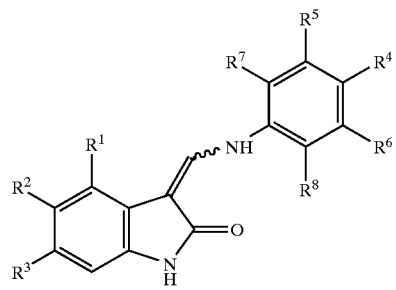

(II)

| Example | R¹ | R² | R³ | R⁴ | R⁵ | R⁶ | R⁷ | R⁸ |
|---|---|---|---|---|---|---|---|---|
| 70 | —CH=CH—CH=N— | | H | CO₂Me | H | H | H | H |
| 71 | —S—CH=N— | | H | SO₂CH₂CH₂NEt₂ | H | H | H | H |
| 72 | —CH=CH—CH=N— | | H | SO₂CH₂CH₂NEt₂ | H | H | H | H |
| 73 | H | H | Ph | H | CONH₂ | H | H | H |
| 74 | H | H | Ph | —CH₂PO(OEt)₂ | H | H | H | H |
| 75 | H | H | Ph | H | CN | H | H | H |
| 76 | H | H | Ph | H | H | H | —CH₂CH₂OH | H |
| 77 | H | H | Ph | H | —CH₂OH | H | H | H |
| 78 | H | H | Ph | H | H | H | OMe | H |
| 79 | H | H | Ph | 5-methyl-3-pyrazolon-1-yl | H | H | H | H |
| 80 | H | H | Ph | I | H | H | H | H |
| 81 | H | H | 2-furanyl | H | CONH₂ | H | H | H |
| 82 | H | H | 2-furanyl | —CH₂PO(OEt)₂ | H | H | H | H |
| 83 | H | H | 2-furanyl | H | CN | H | H | H |
| 84 | H | H | 2-furanyl | H | H | H | —CH₂CH₂OH | H |
| 85 | H | H | 2-furanyl | H | —CH₂OH | H | H | H |
| 86 | H | H | 2-furanyl | H | H | H | OMe | H |
| 87 | H | H | 2-furanyl | 5-methyl-3-pyrazolon-1-yl | H | H | H | H |
| 88 | H | H | 2-furanyl | I | H | H | H | H |

TABLE 2

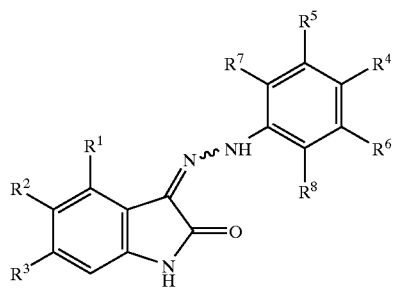

(III)

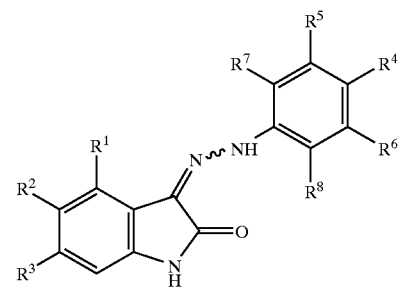

(III)

| Example | R¹ | R² | R³ | R⁴ | R⁵ | R⁶ | R⁷ | R⁸ |
|---|---|---|---|---|---|---|---|---|
| 89 | —NH—N=N— | | H | OMe | H | H | H | H |
| 90 | —NH—N=N— | | H | 5-oxazolyl | H | H | H | H |
| 91 | —NH—N=N— | | H | CH₃ | H | H | H | H |
| 92 | —NH—N=N— | | H | 2-(2-pyridyl)ethenyl | H | H | H | H |
| 93 | —S—CH=N— | | H | H | OMe | H | H | H |
| 94 | CH₃ | OH | CH₃ | CH₃ | H | H | H | H |
| 95 | —NH—N=N— | | H | CF₃ | H | H | H | H |
| 96 | —S—CH=N— | | H | H | F | H | H | H |
| 97 | —S—CH=N— | | H | F | H | H | H | H |
| 98 | —S—CH=N— | | H | Br | H | H | H | H |

TABLE 3

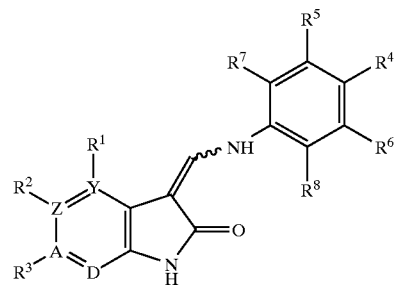

(IV)

| Example | Y | Z | A | D | R¹ | R² | R³ | R⁴ | R⁵ | R⁷ | R⁶ | R⁸ |
|---|---|---|---|---|---|---|---|---|---|---|---|---|
| 99 | C | C | C | N | H | Ph | H | W | CONH$_2$ | H | H | H |
| 100 | C | C | C | N | H | Ph | H | —CH$_2$PO(OEt)$_2$ | H | H | H | H |
| 101 | C | C | C | N | H | Ph | H | H | CN | H | H | H |
| 102 | C | C | C | N | H | Ph | H | H | H | —CH$_2$CH$_2$OH | H | H |
| 103 | C | C | C | N | H | Ph | H | H | —CH$_2$OH | H | H | H |
| 104 | C | C | C | N | H | Ph | H | H | H | OMe | H | H |
| 105 | C | C | C | N | H | Ph | H | 5-methyl-3-pyrazolon-1-yl | H | H | H | H |
| 106 | C | C | C | N | H | Ph | H | I | H | H | H | H |
| 107 | C | C | C | N | H | 2-furanyl | H | H | CONH$_2$ | H | H | H |
| 108 | C | C | C | N | H | 2-furanyl | H | —CH$_2$PO(OEt)$_2$ | H | H | H | H |
| 109 | C | C | C | N | H | 2-furanyl | H | H | CN | H | H | H |
| 110 | C | C | C | N | H | 2-furanyl | H | H | H | —CH$_2$CH$_2$OH | H | H |
| 111 | C | C | C | N | H | 2-furanyl | H | H | —CH$_2$OH | H | H | H |
| 112 | C | C | C | N | H | 2-furanyl | H | H | H | OMe | H | H |
| 113 | C | C | C | N | H | 2-furanyl | H | 5-methyl-3-pyrazolon-1-yl | H | H | H | H |
| 114 | C | C | C | N | H | 2-furanyl | H | I | H | H | H | H |
| 115 | C | C | C | N | H | 3-thienyl | H | H | CONH$_2$ | H | H | H |
| 116 | C | C | C | N | H | 3-thienyl | H | —CH$_2$PO(OEt)$_2$ | H | H | H | H |
| 117 | C | C | C | N | H | 3-thienyl | H | H | CN | H | H | H |
| 118 | C | C | C | N | H | 3-thienyl | H | H | H | —CH$_2$CH$_2$OH | H | H |
| 119 | C | C | C | N | H | 3-thienyl | H | H | —CH$_2$OH | H | H | H |
| 120 | C | C | C | N | H | 3-thienyl | H | H | H | OMe | H | H |
| 121 | C | C | C | N | H | 3-thienyl | H | 5-methyl-3-pyrazolon-1-yl | H | H | H | H |
| 122 | C | C | C | N | H | 3-thienyl | H | I | H | H | H | H |
| 123 | C | C | C | N | H | Br | H | H | CONH$_2$ | H | H | H |
| 124 | C | C | C | N | H | Br | H | —CH$_2$PO(OEt)$_2$ | H | H | H | H |
| 125 | C | C | C | N | H | Br | H | H | CN | H | H | H |
| 126 | C | C | C | N | H | Br | H | H | H | —CH$_2$CH$_2$OH | H | H |
| 127 | C | C | C | N | H | Br | H | H | —CH$_2$OH | H | H | H |
| 128 | C | C | C | N | H | Br | H | H | H | OMe | H | H |
| 129 | C | C | C | N | H | Br | H | 5-methyl-3-pyrazolon-1-yl | H | H | H | H |
| 130 | C | C | C | N | H | Br | H | I | H | H | H | H |
| 131 | C | C | C | N | H | H | Cl | H | CONH$_2$ | H | H | H |
| 132 | C | C | C | N | H | H | Cl | —CH$_2$PO(OEt)$_2$ | H | H | H | H |
| 133 | C | C | C | N | H | H | Cl | H | CN | H | H | H |
| 134 | C | C | C | N | H | H | Cl | H | H | —CH$_2$CH$_2$OH | H | H |
| 135 | C | C | C | N | H | H | Cl | H | —CH$_2$OH | H | H | H |
| 136 | C | C | C | N | H | H | Cl | H | H | OMe | H | H |
| 137 | C | C | C | N | H | H | Cl | 5-methyl-3-pyrazolon-1-yl | H | H | H | H |
| 138 | C | C | C | N | H | H | Cl | I | H | H | H | H |
| 139 | C | C | C | N | H | CO$_2$Et | H | H | CONH$_2$ | H | H | H |
| 140 | C | C | C | N | H | CO$_2$Et | H | —CH$_2$PO(OEt)$_2$ | H | H | H | H |
| 141 | C | C | C | N | H | CO$_2$Et | H | H | CN | H | H | H |
| 142 | C | C | C | N | H | CO$_2$Et | H | H | H | —CH$_2$CH$_2$OH | H | H |
| 143 | C | C | C | N | H | CO$_2$Et | H | H | —CH$_2$OH | H | H | H |
| 144 | C | C | C | N | H | CO$_2$Et | H | H | H | OMe | H | H |
| 145 | C | C | C | N | H | CO$_2$Et | H | 5-methyl-3-pyrazolon-1-yl | H | H | H | H |
| 146 | C | C | C | N | H | CO$_2$Et | H | I | H | H | H | H |
| 147 | C | C | C | N | H | H | H | H | CONH$_2$ | H | H | H |
| 148 | C | C | C | N | H | H | H | —CH$_2$PO(OEt)$_2$ | H | H | H | H |
| 149 | C | C | C | N | H | H | H | H | CN | H | H | H |
| 150 | C | C | C | N | H | H | H | H | H | —CH$_2$CH$_2$OH | H | H |
| 151 | C | C | C | N | H | H | H | H | —CH$_2$OH | H | H | H |
| 152 | C | C | C | N | H | H | H | H | H | OMe | H | H |
| 153 | C | C | C | N | H | H | H | 5-methyl-3-pyrazolon-1-yl | H | H | H | H |
| 154 | C | C | C | N | H | H | H | I | H | H | H | H |
| 155 | N | C | C | C | — | H | H | H | CONH$_2$ | H | H | H |
| 156 | N | C | C | C | — | H | H | —CH$_2$PO(OEt)$_2$ | H | H | H | H |
| 157 | N | C | C | C | — | H | H | H | CN | H | H | H |
| 158 | N | C | C | C | — | H | H | H | H | —CH$_2$CH$_2$OH | H | H |
| 159 | N | C | C | C | — | H | H | H | —CH$_2$OH | H | H | H |

TABLE 3-continued (IV)

| Example | Y | Z | A | D | R¹ | R² | R³ | R⁴ | R⁵ | R⁷ | R⁶ | R⁸ |
|---|---|---|---|---|---|---|---|---|---|---|---|---|
| 160 | N | C | C | C | — | H | H | H | H | OMe | H | H |
| 161 | N | C | C | C | — | H | H | 5-methyl-3-pyrazolon-1-yl | H | H | H | H |
| 162 | N | C | C | C | — | H | H | I | H | H | H | H |
| 163 | C | C | C | N | H | Ph | H | OH | —CH=CH—CH=CH— | | H | H |
| 164 | C | C | C | N | H | 2-furanyl | H | OH | —CH=CH—CH=CH— | | H | H |
| 165 | C | C | C | N | H | 3-thienyl | H | OH | —CH=CH—CH=CH— | | H | H |
| 166 | C | C | C | N | H | Br | H | OH | —CH=CH—CH=CH— | | H | H |
| 167 | C | C | C | N | H | H | Cl | OH | —CH=CH—CH=CH— | | H | H |
| 168 | C | C | C | N | H | CO₂Et | H | OH | —CH=CH—CH=CH— | | H | H |
| 169 | C | C | C | N | H | H | H | OH | —CH=CH—CH=CH— | | H | H |
| 170 | N | C | C | N | — | H | H | OH | —CH=CH—CH=CH— | | H | H |
| 171 | C | C | C | C | H | H | 2-furanyl | OH | —CH=OH—CH=CH— | | H | H |
| 172 | C | C | C | C | H | H | Phenyl | OH | —CH=CH—CH=CH— | | H | H |

Standard accepted nomenclature corresponding to the Examples set forth in this specification are set forth below. In some cases nomenclature is given for one or more possible isomers.

TABLE 4

| Example 1 | 6-Bromo-3-{(Z and E)-[4-(4-morpholinyl)anilino]-methylidene}-1,3-dihydro-2H-indol-2-one; |
| Example 2 | 6-Bromo-3-{(Z and E)-[4-(4-pyridinylmethyl)anilino]-methylidene}-1,3-dihydro-2H-indol-2-one; |
| Example 3 | 8-[(Z and E)4-Toluidinomethylene]-6,8-dihydroimidazo-[4,5-e]indol-7(3H)-one; |
| Example 4 | 8-[(Z and E)-(3-Methyl-4-nitroanilino)methylidene]-3,6-dihydro[1,2,3]triazolo[4,5-e]indol-7-one; |
| Example 5 | 8-{(Z and E)-[4-Nitro-3-(trifluoromethyl)anilino][ methylidene}-3,6-dihydro[1,2,3]triazolo[4,5-e]indol-7-one; |
| Example 6 | 8-[(Z and E)-(3-Chloro-4-nitroanilino)methylidene]-1,6-dihydro[1,2,3]triazolo[4,e]indol-7-one; |
| Example 7 | 8-[(Z and E)-(3,5-Dimethyl-4-nitroanilino)methylidene]-1,6-dihydro[1,2,3]triazolo[4,5-e]indol-7-one; |
| Example 8 | 8-((Z and E)-{4-[2,2,2-Trifluor-1-hydroxy-1-(trifluoromethyl)ethyl]anilino}methylidene)-1,6-dihydro[1,2,3]triazolo[4,5-e]indol-7-one; |
| Example 9 | 8-{(Z and E)-[4-(2-Hydroxyethyl)anilino]-methylidene}-1,6-dihydro[1,2,3]triazolo[4,5-e]indol-7-one; |
| Example 10 | 8-{(Z)-[4-(Methylsulfanyl)anilino]methylidene}-6H-[1,3]thiazolo[5,4-e]indol-7-one; |
| Example 11 | 8-[(Z)-(3,5-Dimethoxyanilino)methylidene]-6H-[1,3]-thiazolo[5,4-e]indol-7-one; |
| Example 12 | 8-[(Z)-(4-Hydroxyanilino)methylidene]-6H-[1,3]thiazolo-[5,4-e]indol-7-one; |
| Example 13 | 1-[(Z)-(3-Methoxyanilino)methylidene]-1,3-dihydro-2H-pyrrolo[3,2-f]quinolin-2-one; |
| Example 14 | 3-{[(Z)-(2-Oxo-2,3-hydro-1H-pyrrolo[3,2-f]quinolin-1-ylidene)methyl)amino}benzonitrile; |
| Example 15 | 1-[(Z)-4-Toluidinomethylidene]-1,3-dihydro-2H-pyrrolo-[3,2-f]-quinolin-2-one; |
| Example 16 | 1-[(Z)-(4-Methoxyanilino)methylidene]-1,3-dihydro-2H-pyrrolo[3,2-f]quinolin-2-one; |
| Example 17 | 3-({[(Z and E)-7-Oxo-6,7-dihydro[1,2,3]triazolo[4,5-e]indol-8(1H)-ylidene]methyl}amino)benzonitrile; |
| Example 18 | 8-[(Z and E)-4-Toluidinomethylidene]-1,6-dihydro[1,2,3]-triazolo[4,5-e]indol-7-one; |

TABLE 4-continued

| Example 19 | 8-[(Z and E)-(4-Methoxyanilino)methylidene]-1,6-dihydro[1,2,3]triazolo[4,5-e]indol-7-one; |
| Example 20 | 8-{(Z)-[4-(4-Morpholinyl)anilino]methylidene)-6H-[1,3]-thiazolo[5,4-e]indol-7-one; |
| Example 21 | N-(4-{[(Z)-(7-Oxo-6,7-dihydro-8H-[1,3]thiazolo[5,4-e]-indol-8-ylidene)methyl]amino}phenyl)acetamide; |
| Example 22 | 8-{(Z)-[4-(2-Hydroxyethyl)anilino]methylidene)-6H-[1,3]-thiazolo[5,4-e]indol-7-one; |
| Example 23 | 8-{(Z)-[4-(4-Pyridinylmethyl)anilino]methylidene}-6H-[1,3]thiazoio[5,4-e]indol-7-one; |
| Example 24 | 4-{[[(Z)-(7-Oxo-6,7-dihydro-8H-[1,3]thiazolo[5,4-e]indol-8-ylidene)methyl]amino}benzamide; |
| Example 25 | 6-Bromo-3-{(Z and E)-[4-(4-morpholinyl)anilino]-methylidene)-1,3-dihydro-2H-indol-2-one; |
| Example 26 | 4-{[(Z and E)-(6-Bromo-2-oxo-1,2-dihydro-3H-indol-3-ylidene)methyl]amino}benzamide; |
| Example 27 | N-(4-{[(Z and E)-(6-Bromo-2-oxo-1,2-dihydro-3H-indol-3-ylidene)methyl]amino}phenyl)acetamide; |
| Example 28 | 6-Bromo-3-{(Z and E)-[4-(2-hydroxyethyl)anilino]-methylidene)-1,3-dihydro-2H-indol-2-one; |
| Example 29 | 1-{(Z)-[4-(4-Morpholinyl)anilino]methylidene)-1,3-dihydro-2H-pyrrolo[3,2-f]quinolin-2-one; |
| Example 30 | 1-{(Z)-[4-(4-Pyridinylmethyl)anilino]methylidene)-1,dihydro-2H-pyrrolo[3,2-f]quinolin-2-one; |
| Example 31 | N-(4-{[(Z)-(2-Oxo-2,3-dihydro-1H-pyrrolo[3,2-f]quinolin-1-ylidene)methyl]amino}phenyl)acetamide; |
| Example 32 | 1-{(Z)-[4-(2-Hydroxyethyl)anilino]methylidene}-1,3-dihydro-2H-pyrrolo[3,2-f]quinolin-2-one; |
| Example 33 | 4-{[[(Z)-(2-Oxo-2,3-dihydro-1H-pyrrolo[3,2-f]quinolin-1-ylidene)methyl]amino}benzamide; |
| Example 34 | 1-[(Z)-(4-Hydroxyanilino)methylidene]-1,3-dihydro-2H-pyrrolo[3,2-f]quinolin-2-one; |
| Example 35 | 6-(2-Furyl)-3-{(Z and E)-[4-(4-morpholinyl)anilino]-methylidene)-1,3-dihydro-2H-indol-2-one; |
| Example 36 | N-[4-({(Z and E)-[6-(2-Furyl)-2-oxo-1,2-dihydro-3H-indol-3-ylidene]methyl}amino)phenyl]acetamide; |
| Example 37 | 6-(2-Furyl)-3-{(Z and E)-[4-(2-hydroxyethyl)anilino]-methylidene)-1,3-dihydro-2H-indol-2-one; |
| Example 38 | 3-{(Z and E)-[4-(4-Morpholinyl)anilino]methylidene)-6-vinyl-1,3-dihydro-2H-indol-2-one; |
| Example 39 | 3-{(Z and E)-[4-(4-Pyridinylmethyl)anilino]methylidene}-6-vinyl-1,3-dihydro-2H-indol-2-one; |

TABLE 4-continued

| | |
|---|---|
| Example 40 | N-(4-{(Z and E)-[(2-Oxo-6-vinyl-1,2-dihydro-3H-indol-3-ylidene)methyl]amino}phenyl)acetamide; |
| Example 41 | 3-{(Z and E)-[4-(2-Hydroxyethyl)anilino]methylidene}-6-vinyl-1,3-dihydro-2H-indol-2-one; |
| Example 42 | 6-(2-Furyl)-3-{(Z and E)-[4-(4-pyridinylmethyl)anilino]-methylidene}-1,3-dihydro-2H-indol-2-one; |
| Example 43 | 6-(2-Furyl)-3-[(Z and E)-(4-hydroxyanilino)methylidene]-1,3-dihydro-2H-indol-2-one; |
| Example 44 | 3-{(Z and E)-[4-(4-Morpholinyl)anilino]methylidene}-6-(2-thienyl)-1,3-dihydro-2H-indol-2-one; |
| Example 45 | N-(4-({(Z and E)-[2-Oxo-(2-thienyl)-1,2-dihydro-3H-indol-3-ylidene]methyl}amino)phenyl]acetamide; |
| Example 46 | 6-Bromo-3-{(Z and E)-[3-(hydroxymethyl)anilino]-methylidene}-1,3-dihydro-2H-indol-2-one; |
| Example 47 | 6-Bromo-{(Z and E)-[4-(methyl-3-oxo-2,3-dihydro-1H-pyrazol-1-yl)anilino]methylidene}-1,3-dihydro-2H-indol-2-one; |
| Example 48 | 3-Ethyl-3-(4-{(Z and E )-[(7-oxo-6,7-dihydro-8H-[1,3]-thiazolo[5,4-e]indol-8-ylidene)methyl]amino}-phenyl)-2,6-piperidinedione; |
| Example 49 | 8-[(Z)-(4-Phenoxyanilino)methylidene]-6 H-[1,3]thiazolo-[5,4-e]indol-7-one; |
| Example 50 | 8-{(Z)-[4-(Benzyloxy)anilino]methylidene}-6H-[1,3]-thiazolo[5,4-e]indol-7-one; |
| Example 51 | Methyl 4-(4-{[((Z)-7-oxo-6,7-dihydro-8H-[1,3]thiazolo-[5,4-e]indol-8-ylidene)methyl]amino}phenoxy)benzoate; |
| Example 52 | Methyl 3-(4-{(Z)-[(7-oxo-6,7-dihydro-8H-[1,3]thiazolo-[5,4-e]indol-8-ylidene)methyl]amino}phenoxy)benzoate; |
| Example 53 | 8-{(Z)-[3-(Hydroxymethyl)anilino]methylidene}-6H-[1,3]-thiazolo[5,4-e]indol-7-one; |
| Example 54 | 3-{(Z)-[(7-Oxo-6,7-dihydro-8H-[1,3]thiazolo[5,4-e]indol-8-ylidene)methyl]amino}benzamide; |
| Example 55 | 8-{(Z)-[4-(5-Methyl-3-oxo-2,3-dihydro-1H-pyrazol-1-yl)anilino]methylidene}-6H-[1,3]thiazolo[5,4]indol-7-one; |
| Example 56 | Methyl 4-{(Z)-[(7-Oxo-6,7-dihydro-8H-[1,3]thiazolo-[5,4-e]indol-ylidene)methyl]amino}benzoate; |
| Example 57 | 4-{(Z)-[(7-Oxo-6,7-dihydro-8H-[1,3]thiazolo[5,4-e]indol-8-ylidene)methyl]amino}benzonitrile; |
| Example 58 | N-Methyl-N-(4-{(Z)-[(7-oxo-6,7-dihydro-8H-[1,3]thiazolo-[5,4-e]indol-8-ylidene)methyl]amino}phenyl)acetamide; |
| Example 59 | 1-[(Z)-(4-Phenoxyanilino)methylidene]-1,3-dihydro-2H-pyrrolo-[3,2-f]quinolin-2-one; |
| Example 60 | 1-{(Z)-[4-(Benzyloxy)anilino]methylidene}-1,3-dihydro-2H-pyrrolo[3,2-f]quinolin-2-one; |
| Example 61 | Methyl 4-(4-{(Z)-[(2-Oxo-2,3-dihydro-1H-pyrrolo[3,2-f]-quinolin-1-ylidene)methyl]amino}phenoxy)benzoate; |
| Example 62 | Methyl 3-(4-{(Z)-[(2-Oxo-2,3-dihydro-1H-pyrrolo[3,2-f]-quinolin-1-ylidene)methyl]amino}phenoxy)benzoate; |
| Example 63 | 3-Ethyl-3-(4-{(Z)-[(2-oxo-2,3-dihydro-1H-pyrrolo[3,2-f]-quinolin-1-ylidene)methyl]amino}phenyl)-2,6-piperidinedione; |
| Example 64 | 1-[(Z)-(4-Benzoylanilino)methylidene]-1,3-dihydro-2H-pyrrolo[3,2-f]quinolin-one; |
| Example 65 | 1-{(Z[3-(Hydroxymethyl)anilino]methylidene}-1,3-dihydro-2H-pyrrolo[3,2-f]quinolin-2-one; |
| Example 66 | 1-{(Z[4-(Methyl-3-oxo-2,3-dihydro-1H-pyrazol-1-yl)-anilino]methylidene}-1H-pyrrolo[3,2-f]quinolin-2(3H)-one |
| Example 67 | 1-((EH)-4-[(E)-2-(4-Hydroxyphenyl)ethenyl]anilino}-methylidene)1,3-dihydro-2H-pyrrolo[3,2-f]quinoiin-2-one; |
| Example 68 | 3-{(Z)-[(2-Oxo-2,3-dihydro-1H-pyrroio(3,2-f)quinolin-1-ylidene)methyl]amino}benzamide; |
| Example 69 | 4-{(Z)-[(2-Oxo-2,3-dihydro-1H-pyrrolo[3,2-f]quinolin-1-ylidene)methyl]amino}benzonitrile; |
| Example 70 | Methyl 4-{(Z[(2-oxo-2,3-diihydro-1H-pyrrolo[3,2-f]-quinolin-1-ylidene)methyl]amino}benzoate; |
| Example 71 | 8-[(Z)-(4-{[2-(Diethylamino)ethyl]sulfonyl}anilino)-methylidene]-6H-[1,3]thiazolo[5,4-e]indol-7-one; |
| Example 72 | 1-[(Z)-(4-{[2-(Diethylamino)ethyl]sulfonyl}anilino)-methylidene]-1H-pyrrolo[3,2-f]quinolin-2(3H)-one; |
| Example 73 | 3-{[(Z and E)-(2-Oxo-6-phenyl-1,2-dihydro-3H-indol-3-ylidene)methyl]amino}benzamide; |
| Example 74 | Diethyl 4-{[(Z and E)-(2-oxo-phenyl-1,2-dihydro-3H-indol-3-ylidene)methyl]amino}benzylphosphonate; |
| Example 75 | 3-{[(Z and E)-(2-Oxo-6-phenyl-1,2-dihydro-3H-indol-3-ylidene)methyl]amino}benzonitrile; |
| Example 76 | 3-{(Z and E)-[2-(2-Hydroxyethyl)anilino]methylidene}-6-phenyl-1,3-dihydro-2H-indol-2-one; |
| Example 77 | 3-{(Z and E)-[3-(Hydroxymethyl)anilino]methylidene[-6-phenyl-1,3-dihydro-2H-indol-2-one; |
| Example 78 | 3-[(Z and E)-(2-Methoxyanilino)methylidene]-6-phenyl-1,3-dihydro-2H-indol-2-one; |
| Example 79 | 3-{(Z and E)-[4-(5-Methyl-3-oxo-2,3-dihydro-1H-pyrazol-1-yl)anilino]methylidene}-6-phenyl-1H-indol-2-one; |
| Example 80 | 3-[(Z and E)-(4-Iodoanilino)methylidene]-6-phenyl-1H-indol-2-one; |
| Example 81 | 3-({(Z and E)-[6-(2-Furyl)-2-oxo-1,2-dihydro-3H-indol-3-ylidene]methyl}amino)benzamide; |
| Example 82 | Diethyl 4-({(Z and E)-[6-(2-furyl)-2-oxo-1,2-dihydro-3H-indol-3-ylidene]methyl}amino)benzylphosphonate; |
| Example 83 | 3-({(Z and E)-[6-(2-Furyl)-2-oxo-1,2-dihydro-3H-indol-3-ylidene]methyl}amino)benzonitrile; |
| Example 84 | 6-(2-Furyl)-3-{(Z and E)-[2-(2-hydroxyethyl)anilino]-methylidene}-1,3-dihydro-2H-indol-2-one; |
| Example 85 | 6-(2-Furyl)-3-{(Z and E)-[3-(hydroxymethyl)anilino]-methylidene}-1,3-dihydro-2H-indol-2-one; |
| Example 86 | 6-(2-Furyl)-3-[(Z and E)-(2-methoxyanilino)methylidene]-1,3-dihydro-2H-indol-2-one; |
| Example 87 | 6-(2-Furyl)-3-{(Z and E )-[4-(5-methyl-3-oxo-2,3-dihydro-1H-pyrazol-1-yl)anilino]methylidene)-1H-indol-2-one; |
| Example 88 | 6-(2-Furyl)-3-[(Z and E)-(4-iodoanilino)methylidene]-1H-indol-2-one; |
| Example 89 | 3,6-Dihydro[1,2,3]triazolo[4,5-e]indole-7,8-dione8-[N-(4-methoxyphenyl)hydrazone]; |
| Example 90 | 3,6-Dihydro[1,2,3]triazolo[4,5-e]indole-7,8-dione8-{N-[4-(1,3-oxazol-5-yl)phenyl]hydrazone}; |
| Example 91 | 3,6-Dihydro[1,2,3]triazolo[4,5-e]indole-7,8-dione8-[N-(4-methylphenyl)hydrazone]; |
| Example 92 | 3,6-Dihydro[1,2,3]triazolo[4,5-e]indole-7,8-dione8-(N-{4-[(E)-2-(2-pyridinyl)ethenyl]phenyl}hydrazone); |
| Example 93 | 6H-[1,3]Thiazolo[5,4-e]indole-7,8-dione8-[N-(3-methoxyphenyl)hydrazone]; |
| Example 94 | 5-Hydroxy-4,6-dimethyl-1H-indole-2,3-dione3-[N-(4-methylphenyl)hydrazone]; |
| Example 95 | 3,6-Dihydro[1,2,3]triazolo[4,5-e]indole-7,8-dione8-{N-[4-(trifluoromethyl)phenyl]hydrazone}; |
| Example 96 | 6H-[1,3]Thiazolo[5,4-e]indole-7,8-dione8-[N-(3-fluorophenyl)hydrazone]; |
| Example 97 | 6H-[1,3]Thiazolo[5,4-e]indole-7,8-dione8-[N-(4-fluorophenyl)hydrazone]; |
| Example 98 | 6H-[1,3]Thiazolo[5,4-e]indole-7,8-dione8-[N-(4-bromophenyl)hydrazone]; |
| Example 99 | 3-{[(2-Oxo-5-phenyl-1,2-dihydro-3H-pyrrolo[2,3-b]pyridin-3-ylidene)methyl]amino}benzamide; |
| Example 100 | Diethyl 4-{[(2-Oxo-5-phenyl-1,2-dihydro-3H-pyrrolo-[2,3-b]-pyridin-3-ylidene)methyl]amino}-benzylphosphonate; |
| Example 101 | 3-{[(2-Oxo-5-phenyl-1,2-dihydro-3H-pyrrolo[2,3-b]pyridin-3-ylidene)methyl]amino}benzonitrile; |
| Example 102 | 3-{[2-(2-Hydroxyethyl)anilino]methylidene}-5-phenyl-1,3-dihydro-2H-pyrrolo[2,3-b]pyridin-2-one; |
| Example 103 | 3-{[3-(Hydroxymethyl)anilino]methylidene}-phenyl-1,3-dihydro-2H-pyrrolo[2,3-b]pyridin-2-one; |
| Example 104 | 3-[(2-Methoxyanilino)methylidene]-5-phenyl-1,3-dihydro-2H-pyrrolo[2,3-b]pyridin-2-one; |
| Example 105 | 3-{[4-(5-Methyl-3-oxo-2,3-dihydro-1H-pyrazol-1-yl)-anilino]methylidene}-5-phenyl-1H-pyrrolo[2,3-b]pyridin-2-one; |
| Example 106 | 3-[(4-Iodoanilino)methylidene]-phenyl-1H-pyrrolo[2,3-b]-pyridin-2-one; |
| Example 107 | 3-({[5-(2-Furyl)-2-oxo-1,2-dihydro-3H-pyrrolo[2,3-b]-pyridin-3-ylidene]methyl}amino)benzamide; |
| Example 108 | Diethyl 4-({[5-(2-furyl)-2-oxo-1,2-dihydro-3H-pyrrolo-[2,3-b]-pyridin-3-ylidene]methyl}amino)-benzylphosphonate; |
| Example 109 | 3-({[5-(2-Furyl{2-oxo-1,2-dihydro-3H-pyrrolo[2,3-b]-pyridin-3-ylidene]methyl}amino)benzonitrile: |
| Example 110 | 5-(2-Furyl){3[2-(2-hydroxyethyl)anilino]methylidene{-1,3-dihydro-2H-pyrrolo[2,3-b]pyridin-2-one; |
| Example 111 | 5-(2-Furyl)-3[3-(hydroxymethyl)anilino]methylidene{-1,3-dihydro-2H-pyrrolo(2,3-b)pyridin-2-one; |
| Example 112 | 5-(2-Furyl){3-((2-methoxyanilino)methylidene]-1,3-dihydro-2H-pyrrolo(2,3-b)pyridin-2-one; |
| Example 113 | 5-(2-Furyl){3{[4-(5-methyl-3-oxo-2,3-dihydro-1H-pyrazol-1-yl)anilino]methylidene-1H-pyrrolo[2,3-b]pyridin-2-one; |
| Example 114 | 5-(2-Furyl)-3-[(4-iodoanilino)methylidene]-1H-pyrrolo-[2,3-b]pyridin-2-one; |
| Example 115 | 3-({[2-Oxo-5-(3-thienyl)-1,2-dihydro-3H-pyrrolo[2,3-b]-pyridin-3-ylidene]methyl}amino)benzamide; |

TABLE 4-continued

Example 116 Diethyl 4-({[2-oxo-5-(3-thienyl)-1,2-dihydro-3H-pyrrolo-[2,3-b]pyridin-3-ylidene]methyl}amino)benzylphosphonate;
Example 117 3-({[2-Oxo-5-(3-thienyl)-1,2-dihydro-3H-pyrrolo[2,3-b]-pyridin-3-ylidene]methyl}amino)benzonitrile;
Example 118 3-{[2-(2-Hydroxyethyl)anilino]methylidene}-5-(3-thienyl)-1,3-dihydro-2H-pyrrolo[2,3-b]pyridin-2-one;
Example 119 3-{[3-(Hydroxymethyl)anilino]methylidene}-5-(3-thienyl)-1,3-dihydro-2H-pyrrolo[2,3-b]pyridin-2-one;
Example 120 3-[(2-Methoxyanilino)methylidene]-5-(3-thienyl)-1,3-dihydro-2H-pyrrolo[2,3-b]pyridin-2-one;
Example 121 3-{[4-(5-Methyl-3-oxo-2,3-dihydro-1H-pyrazol-1-yl)anilino]methylidene}-5-(3-thienyl)-1,3-dihydro-2H-pyrrolo[2,3-b]pyridin-2-one;
Example 122 3-[(4-Iodoanilino)methylidene]-5-(3-thienyl)-1H-pyrrolo-[2,3-b]pyridin-2-one;
Example 123 3-{[(5-Bromo-2-oxo-1,2-dihydro-3H-pyrrolo[2,3-b]pyridin-3-ylidene)methyl]amino}benzamide;
Example 124 Diethyl 4-{[(5-Bromo-2-oxo-1,2-dihydro-3H-pyrrolo-[2,3-b]pyridin-3-ylidene)methyl]amino}benzylphosphonate;
Example 125 3-{[(5-Bromo-2-oxo-1,2-dihydro-3H-pyrrolo[2,3-b]pyridin-3-ylidene)methyl]amino}benzonitrile;
Example 126 5-Bromo-3}[2-(2-hydroxyethyl)anilino]methylidene}-1,3--dihydro-2H-pyrrolo[2,3-b]pyridin-2-one;
Example 127 5-Bromo-3[3-(hydroxymethyl)anilino]methylidene}-1,3-dihydro-2H-pyrrolo[2,3-b]pyridin-2-one;
Example 128 5-Bromo-3-[(2-methoxyanilino)methylidene]-1,3-dihydro-2H-pyrrolo[2,3-b]pyridin-2-one;
Example 129 5-Bromo-3-{[4-(5-methyl-4-oxo-2,3-dihydro-1H-pyrazol-1-yl)anilino]methylidene}-1,3-dihydro-2H-pyrrolo[2,3-b]-pyridin-2-one;
Example 130 5-Bromo-3-[(4-iodoanilino)methylidene]1 H-pyrrolo[2,3-b]-pyridin-2-one;
Example 131 3-{[(6-Chloro-2-oxo-1,2-dihydro-3H-pyrrolo[2,3-b]pyridin-3-ylidene)methyl]amino}benzamide;
Example 132 Diethyl 4-{[(6-chloro-2-oxo-1,2-dihydro-3H-pyrrolo[2,3-b]-pyridin-3-ylidene)methyl]amino}benzylphosphonate;
Example 133 3-{[(6-Chloro-2-oxo-1,2-dihydro-3H-pyrrolo[2,3-b]pyridin-3-ylidene)methyl]amino}benzonitrile;
Example 134 6-Chloro-3-{[2-(2-hydroxyethyl)anilino]methylidene}-1,3-dihydro-2H-pyrrolo[2,3-b]pyridin-2-one;
Example 135 6-Chloro-3-{[3-(hydroxymethyl)anilino]methylidene}-1,3-dihydro-2H-pyrrolo[2,3-b]pyridin-2-one;
Example 136 6-Chloro-3-[(2-methoxyanilino)methylidene]1,3-dihydro-2H-pyrrolo[2,3-b]pyridin-2-one;
Example 137 6-Chloro-3-{[4-(5-methyl-3-oxo-2,3-dihydro-1H-pyrazol-1-yl)anilino]methylidene}-1,3-dihydro-2H-pyrrolo[2,3-b]-pyridin-2-one;
Example 138 6-Chloro-3-[(4-iodoanilino)methylidene]1H-pyrrolo[2,3-b]-pyridin-2-one;
Example 139 Ethyl 3[3-(aminocarbonyl)anilino]methylidene}-2-oxo-2,3-dihydro-1H-pyrrolo[2,3-b]pyridin-5-carboxylate;
Example 140 Ethyl 3-({4-[(diethoxyphosphoryl)methyl]anilino-}methylidene{2-oxo-1,2-dihyd ro-3H-pyrrolo[2,3-b]-pyridine-5-carboxylate;
Example 141 Ethyl 3-[(3-cyanoanilino)methylidene]-2-oxo-2,3-dihydro-1H-pyrrolo[2,3-b]pyridine-5-carboxylate;
Example 142 Ethyl 3-{[2-(2-hydroxyethyl)anilino]methylidene}-2-oxo-2,3-dihydro-1H-pyrrolo[2,3-b]pyridine-5-carboxylate;
Example 143 Ethyl 3-{[3-(hydroxymethyl)anilino]methylidene}-2-oxo-2,3-dihydro-1H-pyrrolo[2,3-b]pyridine-5-carboxylate;
Example 144 Ethyl 3-[(2-methoxyaniiino)methylidene]-2-oxo-2,3-dihydro-1H-pyrrolo[2,3-b]pyridine-5-carboxylate;
Example 145 Ethyl 3-{[4-(5-methyl-3-oxo-2,3-dihydro-1H-pyrazol-1-yl)anilino]methylidene}-2-oxo-1,2-dihydro-3H-pyrrolo-[2,3-b]pyridine-5-carboxylate;
Example 144 Ethyl 3-[(4-iodoanilino)methylidene]-2-oxo-1,2-dihydro-3H-pyrrolo[2,3-b]pyridine-5-carboxylate;
Example 147 3-{[(2-Oxo-1,2-dihydro-3H-pyrrolo[2,3-b]pyridin-3-ylidene)methyl]amino}benzamide;
Example 148 Diethyl 4-{[(2-oxo-1,2-dihydro-3H-pyrrolo[2,3-b]pyridin-3-ylidene)methyl]amino}benzylphosphonate;
Example 149 3-{[(2-Oxo-1,2-dihydro-3H-pyrrolo[2,3-b]pyridin-3-ylidene)methyl]amino}benzonitrile;
Example 150 3[2-(2-Hydroxyethyl)anilino]methylidene-1,3-dihydro-2H-pyrrolo[2,3-b]pyridin-2-one;
Example 151 3-{[3-(Hydroxymethyl)anilino]methylidene}1,3-dihydro-2H-pyrrolo[2,3-b]pyridin-2-one;
Example 152 3-[(2-Methoxyanilino)methylidene]-1,3-dihydro-2H-pyrrolo-[2,3-b]pyridin-2-one;

TABLE 4-continued

Example 153 3-{[4-(Methyl-3-oxo-2,3-dihydro-1H-pyrazol-1-yl)anilino]methylidene-1H-pyrrolo[2,3-b]pyridin-2-one;
Example 154 3-[(4-Iodoanilino)methylidene]-1H-pyrrolo[2,3-b]pyridin-2-one;
Example 155 3[(2-Oxo-1,2-dihydro-3H-pyrrolo[3,2-b]pyridin-3-ylidene)methyl]amino}benzamide;
Example 156 Diethyl 4-{[(2-oxo-1,2-dihydro-3H-pyrrolo[3,2-b]pyridin-3-ylidene)methyl]amino}benzylphosphonate;
Example 157 3-{[(2-Oxo-1,2-dihydro-3H-pyrrolo[3,2-b]pyridin-3-ylidene)methyl]amino}benzonitrile;
Example 158 3-{[2-(2-Hydroxyethyl)anilino]methylidene}-1,3-dihydro-2H-pyrrolo[3,2-b]pyridin-2-one;
Example 159 3-{[3-(Hydroxymethyl)anilino]methylidene}-1,3-dihydro-2H-pyrrolo[3,2-b]pyridin-2-one;
Example 160 3-[(2-Methoxyanilino)methylidene]-1,3-dihydro-2H-pyrrolo[3,2-b]pyridin-2-one;
Example 161 3-{[4-(5-Methyl-3-oxo-2,3-dihydro-1H-pyrazol-1-yl)anilino]methylidene}-1H-pyrrolo[3,2-b]pyridin-2-one; and
Example 162 3-[(4-Iodoanilino)methylidene]1H-pyrrolo[3,2-b]pyridin-2-one.
Example 163 3-{(Z and E)-[(Hydroxy-1-naphthyl)amino]methylidene)-5-phenyl-1,3-dihydro-2H-pyrrolo[2,3-b]pyridin-2-one;
Example 164 5-(2-Furyl)-3-{(Z and E )-[(4-hydroxy-1-naphthyl)amino]-methylidene}-1,3-dihydro-2H-pyrrolo[2,3-b]pyridin-2-one;
Example 165 3-{(Z and E)-[(4-Hydroxy-1-naphthyl)amino]methylidene)-(3-thienyl)-1,3-dihydro-2H-pyrrolo[2,3-b]pyridin-2-one;
Example 166 5-Bromo-3-{(Z and E)-[(4-hydroxy-1-naphthyl)amino]-methylidene}-1,3-dihydro-2H-pyrrolo[2,3-b]pyridin-2-one;
Example 167 6-Chloro-3-{(Z and E)-[(4-hydroxy-1-naphthyl)amino]-methylidene)-1,3-dihydro-2H-pyrrolo[2,3-b]pyridin-2-one;
Example 168 Ethyl 3-{(Z and E)-[(4-hydroxy-1-naphthyl)amino]-methylidene}-2-oxo-2,3-dihydro-1H-pyrrolo[2,3-b]pyridin-5-carboxylate;
Example 169 3-{(Z and E)-[(4-Hydroxy-1-naphthyl)amino]methylidene}-1,3-dihydro-2H-pyrrolo[2,3-b]pyridin-2-one;
Example 170 3-{(Z and E)-[(4-Hydroxy-1-naphthyl)amino]methylidene-1,3-dihydro-2H-pyrrolo[3,2b]pyridin-2-one;
Example 171 6-(2-Furyl)-3-{(Z and E)-[(4-hydroxy-1-naphthyl)amino]-methylidene)-1,3-dihydr2H-indol-2-one;
Example 172 3-{(Z and E)-[(4-Hydroxy-1-naphthyl)amino]methylidene}-6-phenyl-1,3-dihydro-2H-indol-2-one;

The invention discloses thirteen different points of substitution on structural formula (I). Each of these points of substitution bears a substituent whose selection and synthesis as part of this invention is independent of all other points of substitution on formula (I). Each point of substitution is now further described.

Preferred substitutions for Y, Z, A and D are nitrogen or carbon. The most preferred substituents for D are nitrogen and carbon. The most highly preferred substituent for Y, Z, A and D is carbon.

Preferred substitutions at the $R^1$ position include hydrogen, fluoro, bromo, iodo, lower alkyl, cyano and nitro. Alternatively, $R^1$ is optionally joined with $R^2$ to form a fused ring structure selected from the group consisting of: thiazole, imidazole, triazole and pyridine. Further, such fused ring structures are optionally substituted by one or more substituents selected from the group consisting of: halogen, amino, lower alkyl substituted amino, lower alkyl and lower alkyl carbonyl. In a preferred embodiment, $R^1$ is selected from the group which includes hydrogen and methyl or $R^1$ is fused with $R^2$ to form a ring structure selected from the group which includes fused thiazole and fused pyridine. In a most highly preferred embodiment, $R^1$ is fused with $R^2$ to form a ring structure selected from the group which includes fused thiazole, pyridine and pyridine substituted by halogen or methyl.

Preferred substitutions at the $R^2$ position include hydrogen, lower alkyl, lower alkoxy, hydroxy lower alkyl, $C_{1-12}$ alkoxycarbonyl, Aryl, Het, aminocarbonyl, lower alkyl aminocarbonyl, halogen and hydroxy. Alternatively, $R^2$ is fused with $R^1$ to form a fused ring selected from the group which includes thiazole, imidazole, triazole and pyridine. Such fused rings are optionally substituted by a substituent selected from the group which includes halogen, amino, lower alkyl substituted amino, lower alkyl and lower alkyl carbonyl. Most preferably, $R^2$ is selected from the group which includes hydroxyl, hydroxy and lower alkyl, or is fused with $R^1$ to form a ring structure selected from the group which includes fused thiazole and fused pyridine. In a most highly preferred embodiment, $R^2$ is selected from the group which includes hydroxy and hydroxymethyl, or is fused with $R^1$ to form a fused ring from the group which includes fused thiazole, pyridine and pyridine substituted by halogen or methyl.

Preferred substitutions at $R^3$ include hydrogen, lower alkyl, lower alkenyl, halogen, phenyl, Het and alkoxy. Most preferred are hydrogen, halogen, ethenyl and methyl. Most highly preferred substitutions at $R^3$ are hydrogen and bromo.

Preferred substitutions at $R^4$ include hydrogen, lower alkyl, hydroxy, hydroxy-lower alkyl, carboxamide, mono-lower alkyl aminocarbonyl, substituted Aryl-lower alkyl, Het, Het-lower alkyl, lower alkoxy, Aryloxy, Het-oxy, amino, mono- or di-lower alkyl-amino lower alkyl aminocarbonyl, mono- or di-lower alkyl-amino lower alkoxycarbonyl, mono- or di-lower alkyl-amino lower alkyl aminocarbonylamino, mono- or di-lower alkyl-amino lower alkoxycarbonylamino, lower alkyl carbonylamino, (lower alkyl carbonyl)(lower alkyl)amino, mono- or di-lower alkyl-amino lower alkyl carbonylamino, [mono- or di-lower alkyl-amino lower alkyl carbonyl][lower alkyl]amino, mono- or di-lower alkyl-amino lower alkyl sulfonylamino, [mono- or di-lower alkyl-amino lower alkyl sulfonyl][lower alkyl] amino, mono- or di-lower alkyl-amino lower alkyl sulfonyl, Het lower alkyl aminocarbonyl, Het lower alkyl aminocarbonylamino, Het lower alkoxycarbonylamino, Het lower alkyl carbonyl, Het lower alkoxycarbonyl, lower alkyl sulfonyl lower alkyl aminoalkyl, lower alkyl sulfonyl-lower alkyl-aminoalkyl-Het-, lower alkoxycarbonyl, halogen, cyano, diethoxyphosphorylmethyl, trifluromethyl and trifluoromethoxy. The most preferred substitutions are lower alkyl, hydroxy, hydroxy-lower alkyl, carboxamide, mono-lower alkyl aminocarbonyl, substituted Aryl-lower alkyl, Het, Het-lower alkyl, Het-oxy, mono- or di-lower alkyl-amino lower alkyl aminocarbonyl, mono- or di-lower alkyl-amino lower alkoxycarbonyl, mono- or di-lower alkyl-amino lower alkyl aminocarbonylamino, mono- or di-lower alkyl-amino lower alkoxycarbonylamino, lower alkyl carbonylamino, (lower alkyl carbonyl)(lower alkyl)amino, mono- or di-lower alkyl-amino lower alkyl carbonylamino, [mono- or di-lower alkyl-amino lower alkyl carbonyl][lower alkyl]amino, mono- or di-lower alkyl-amino lower alkyl sulfonylamino, [mono- or di-lower alkyl-amino lower alkyl sulfonyl][lower alkyl]amino, mono- or di-lower alkyl-amino lower alkyl sulfonyl, Het lower alkyl aminocarbonyl, Het lower alkyl carbonyl, lower alkyl sulfonyl lower alkyl aminoalkyl, lower alkyl sulfonyl-lower alkyl-aminoalkyl-Het-, halogen, cyano and trifluromethyl. Most highly preferred are hydroxymethyl, hydroxyethyl, 4-pyridylmethyl, 4-morpholino, acetamido, N-methylacetamido, carboxamide, diethylaminoethylsulfonyl, 5-methyl-3-pyrazolon-1-yl and 3-ethyl-piperidine-2,6-dion-3-yl.

Preferred substitutions at $R^5$ include hydrogen, lower alkyl, hydroxy, hydroxy-lower alkyl, carboxamide, mono-lower alkyl aminocarbonyl, substituted Aryl-lower alkyl, Het, Het-lower alkyl, lower alkoxy, Aryloxy, Het-oxy, amino, mono- or di-lower alkyl-amino lower alkyl aminocarbonyl, mono- or di-lower alkyl-amino lower alkoxycarbonyl, mono- or di-lower alkyl-amino lower alkyl aminocarbonylamino, mono- or di-lower alkyl-amino lower alkoxycarbonylamino, lower alkyl carbonylamino, (lower alkyl carbonyl)(lower alkyl)amino, mono- or di-lower alkyl-amino lower alkyl carbonylamino, [mono- or di-lower alkyl-amino lower alkyl carbonyl][lower alkyl]amino, mono- or di-lower alkyl-amino lower alkyl sulfonylamino, [mono- or di-lower alkyl-amino lower alkyl sulfonyl][lower alkyl]amino, mono- or di-lower alkyl-amino lower alkyl sulfonyl, Het lower alkyl aminocarbonyl, Het lower alkyl carbonyl, lower alkyl sulfonyl lower alkyl aminoalkyl, lower alkyl sulfonyl-lower alkyl-aminoalkyl-Het-, halogen, cyano and trifluromethyl. Most highly preferred are hydroxymethyl, hydroxyethyl, 4-pyridylmethyl, 4-morpholino, acetamido, N-methylacetamido, carboxamide, diethylaminoethylsulfonyl, 5-methyl-3-pyrazolon-1-yl and 3-ethyl-piperidine-2,6-dion-3-yl.

The most preferred substitution at $R^6$ is hydrogen.

Preferred substitutions at $R^7$ and $R^8$ are hydrogen, halogen and methyl.

Another preferred substitution at $R^7$ includes the state in which $R^7$ is joined to $R^5$ so as to form a fused benzo ring from $R^5$ to $R^7$.

Preferred substitutions at X include N, CH and CCH$_3$. Most preferred is CH.

Preferred individual compounds of the present invention are selected from the group consisting of:

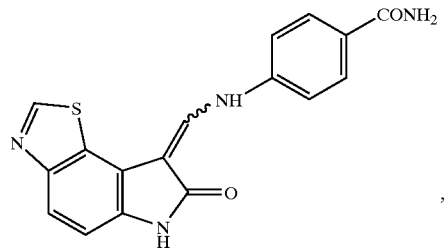

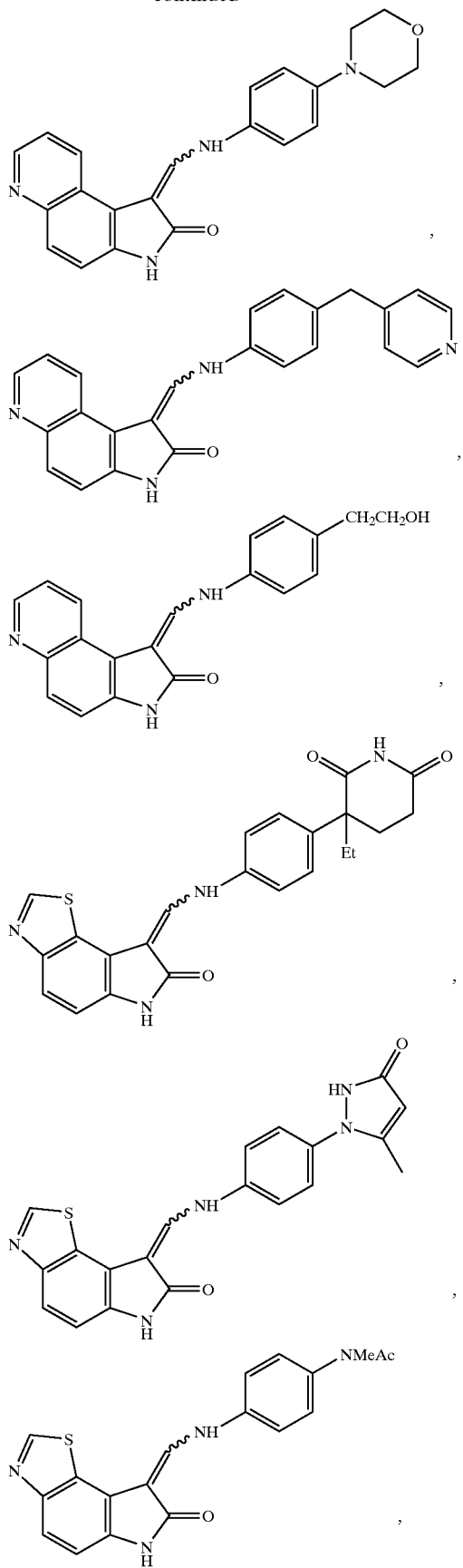
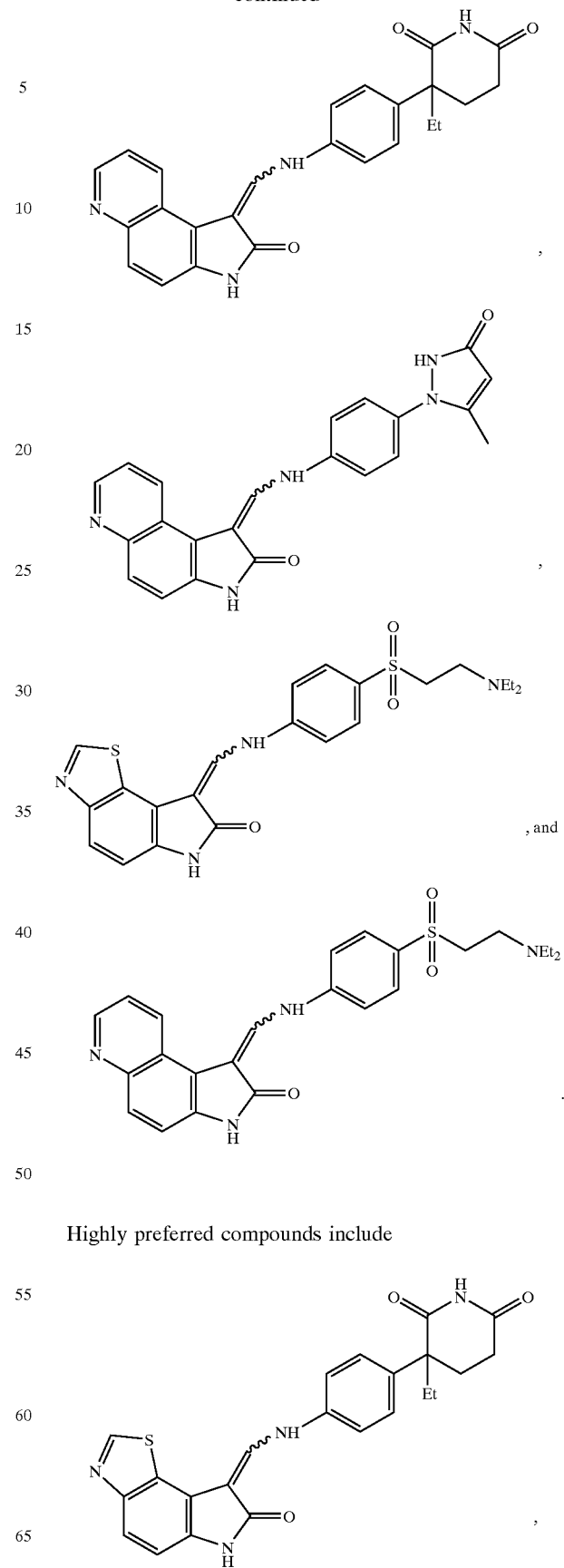
Highly preferred compounds include
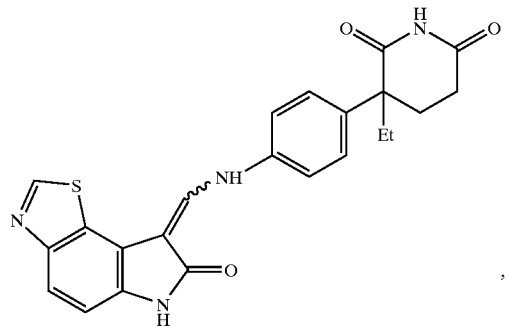

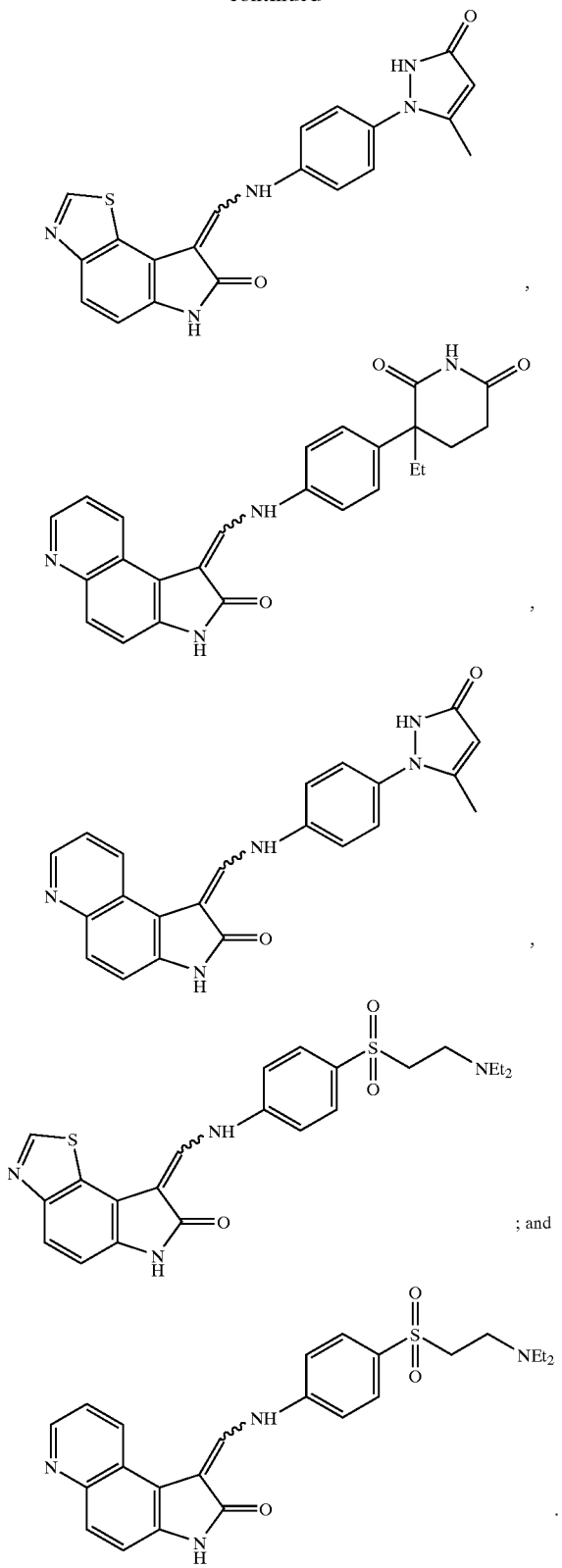

, and

DETAILED DESCRIPTION OF THE INVENTION

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Diethanolamine, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Metaphosphoric, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Trifluoroacetate, Triethiodide, Trimethylammonium and Valerate.

Other salts which are not pharmaceutically acceptable may be useful in the preparation of compounds of formula (I) and these form a further aspect of the invention.

Also included within the scope of the invention are the individual isomers of the compounds represented by formula (I) above as well as any wholly or partially equilibrated mixtures thereof. The present invention also covers the individual isomers of the compounds represented by formula above as mixtures with isomers thereof in which one or more chiral asymmetric centers are inverted.

As used herein, the term "aliphatic" refers to the terms alkyl, alkylene, alkenyl, alkenylene, alkynyl and alkynylene.

As used herein, the term "lower" refers to a group having between one and six carbons.

As used herein, the term "alkyl" refers to a straight or branched chain hydrocarbon having from one to twelve carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by a substituent selected from the group inluding alkyl, nitro, cyano, halogen and lower perfluoroalkyl, multiple degrees of substitution being allowed. Examples of "alkyl" as used herein include, but are not limited to, n-butyl, n-pentyl, isobutyl, isopropyl and the like.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed.

As used herein, the term "alkenylene" refers to an straight or branched chain divalent hydrocarbon radical having from two to ten carbon atoms and one or more carbon - carbon double bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkynylene" as used herein include, but are not limited to, ethyne-1,2-diyl, propyne-1,3-diyl, and the like.

As used herein, the term "cycloaliphatic" includes the terms cycloalkyl, cycloalkylene, cycloalkenyl, cycloalkenylene, cycloalkynyl and cycloalkylnylene.

As used herein, "cycloalkyl" refers to a alicyclic hydrocarbon group with one or more degrees of unsaturation, having from three to twelve carton atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. "Cycloalkyl" includes by way of Example cyclopropyl, cyclobutyl, cyclopentyl, cyclohexyl, cycloheptyl, cyclooctyl, and the like.

As used herein, the term "cycloalkylene" refers to a non-aromatic alicyclic divalent hydrocarbon radical having from three to twelve carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heteroatom ring system" refers to the terms heterocyclic, heterocyclyl, heteroaryl and heteroarylene. Non-limiting examples of such heteroatom ring systems are recited in the Summary of the Invention, above.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings to form ring systems such as anthracene, phenanthrene and napthalene, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of aryl include, but are not limited to, phenyl, 2-naphthyl, 1-naphthyl, biphenyl, and the like.

As used herein, the term "arylene" refers to a benzene ring diradical or to a benzene ring system diradical fused to one or more optionally substituted benzene rings, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms at any position, where N-oxides and sulfur monoxides and sulfur dioxides are permissible heteroaromatic substitutions, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5diyl, 1,3-thiazole-2,4-diyl, 1,3-thiazole-2,5diyl, pyridine-2,4-diyl, pyridine-2,3diyl, pyridine-2,5-diyl, pyrimidine-2,4-diyl, quinoline-2,3-diyl, and the like.

As used herein, the term "alkoxy" refers to the group $R_aO-$, where $R_a$ is aliphatic.

As used herein, the term "alkylsulfanyl" refers to the group $R_aS-$, where $R_a$ is aliphatic.

As used herein, the term "alkylsulfenyl" refers to the group $R_aS(O)-$, where $R_a$ is aliphatic.

As used herein, the term "alkylsulfonyl" refers to the group $R_aSO_2-$, where $R_a$ is aliphatic.

As used herein, the term "acyl" refers to the group $R_aC(O)-$, where $R_a$ is aliphatic, cycloaliphatic, or heterocyclyl.

As used herein, the term "aroyl" refers to the group $R_aC(O)-$, where $R_a$ is aryl.

As used herein, the term "heteroaroyl" refers to the group $R_aC(O)-$, where $R_a$ is heteroaryl.

As used herein, the term "alkoxycarbonyl" refers to the group $R_aOC(O)-$, where $R_a$ is aliphatic.

As used herein, the term "acyloxy" refers to the group $R_aC(O)O-$, where $R_a$ is aliphatic, cycloaliphatic, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" is inclusive of circumstances in which described condition is present and circumstances in which the described condition is not present, for example, where the term is used with reference to a chemical substituent, it indicates the inclusion of embodiments in which the specified substituent is present as well as embodiments in which the specified substituent is not present.

As used herein, the term "substituted" indicates the presence of the named substituent or substituents, and includes multiple degrees of substitution.

As used herein, the terms "contain" or "containing" with reference to alkyl, alkenyl, alkynyl or cycloalkyl substituents indicates in-line substitution(s) with one or more substituents at any position along the alkyl, alkenyl, alkynyl or cycloalkyl substituents, such as one or more of any of O, S, SO, $SO_2$, N, or N-alkyl, including, for example, $-CH_2-O-CH_2-$, $-CH_2-SO_2-CH_2-$, $-CH_2-NH-CH_3$ and so forth.

As used herein, the term "solvate" is a complex of variable stoichiometry formed by a solute (in this invention, a compound of formula (I)) and a solvent. Such solvents for the purpose of the invention may not interfere with the biological activity of the solute. Solvents may be, by way of example, water, ethanol, or acetic acid.

The compounds of the present invention have the ability to crystallize in more than one form, a characteristic which is known as polymorphism, and such polymorphic forms ("polymorphs") are within the scope of the present invention. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the terms "biohydrolyzable carbonate", "biohydrolyzable ureide" and "biohydrolyzable carbamate" include carbonates, ureides, and carbamates, respectively, of a compound of the general formula (I) which carbonates, ureides, and carbamates, do not completely diminish the biological activity of the parent substance. Such carbonates, ureides, and carbamates may confer on the parent compound of the general formula (I) advantageous properties in vivo, such as improved duration of action, onset of action, and the like. Also included are compounds which are relatively biologically inactive but which are converted in vivo by the subject to the biologically active principle. An advantage of such biohydrolyzable forms is that, for example, they facilitate improved oral administration because the carbonates, ureides, and carbamates are more readily absorbed from the gut and are then transformed to a compound of formula (I) in plasma. Many examples of such biohydrolyzable compounds are known in the art and include, by way of example, lower alkyl carbamates.

As used herein, the term "biohydrolyzable ester" is an ester of a compound of general formula which does not completely diminish the biological activity of the parent substance. Such esters may confer on the parent compound of the general formula (I) advantageous properties in vivo, such as improved duration of action, onset of action, and the like. Also included are esters which are relatively biologically inactive but which are converted in vivo by the subject to the biologically active principle. An advantage of such biohydrolyzable forms is that, for example, they facilitate improved oral administration because they are more readily absorbed from the gut and are then transformed to a compound of formula (I) in plasma. Many examples of such biohydrolyzable esters are known in the art and include, by way of example, lower alkyl esters, lower acyloxy-alkyl esters, lower alkoxyacyloxyalkyl esters, alkoxyacyloxy esters, alkyl acylamino alkyl esters and choline esters.

As used herein, the term "biohydrolyzable amide" is an amide of a compound of general formula which does not completely diminish the biological activity of the parent substance. Such amides may confer on the parent compound of the general formula (I) advantageous properties in vivo, such as improved duration of action, onset of action, and the like. Also included are amides which are relatively biologically inactive but which are converted in vivo by the subject to the biologically active principle. An advantage of such biohydrolyzable forms is that, for example, they facilitate improved oral administration because they are more readily absorbed from the gut and are then transformed to a compound of formula (I) in plasma. Many examples of such biohydrolyzable are known in the art and include, by way of example, lower alkyl amides, α-amino acid amides, alkoxyacyl amides and alkylaminoalkylcarbonyl amides.

As used herein, the term "prodrug" includes compounds which are hydrolyzable in vivo to yield an active compound of formula (I), including for example, biohydrolyzable amides, biohydrolyzable esters and biohydrolyzable carbamates. The term "prodrug" also includes compounds in which the biohydrolyzable functionality is encompassed in the compound of formula (I): for example, a lactam formed by a carboxylic group in $R_1$ and an amine in $R_2$, and compounds which may be oxidized or reduced biologically at a given functional group to yield drug substances of formula (I). Examples of such functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" means a group attached to the compound of formula (I) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An Example of an affinity reagent according to b) would be biotin either directly attached to (I) or linked with a spacer of one to 50 atoms selected from the group consisting of: C, H, O, N, S, or P in any combination. An Example of an affinity reagent according to a) above would be fluorescein, either directly attached to (I) or linked with a spacer of one to 50 atoms selected from the group consisting of: C, H, O, N, S, or P in any combination.

The term "effective amount" means that amount of a drug or pharmaceutical agent that will elicit the biological or medical response of a tissue, system, animal or human that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

Whenever the terms "aliphatic" or "aryl" or either of their prefixes appear in a name of a substituent (e.g. arylalkoxyaryloxy) they include those characteristics given above for "aliphatic" and "aryl". Aliphatic or cycloalkyl substituents are term equivalents to those having one or more degrees of unsaturation. Designated numbers of carbon atoms (e.g. $C_{1-10}$) refer independently to the number of carbon atoms in an aliphatic or cyclic aliphatic moiety or to the aliphatic portion of a larger substituent in which the term "aliphatic" appears as a prefix (e.g. "al-").

As used herein, the term "disubstituted amine" or "disubstituted amino-" includes either one or two substitutions on that particular nitrogen atom.

As used herein, the term "oxo" refers to the substituent=O.

As used herein, the term "halogen" or "halo" shall include iodine, bromine, chlorine and fluorine.

As used herein, the term "mercapto" refers to the substituent —SH.

As used herein, the term "carboxy" refers to the substituent —COOH.

As used herein, the term "cyano" refers to the substituent —CN.

As used herein, the term "aminosulfonyl" refer to the substituent —SO$_2$NH$_2$.

As used herein, the term "carbamoyl" refers to the substituent —C(O)NH$_2$.

As used herein, the term "sulfanyl" refers to the substituent —S—.

As used herein, the term "sulfenyl" refers to the substituent —S(O)—.

As used herein, the term "sulfonyl" refers to the substituent —S(O)₂—.

The compounds of formula (I) can be prepared readily according to the following reaction General Synthesis Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

General Synthesis Schemes

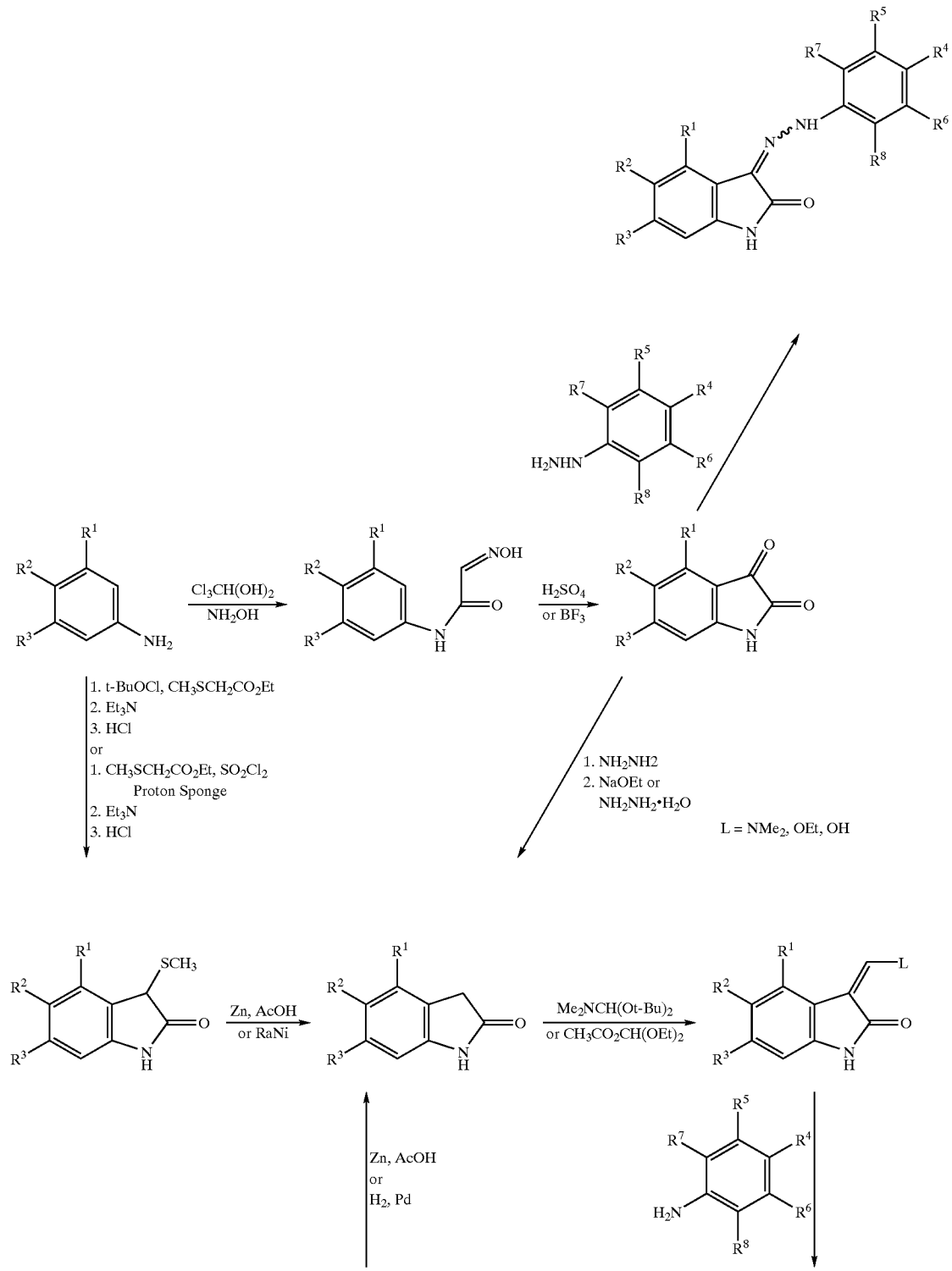

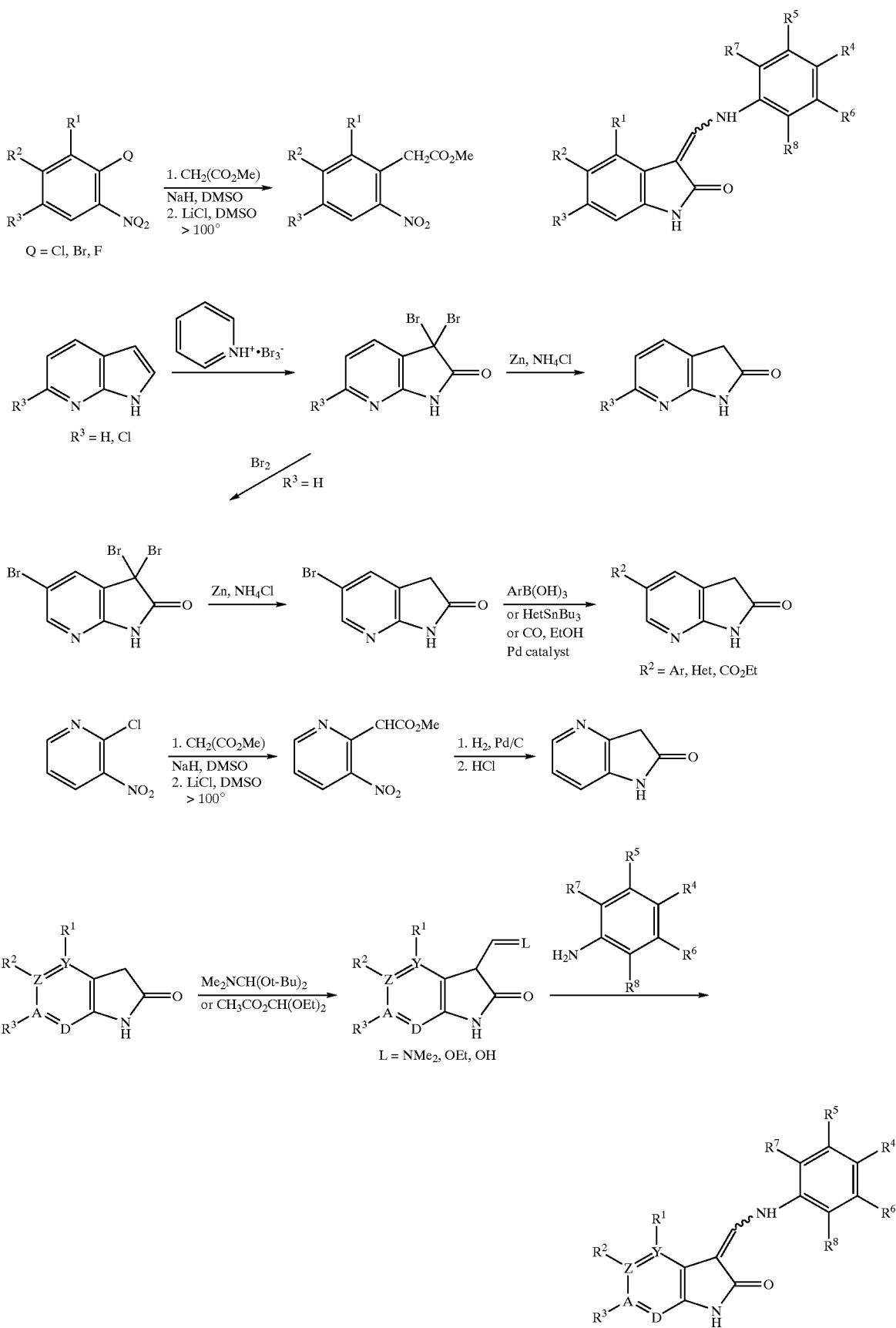

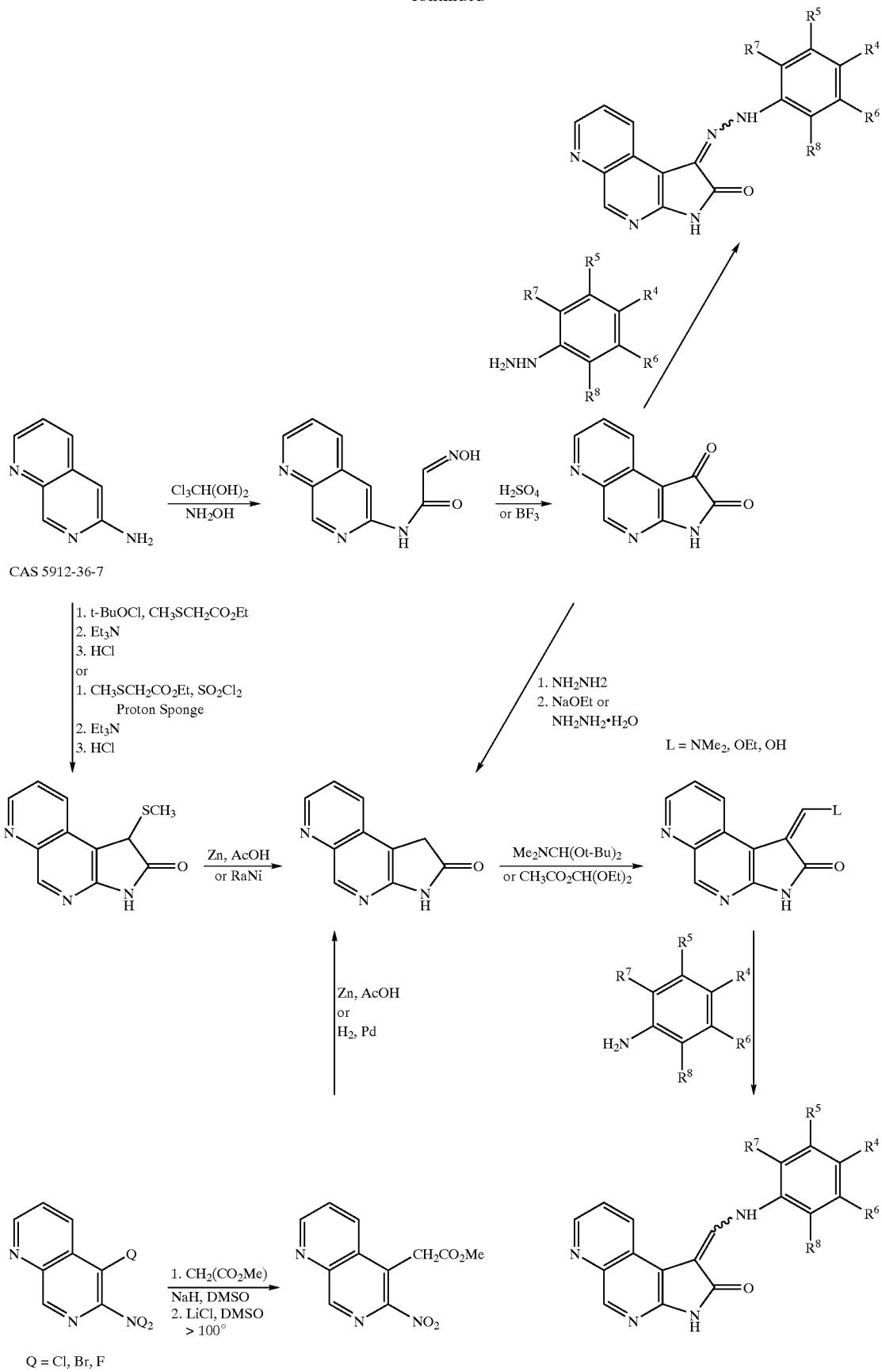

-continued
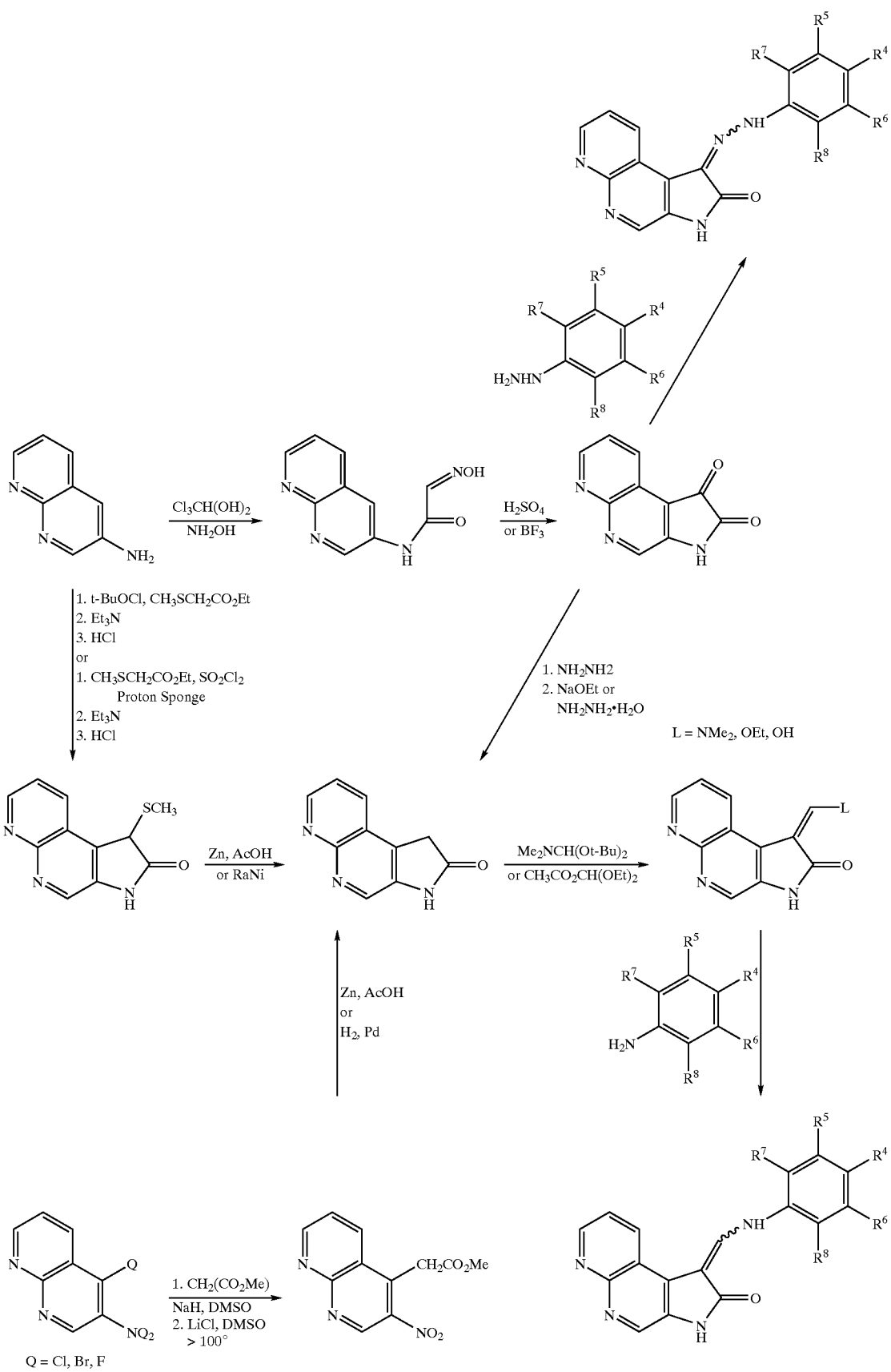

-continued
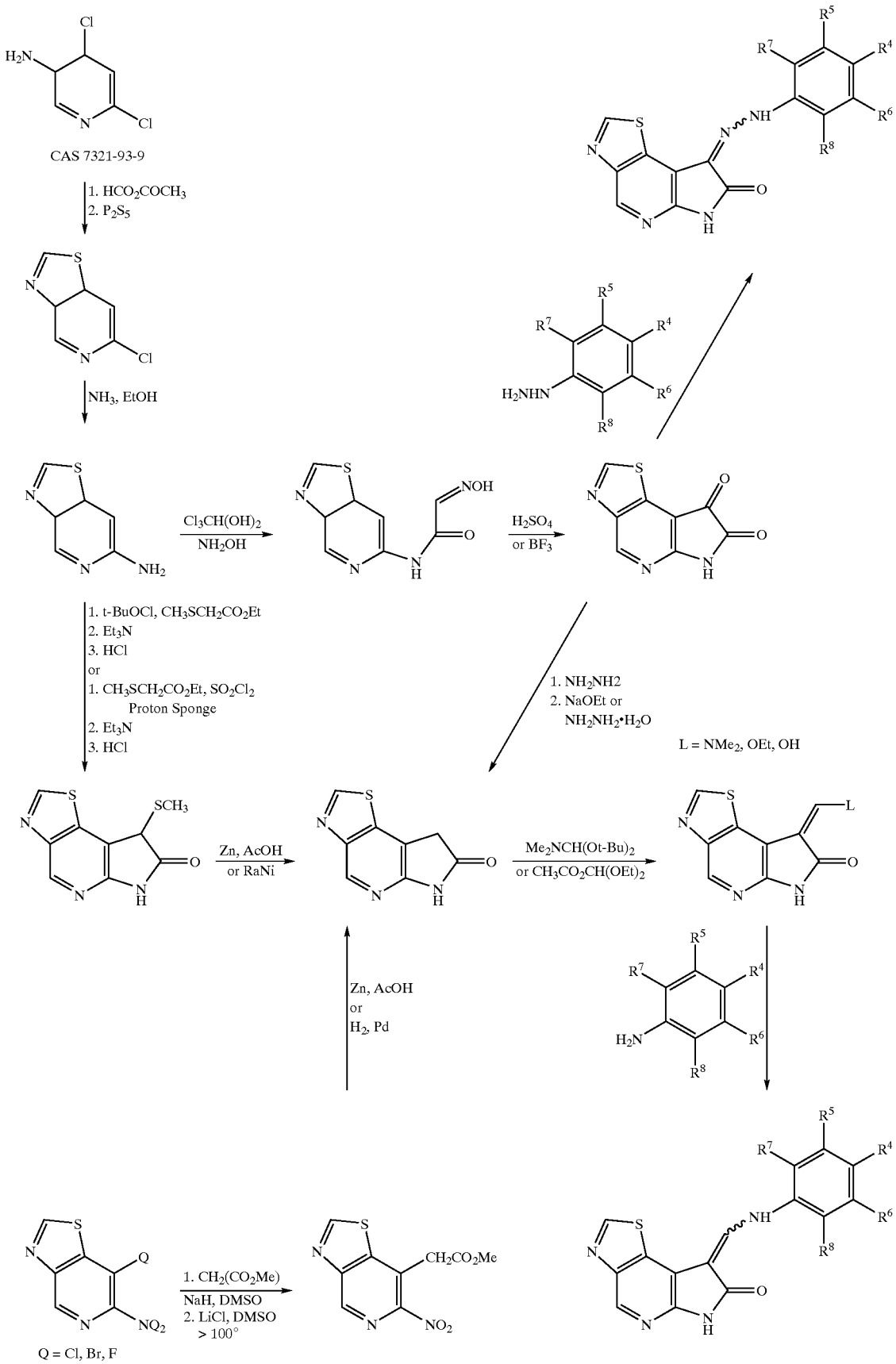

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:

| Abbreviations used in the Examples are as follows: | |
|---|---|
| g = | grams |
| mg = | milligrams |
| L = | liters |
| mL = | milliliters |
| M = | molar |
| N = | normal |
| mM = | millimolar |
| i.v. = | intravenous |
| p.o. = | peroral |
| s.c. = | subcutaneous |
| Hz = | hertz |
| mol = | moles |
| mmol = | millimoles |
| mbar = | millibar |
| psi = | pounds per square inch |
| rt = | room temperature |
| min = | minutes |
| h = | hours |
| mp = | melting point |
| TLC = | thin layer chromatography |
| $R_f$ = | relative TLC mobility |
| MS = | mass spectrometry |
| NMR = | nuclear magnetic resonance spectroscopy |
| APCI = | atmospheric pressure chemical ionization |
| ESI = | electrospray ionization |
| m/z = | mass to charge ratio |
| $t_r$ = | retention time |
| Pd/C = | palladium on activated carbon |
| ether = | diethyl ether |
| MeOH = | methanol |
| EtOAc = | ethyl acetate |
| TEA = | triethylamine |
| DIEA = | diisopropylethylamine |
| THF = | tetrahydrofuran |
| DMF = | N,N-dimethylformamide |
| DMSO = | dimethylsulfoxide |
| DDQ = | 2,3-dichloro-5,6-dicyano-1,4-benzoquinone |
| LAH = | lithium aluminum hydride |
| TFA = | trifluoroacetic acid |
| LDA = | iithium diisopropylamide |
| THP = | tetrahydropyranyl |
| NMM = | N-methylmorpholine-1,4-methylmorpholine |
| HMPA = | hexamethylphosphoric triamide |
| DMPU = | 1,3-dimethypropylene urea |
| d = | days |
| ppm = | parts per million |
| kD = | kiloDalton |
| LPS = | lipopolysaccharide |
| PMA = | phorbol myristate acetate |
| SPA = | scintillation proximity assay |
| EDTA = | ethylenediamine tetraacetic acid |
| FBS = | fetal bovine semm |
| PBS = | phosphate buffered saline solution |
| BrdU = | bromodeoxyuridine |
| BSA = | bovine serum albumin |
| FCS = | fetal calf serum |
| DMEM = | Dulbeccols modified Eagle's medium |
| pfu = | plaque forming units |
| MOI = | multiplicity of infection |

Reagents are commercially available or are prepared according to procedures in the literature. The physical data given for the compounds exemplified is consistent with the assigned structure of those compounds. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

Procedure A—First method for 1H-indol-2,3-dione (isatin) formation: preparation of 6-H-1-thia-3,6-diaza-as-indacen-7,8-dione To a 1-L flask was added a magnetic stir bar, 85 g of sodium sulfate, and 100 mL of water. The mixture was magnetically stirred until all the solids were dissolved. To the resultant aqueous solution was added a solution of 6-aminobenzothiazole (4.96 g, 33.0 mmol) in 50 mL of 1N aqueous hydrochloric acid and 10 mL of ethanol. The mixture was stirred, and chloral (6.0 g, (36 mmol) was added. To the resultant solution was added a solution of hydroxyl amine hydrochloride (7.50 g, 108 mmol) in 30 mL of water. The final mixture was heated with stirring to a gentle boil until all solids dissappeared, and heating was continued for an additional 15 min. The flask was removed from the heat, and the solution was poured onto 500 g of ice. The mixture was stirred as the product precipatated from solution. The precipitate was collected by suction filtration, washed thoroughly with water, filtered, and air dried to provide 6.9 g (94%) of N-benzothiazol-6-yl-2-hydroxyimino-acetamide: $^1$H NMR (DMSO-d$_6$): δ 12.2 (s, 1H), 10.4 (s, 1H), 9.2 (s, 1H), 8.5 (s, 1H), 7.9 (d, 1H), 7.7 (m, 1H), 7.7 (s, 1H); APCI-MS m/z 220 (M–H)$^-$. To a 1-L 3-neck round bottom flask was placed a magnetic stir bar and 100 ml of concentrated sulfuric acid. The flask was fitted with a thermometer to monitor the temperature of the reaction. The sulfuric acid was heated to 100° C., and 10.0 g (45.2 mmol) of N-benzothiazol-6-yl-2-hydroxyimino-acetamide was added slowly. The solution was heated for ~1 h, and the reaction mixture was poured into 750 g of ice and water. The residual reaction mixture in the reaction vessel was washed out with an additional 20 mL of cold water. The aqueous slurry was stirred for about 1 h and filtered. The solid was washed thoroughly with water, filtered, and air dried to yield 4.3 g (46%) of 6-H-1-thia-3,6-diaza-as-indacen-7,8-dione: $^1$H NMR (DMSO-d$_6$): δ 11.1 (s, 1H), 9.2 (s, 1H), 8.2 (d, 1H), 7.0 (d, 1H); APCI-MS m/z 203 (M–H)$^-$.

Procedure B—First method for 1,3-dihydro-indol-2-one (oxindole) formation (Gassman and van Bergen, Journal of the American Chemical Society 1974, 96, 5508–12): preparation of 6.8-dihydro-1-thia-3, 6-diaza-as-indacen-7-one A 2-L three-neck round bottom flask was fitted with an internal thermometer, 250-mL addition funnel, magnetic stir bar and septa. The flask was charged with nitrogen, 200 mL of dry THF, and 6-aminobenzothiazole (15.2 g, 0.100 mol). The mixture was stirred and cooled in a dry ice-acetone bath to an internal temperature of –74° C. A solution of tert-butyl hypoclorite (11.0 g, 0.103 mol) in 50 mL of dichloromethane was added over a 15 min period. The resultant solution was stirred for an additional 3 h at dry ice-acetone bath temperature. To the reaction was then added by slow, dropwise addition a solution of ethyl methylthioacetate (13.8 g, 0.103 mol) in 50 mL of dichoromethane. The resultant solution was stirred for an additional 3 h at dry ice-acetone bath temperature. A solution of triethyl amine (25.3 g, 0.250 mol) and 50 ml of dichloromethane was added at dry ice-acetone bath temperature, and the solution was stirred for 0.5 h. The cooling bath was removed, and the reaction was allowed to warm to rt. The reaction was then concentrated to a thick residue. The thick oil was resuspended in 200 mL of ether and 600 mL of 0.25 M hydrochloric acid. The mixture was allowed to stir for 24 h. The resulting solid was filtered from the mixture and triturated with water and ether. The solid was then resuspended in cold MeOH, filtered and dried under vacum for 16 h to yield 18.7 g (79%) of 8-methylsulfanyl-6,8-dihydro-1-thia-3,6-diaza-as-indacen-7-one: $_1$H NMR (DMSO-d6) δ 10.8 (s, 1H), 9.2 (s, 1H), 8.0 (d, 1H), 7.1 (d, 1H), 1.8 (s, 3H); APCI-MS m/z 235 (M−H)−. To a 500-mL erlenmeyer flask was added a stir bar, 8.1 g (0.034 moles) of 8-methylsulfanyl-6,8-dihydro-1-thio-3,6-diaza-as-indacen-7-one and 100 mL of glacial acetic acid. The mixture was stirred until all the starting material had dissolved. The reaction mixture was then diluted with 100 mL of THF. Zinc metal (16 g, 325 mesh) was then added. The heterogeneous mixture was then stirred and heated to 60° C. for 2.5 h. The mixture was vacuum filtered through a one half inch pad of celite. The residue on the filter pad was washed with additional THF. The filtrates were combined and concentrated to a wet solid. The solid was triturated with MeOH, filtered and air dried to yield 4.51 g (70%) of 6.8-dihydro-1-thia-3,6diaza-as-indacen-7-one as a free-flowing solid: $_1$H NMR (DMSO-d6): δ 10.5 (s, 1H), 9.1 (s, 1H), 7.9 (d, 1H), 7.0 (d, 1H), 3.6 (s, 2H); APCI-MS m/z 191 (M+H)$_+$.

Procedure C—Second method for 1,3-dihydro-indol-2-one (oxindole) formation (Seibert, Chemie Berichte 1947, 80, 494–502): preparation of 3-H-pyrrolo[3,2-f]quinoline-2one via Wolff-Kishner reduction A solution of 2.3 g (12 mmol) of 3-H-pyrrolo[3,2-f]quinoline-1,2-dione (prepared from 6-aminoquinoline according to Procedure A) and 2.0 ml (0.06 mol) of hydrazine in 50 ml of DMF and 50 ml of ethanol was stirred at reflux for 2 h. The resulting suspension was allowed to cool to ambient temperature and was then chilled in an ice bath and filtered. The solid was washed with a small volume of ethanol and allowed to air dry to give 1-hydrazono-1,3-dihydropyrrolo[3,2-f]quinolin-2-one as an orange solid (1.8 g, 73%): $^1$H NMR (DMSO-d$_6$): δ 7.37 (d, J=8.8 Hz, 1H), 7.47 (dd, J=8.4, 4.2 Hz, 1H), 7.81 (d, J=8.8 Hz, 1H), 8.71 (dd, J=4.2, 1.6 Hz, 1H), 8.80 (d, J=8.4 Hz, 1H), 9.90 (br d, J=14.7 Hz, 1H), 10.89 (br d, J=14.7 Hz, 1H), 10.95 (br s, 1H); ESI-MS m/z 213 (M+H)$^+$. A solution 1.8 g (8.5 mmol) of 1-hydrazono-1,3-dihydropyrrolo[3,2-f]quinolin-2-one in 50 ml of freshly prepared 0.5 M sodium ethoxide solution was stirred at reflux for 3 h. The solution was diluted with 50 ml of water, neutralized with acetic acid, and concentrated on a rotary evaporator until cloudy. The solution was stored in a refrigerator overnight. The solid was filtered off, and the filtrate was extracted with three 80-ml portions of EtOAc. A solution of the solid in MeOH/EtOAc was combined with the extracts and passed through a short pad of silica gel, eluting with EtOAc. The solution was then concentrated to a small volume on a rotary evaporator, and the resulting suspension was diluted with an equal volume of ethanol, sonicated, and filtered to give 3-H-pyrrolo[3,2-f]quinoline-2-one as a light green solid (0.52 g, 33%); $^1$H NMR (DMSO$_6$): δ 3.80 (s, 2H), 7.35 (d, J=8.8 Hz, 1H), 7.44 (dd, J=8.4, 4.2 Hz, 1H), 7.88 (d, J=8.8 Hz, 1H), 8.08 (d, J=8.4 Hz, 1H), 8.70 (dd, J=4.2, 1.6 Hz, 1H), 10.57 (br s, 1H); APCI-MS m/z 183 (M−H)−.

Procedure D—Third method for 1,3-dihydro-indol-2-one (oxindole) formation (Quallich and Morrissey, Synthesis, 1993, 51–53): preparation of 6-bromooxindole Sodium hydride (60% oil dispersion, 4.00 g, 100 mmol) was added to a dry 500 ml flask under nitrogen and washed with three 25 ml portions of hexanes. Anhydrous DMSO (100 ml) was added, followed by dimethyl malonate (11.4 ml, 100 mmol). The reaction was heated briefly to 100° C. with stirring, then cooled to room temperature. 2,5-Dibromonitrobenzene (12.9 g, 46.0 mmol) was added and the reaction was heated at 110° C. for 2 hrs. After cooling to room temperature, the solution was added in portions to 300 ml of saturated aqueous ammonium chloride with 150 ml of 1:1 hexanes/ethyl acetate. The organic layer was washed with 300 ml of saturated aqueous ammonium chloride, four 200 ml portions of water, and 200 ml of saturated aqueous sodium chloride. The organic layer was dried over magnesium sulfate and the solvent was evaporated to give 13.6 g of crude dimethyl 2-(4-bromo-2-nitrophenyl)malonate as a brown oil. This material (30–40 mmol) was heated to 110° C. in 250 ml DMSO with 3.6 g (84 mmol) of lithium chloride and 750 mg (42 mmol) of water for 4.5 hrs. The reaction was cooled to room temperature and added to 300 ml of ethyl acetate with 300 ml of saturated aqueous sodium chloride. The organic layer was washed with a second portion of 300 ml saturated aqueous sodium chloride, dried over magnesium sulfate, and the solvent was removed to give 11.1 g brown oil. This material was adsorbed on 40 g of silica gel and applied to a column containing another 80 g of silica gel. Elution with 0–10% ethyl acetate in hexanes gave 3.53 g (28% from 2,5-dibromonitrobenzene) of methyl (4-bromo-2-nitrophenyl) acetate as a yellow solid.

This material (3.53 g, 12.8 mmol) was dissolved in ethanol (80 ml) with 50 ml of 50% sulfuric acid and heated to reflux with stirring. Zinc powder (3.40 g, 52 mmol) was added in portions over 1 hr. Heating was continued for another 2 hrs and the reflux condenser was removed to allow ethanol to evaporate from the hot reaction under a stream of nitrogen. The reaction mixture was filtered through celite, washing with 100 ml of ethyl acetate. The water layer was separated from the filtrate and extracted with 100 ml of ethyl acetate. Combined ethyl acetate layers were washed with 30 ml of saturated aqueous sodium bicarbonate and 30 ml of saturated aqueous sodium chloride and dried over magnesium sulfate. Evaporation of solvent gave 1.6 g of crude product which was purified by chromatography on 25 g of silica gel with 10–40% ethyl acetate/hexanes to give 0.85 g (31%) of 6-bromooxindole as an off-white solid.

Procedure E—Method for dimethylaminomethinyloxindole formation: preparation of 8-dimethylamino-methylene-6,8-dihydro-1-thia-3,6-diaza-as-indacen-7-one To a suspension of 1.0 g (5.3 mmol) of 6,8-dihydro-1-thia-3,6-diaza-as-indacen-7-one (Procedure B) in 7.5 mL of DMF was added 1.38 g (6.80 mmol) of N,N-dimethylformamide-di-t-butyl acetal. The mixture was stirred at ambient temperature for 1 h and diluted with 7.5 mL of Et$_2$O. The resulting precipitate was isolated filtration to afford 8-dimethylamino-methylene-6,8-dihydro-1-thia-3,6-diaza-as-indacen-7-one as a tan solid (1.0 g, 77%): $^1$H NMR (DMSO-d$_6$): δ3.33 (bs, 3H), 3.59 (bs, 3H), 6.97 (d, J=8.4, 1H), 7.33 (s, 1H), 7.62 (d, J=8.4, 1H), 9.13 (s,1H), 10.29 (s, 1H); APCI-MS: m/z 246 (M+H)$^+$.

Procedure F—Method for ethoxymethinyloxindole formation: preparation of 8-ethoxymethylene-6,8-dihydro-1-thia-3,6-diaza-as-indacen-7-one To a 250-ml round bottom flask was added a stir bar, 6,8-dihydro-1-thia-3,6-diaza-as-indacen-7-one (Procedure B, 4.0 g, 0.021 mol), 40 mL of glacial acetic and diethoxymethyl acetate (17.0 g, 0.105 moles). The flask was fitted with a reflux condenser and charged with nitrogen. The reaction was heated to reflux for 8 h. The flask was cooled, the stir bar was removed and the reaction was concentrated to a wet solid. The solid was triturated with a solution of ether and ethanol. The mixture was filtered, the solid was washed with an ethanol-ether solution, and the solid was dried under vacuum to yield 8-ethoxymethylene-6,8-dihydro-1-thia-3,6-diaza-as-indacen-7-one: $^1$H NMR (DMSO-$d_6$): δ 10.5 (s, 1H), 9.1 (s, 1H), 7.8 (d, 1H), 7.7 (s, 1H), 7.0 (d, 1H), 4.5 (q, 2H), 1.4 (t, 3H); APCI-MS m/z 245 (M–H)$^-$.

Procedure G—Method for vinylogous urea formation: preparation of N-methyl-N-(4-{(Z)-[(7-oxo-6,7-dihydro-8H-[1,3]thiazolo[5,4-e]indol-8-ylidene)methyl]amino}phenyl)acetamide (Example 58)

A mixture of 8-dimethylamino-methylene-6,8-dihydro-1-thia-3,6-diaza-as-indacen-7-one (Procedure E, 0.040 g, 0.163 mmol) or 8-ethoxymethylene-6,8-dihydro-1-thia-3,6-diaza-as-indacen-7-one (Procedure F, 0.163 mmol), 4-amino-N-methylacetanilide (0.040 g, 0.244 mmol) in absolute ethanol (5 ml) was heated with stirring at 90° C. for 16 h. The reaction was diluted with ethanol and diethyl ether and the product collected by filtration to yield 0.038 g (64%) of the title compound. $^1$H NMR (DMSO-$d_6$): δ 11.03 (d, 1H, J=12.3 Hz), 10.84 (s, 1H), 9.23 (s, 1H), 8.02 (d, 1H, J=12.3 Hz), 7.78 (d, 1H, J=8.4 Hz), 7.48 (d,2H, J=8.2 Hz), 7.35 (d,2H, J=8.2 Hz), 7.09 (d, 1H, J=8.4 Hz), 3 .11 (s,3H), 1.76 (s, 3H); ES-MS m/z 363 (M–H).

Procedure H—Method for condensation of a phenylhydrazine with an isatin to form hydrazones: preparation of 3,6-dihydro[1,2,3]triazolo[4,5-e]indole-7,8-dione 8-[N-(4-methoxyphenyl)hydrazone] (Example 89) 3,6-Dihydro[1,2,3]triazolo[4,5-e]indole-7,8-dione was prepared from 5-aminobenzotrazole according to Procedure A in 6% yield: $^1$H NMR (DMSO-$d_6$): δ 7.04 (d, J=8.4 Hz, 1H), 7.97 (d, J=2.2 Hz, 1H), 8.01 (dd, J=2.2, 8.4 Hz, 1H), 8.20 (s, 1H), 9.26 (s, 1H), 11.19 (bs, 1H); APCI-MS m/z 215 (M+1)$^+$. 3,6-Dihydro[1,2,3]triazolo[4,5-e]indole-7,8-dione (47 mg, 0.25 mmol) was combined with 4-methoxyphenylhydrazine hydrochloride (52 mg, 0.3 mmol) in 2 ml of ethanol and heated at 70° C. for 3 hrs. The product was collected by filtration of the hot solution, washing with ethanol and diethyl ether, to give 39 mg (50%) of the title compound as a dark red solid. NMR showed ~1:1 Z/E mixture. $^1$H NMR (DMSO-$d_6$): 67 3.80 (s, 3H); 7.0 (m, 3H); 7.24 (d, J=8.7 Hz, 0.5H); 7.41 (d, J=8.8 Hz, 0.5H); 7.78 (m, 1.5H); 7.98 (d, J=8.5 Hz, 0.5H); 10.8 (s, 0.5H); 11.3 (s, 0.5H); 12.85 (s, 0.5H); 12.95 (s, 0.5H). APCI-MS m/z 307 (M–1) Procedure I—Method for palladium catalyzed coupling of 6-bromooxindole with alkenyl and aromatic tin reagents: preparation of 6-vinyl oxindole To a mixture of 6-bromooxindole (Procedure D, 0.50 g, 2.4 mmol), vinyltributylstannane (0.95 g, 3.0 mmol), lithium chloride (0.03 g, 7.1 mmol), 2,6-di-tert-butyl-4-methylphenol (0.01 g, 0.05 mmol) in acetonitrile (25 ml) stirring at 80° C. was added dichlorobis(triphenylphosphine) palladium (II). The resulting reaction was stirred with heating for 16 h. The reaction was poured into a vigorously stirring mixture of 5M potassium fluoride solution: ethyl acetate/1:1 (250 mL) and stirred for 0.75 h. The resulting biphasic mixture was filtered through a Celite 521 pad and the pad flushed with ethyl acetate (5×200 mL). The combined organic phases were washed with water (200 mL), saturated sodium chloride (200 mL) and filtered through Whatman PS 1 paper and evaporated in vacuo to a golden yellow syrup. The syrup was titurated with diethyl ether to yield several crops of tan solid. Pure samples were combined, slurried with diethyl ether, filtered, and air dried to yield 0.12 g (31%) of 6-vinyloxindole: $^1$H NMR (DMSO-$d_6$): 67 10.36 (s,1H), 7.13 (d, 1H, J=7.7 Hz), 6.98 (d, 1H, J=7.5 Hz), 6.66 (dd,1H, J=10.9, 17.7 Hz), 5.70 (d, 1H, J=17.6 Hz), 5.18 (d, 1H, J=10.9 Hz), 3.42 (s,2H).

EXAMPLE 1

6-Bromo-3-{(Z and E)-[4-(4-morpholinyl)anilino]methylidene}-1,3-dihydro-2H-indol-2-one Prepared from the dimethylaminomethylene derivative (Procedure E) of 6-bromo-oxindole (procedure D) and 4-(4-morpholino)aniline according to Procedure G in 87% yield to give ~4:1 isomer mixture. Principal isomer: $^1$H NMR (DMSO-$d_6$): δ 10.67 (d, 1H, J=12.5 Hz), 10.56 (s, 1H), 8.57 (d, 1H, J=12.8 Hz), 7.48 (d, 1H, J=7.9 Hz), 7.35–7.29 (m,2H), 7.11 –7.04 (m, 3H), 6.93 (s, 1H), 3.76 (s, 4H), 3.15 (s, 4H); ES-MS m/z 400, 402 (M+1) .

EXAMPLE 2

6-Bromo-3-{(Z and E)-[4-(4-pyridinylmethyl)anilino]methylidene}-1,3-dihydro-2H-indol-2-one Prepared according to Example 1 in 26% yield to give ~9:1 isomer mixture. Principal isomer: $^1$H NMR (DMSO-$d_6$): δ 10.72 (d, 1H, J=12.6 Hz), 10.65 (s, 1H), 8.66 (d, 1H, J=12.8 Hz), 8.48 (d, 1H, J=5.9 Hz), 7.55 (d, 1H, 8.1 Hz), 7.40–7.27 (m, 6H), 7.12 (dd, 1H, J=1.8, 8.1 Hz), 6.99 (d, 1H, J=1.8 Hz), 3.97 (s, 2H); APCI-MS m/s 404, 406 (M–1).

Example 3

8-[(Z and E)-4-Toluidinomethylidene]-6,8-dihydroimidazo[4,5-e]indol-7(3H)-one.

Sodium hydride (7.2 g, 60% in mineral oil, 0.18 mol) was added in portions over 30 min to a stirred solution of 5-aminobenzimidazole (15.0 g, 0.105 mol) in dry DMF (100 mL) and the mixture was stirred at room temperature for 30 min. The reaction mixture was cooled to 0° C. and a solution of di-tert-butyl dicarbonate (24.0 g, 0.110 mol) in dry DMF (25 mL) was added over 10 min. The reaction mixture was stirred at room temperature for 18 h. The solvent was evaporated under reduced pressure and the residue was partitioned between water (200 mL) and diethyl ether (200 mL). The organic phase was separated and the aqueous layer was extracted with diethyl ether. The combined organic extracts were washed with water and brine and dried over anhydrous magnesium sulfate. The drynig agent was removed by filtration through a pad of silica gel and the filtrate evaporated to give a mixture of 5- and 6-amino-1-tert-butoxycarbonylbenzimidazole, 21.5 g (84%). H$^1$ NMR (DMSO-$d_6$): δ 8.40 (s, 1H), 8.23 (s, 1H), 7.55 (d, 1H, J=8.8 Hz), 7.34 (d, 1H, J=8.4 Hz), 7.13 (d, 1H, J=1.6 Hz), 6.83 (d, 1H, J=2 Hz), 6.68 (dd, 1H, J=8.8, 1.6 Hz), 6.60 (dd, 1H, J=8.4, 2 Hz), 1.61 (s, 9H), 1.60 (s, 9H).

To a cold (−78° C.) solution of ethyl methylthioacetate (11.87 g, 88 mmol) in dry dichloromethane (300 mL) was added, dropwise, sulfuryl chloride (7.1 mL, 11.93 g, 88 mmol) over 5 min. The solution was stirred for 30 min and then a solution of a mixture of 5- and 6-amino-1-tert-butoxycarbonylbenzimidazole (21.5 g, 88 mmol) and Proton Sponge (18.9 g, 88 mmol) in dry dichloromethane (150 mL) was added dropwise over 30 min. The mixture was stirred at ñ78° C. for about 1 h and then triethylamine (12.3 mL, 8.94 g, 88 mmol) was added dropwise and the mixture was allowed to warm to room temperature over 18 h. The reaction mixture was washed with water (3×100 mL) and brine and then the organic phase was dried over anhydrous magnesium sulfate. The drying agent was removed by filtration through a pad of silica gel and the filtrate evaporated. The residue was triturated with a small amount of diethyl ether and the resulting solid was collected by filtration. The filtrate was stirred with 2N aqueous HCl (10 mL) for 18 h to yield further white solid which was collected by filtration. The combined white solids were dried under vacuum to give a mixture of 1 and 3-tert-butoxycarbonyl-8-methylthio-7-oxo-7,8-dihydropyrrolo[2,3-g]benzimidazole, 8.74 g (30%). $H^1$ NMR (DMSO-$d_6$): δ 10.882 (s, 1H), 10.72 (s, 1H), 9.41 (s, 1H), 8.52 (s, 1H), 7.45 (d, 1H, J=8.4 Hz), 7.65 (d, 1H, J=8.4 Hz), 7.11 (d, 1H, J=8.4 Hz), 7.93 (d, 1H, J=8.4 Hz), 4.84 9s, 1H), 4.67 (s, 1H), 1.93 (s, 3H), 1.81 (s, 3H), 1.66 (s, 9H).

A solution of a mixture of 1 and 3-tert-butoxycarbonyl-8 methylthio-7-oxo-7,8-dihydropyrrolo[2,3-g]benzimidazole (2.0 g, 6 mmol) in THF (50 mL) was stirred at room temperature and a saturated aqueous solution of ammonium chloride (50 mL) was added. Activated zinc dust (8.0 g) was added and the resulting mixture was stirred vigorously for about 18 h. The solids were removed by filtration through a pad of Celite and the organic layer was separated. The organic phase was dried over anhydrous magnesium sulfate, filtered and the solvent evaporated under reduced pressure to leave a yellow solid. Trituration with a small amount of solid gave a pale solid which was collected by filtration and dried under vacuum to give a mixture of 1 and 3-tert-butoxycarbonyl-7-oxo-7,8-dihydropyrrolo[2,3-g]benzimidazole, 1.32 g (77%). $H^1$ NMR (DMSO-$d_6$): δ 10.51 (br s, 1H), 10.21 (br s, 1H), 8.46 (s, 1 h), 8.02 (s, 1H), 7.67 (m, 1H), 7.55 (d, 1H), 6.87 (d, 1H), 6.70 (m, 1H), 3.84 (s, 2H), 1.62 (s, 9H).

Dimethylformamide di-tert-butyl acetal (0.34 mL, 0.29 g, 1.4 mmol) was added dropwise to a stirred solution of a mixture of 1 and 3-tert-butoxycarbonyl-7-oxo-7,8-dihydropyrrolo[2,3-g]benzimidazole (0.2 g, 0.7 mmol) in dry DMF (2 mL) and the mixture was stirred at room temperature for about 6 h. The solvent was evaporated under reduced pressure. The residue was dissolved in chloroform:methanol (10:1, 10 mL) and passed through a pad of silica gel. The filtrate was evaporated to give a mixture of 1 and 3-tert-butoxycarbonyl-8-(dimethylaminomethylidinyl)-7-oxo-7H-pyrrolo[2,3-g]benzimidazole as a brown solid, 0.042 g (17%). $^1$H NMR (DMSO-$d_6$): δ 10.10 (s, 1H), 8.40 (s, 1H), 7.40 (s, 1H), 7.22 (d, 1H, J=8.4 Hz), 6.82 (d, 1H, J=8.4 Hz), 1.64 (s, 9H).

A solution of a mixture of 1 and 3-tert-butoxycarbonyl8-(dimethylaminomethylidinyl)-7-oxo-7H-pyrrolo[2,3-g]benzimidazole (0.02 g, 0.061 mmol) and p-toluidine (0.01 g, 0.089 mmol) in acetic acid (1 mL) was heated at 120° C. for 3 h. The solvent was evaporated under vacuum and the residue was purified using silica gel chromatography with chloroform:methanol (10:1) as eluent to afford the title compound as a mixture of E/Z isomers, 0.012 g (68%). $^1$H NMR of principal isomer (DMSO-$d_6$): δ 12.57 (s, 1H), 12.38 (d, 1H, J=12.8 Hz), 10.01 (s, 1H), 8.33 (s, 1H), 7.95 (d, 1H, J=12.8 Hz), 7.24 (m, 5H), 6.80 (d, 1H, J=8 Hz), 2.28 (s, 3H). MS (AP⁻) 289 (100) (M⁺–H).

EXAMPLE 4

8-[(Z and E)-(3-Methyl-4-nitroanilino)methylidene] 3,6-dihydro[1,2,3]triazolo[4,5-e]indol-7-one Prepared as a 1:1 mixture of Z and E isomers in 95% yield from 8-dimethylaminomethylene-1-tert-butyloxycarbonyl-1,6-dihydro[1,2,3]triazolo[4,5-e]indol-7-one and 3-methyl4-nitroaniline according to the procedure of Example 5. $^1$H NMR (DMSO-$d_6$): δ 2.65 (s, 6H); 7.07 (d, J=8.5 Hz, 0.5H); 7.18 (d, J=8.5 Hz, 0.5H); 7.44 (dd, J=9.0 Hz and 1.5 Hz, 0.5H); 7.53 (m, 1H); 7.6 (m, 1H); 7.78 (brd d, J=8.2 Hz, 0.5H); 8.17 (d, J=9.0 Hz, 0.5H); 8.19 (d, J=9.5 Hz, 0.5H); 8.29 (brd d, J=12.6 Hz, 0.5H) 8.70 (d, J=12.1 Hz, 0.5H); 10.49 (s, 0.5H); 11.0 (s, 0.5H); 11.16 (d, J=12 Hz, 0.5H); 11.8 (brd d, J~8 Hz, 0.5H). APCI-MS: m/z 335 (M–H)⁻.

EXAMPLE 5

8-{(E/Z)-[4-nitro-3(trifluoromethyl)anilino] methylidene}-1,6-dihydro[1,2,3]triazolo[4,5-e]indol-7-one 5-Aminobenzotriazole (Lancaster Chemical, 10.14 g, 75 mmol) was dissolved in 200 ml of anhydrous DMF under nitrogen and 3.00 g (75 mmol) of sodium hydride (60% oil dispersion) was added in one portion. Hydrogen evolution and mild exothermicity was observed. The reaction was stirred at room temperature for 20 minutes and then cooled in an ice bath. A solution of di-tert-butyidicarbonate (16.4 g, 75 mmol) in 100 ml of anhydrous DMF was added via siphon. Stirring was continued for 2 hrs at ice bath temperature. The solvent was removed by rotary evaporation under high vacuum at 50 ° C. to give 32 g of viscous liquid. The crude product was dissolved in a minimum volume of chloroform and filtered through a short column of 600 ml silica gel, eluting with 10% methanol in chloroform. The collected product was evaporated to dryness, redissolved in 400 ml of diethyl ether, and washed three times with water and once with saturated sodium chloride solution. The ether solution was dried over magnesium sulfate and the solvent was removed to give 17.7 g of a mixture of 1- and 3-tert-butyloxycarbonyl-5-aminobenzotriazole contaminated with approx. 1 g of residual mineral oil. This material was then cyclized to the corresponding 3-methylthio-oxindole by the method of Procedure (Gassman). The resultant product (9.6 g of gray solid) was shown to be partially deprotected by NMR. This material was dissolved 200 ml of THF and treated with 50 g of zinc dust (activated by stirring for 10 min in 150 ml of 1 M HCl, followed by washing with three 100 ml portions of water). Saturated aqueous ammonium chloride (150 ml) was added and the reaction was stirred overnight at room temperature. The solution was filtered through Celite, washing with THF and ethyl acetate to give 4.0 g of gray solid which was primarily 1-tert-butyloxycarbonyl-1,6-dihydro[1,2,3]triazolo[4,5-e]indol-7one. This material (2.04 g, 7.4 mmol) was suspended in 10 ml of anhydrous DMF under nitrogen, cooled in an ice bath, and treated with 4.0 ml (3.4 g, 2.2 equiv) of dimethylformamide di-tert-butyl acetal. The reaction was allowed to warm to room temperature and was stirred overnight. The solvent was removed by rotary evaporation under high vacuum. The residue was filtered through a short column of 100 ml silica gel with 30% ethanol in dichloromethane. Evaporation of solvent provided 1.74 g of yellow solid which was primarily 8-dimethylaminomethylene-1-tert-butyloxycarbonyl-1,6-dihydro[1,2,3]triazolo[4,5-e]indol-7-one containing some product lacking the tert-butyloxycarbonyl protecting group.

The dimethylamino-oxindole derivative from above (33 mg, ~0.1 mmol) was combined in a reaction vial with 4-nitro-3-trifluoromethylaniline (25 mg, 0.12 mmol) in 1–2 ml of glacial acetic acid and stirred overnight in an oil bath at 110° C. The residue was triturated with 2 ml of ethanol, heating briefly to reflux. After cooling to room temperature, 2–3 ml of diethyl ether was added and the resulting precipitate was collected by filtration to give 7.8 mg (20%) of the title compound as a brown solid that was shown by NMR to be ~1:1 mixture of E/Z isomers. $^1$H NMR (DMSO-d$_6$): δ 7.07 (d, J=9 Hz, 0.5H); 7.20 (d, J=8 Hz, 0.5H); 7.63 (d, J=8 Hz, 0.5H); 7.8 –8.0 (m, 2H); 8.13 (s, 0.5H); 8.25–8.42 (m, 1.5H); 8.67 (d, J=11 Hz, 0.5H); 10.53 (s, 0.5H); 11.0 (s, 0.5H); 11.24 (d, J=11 Hz); 12.0 (brd d, J~9 Hz, 0.5H). APCI-MS: m/z 389 (M–H)$^-$.

EXAMPLE 6

8-[(Z and E)-(3-Chloro-4-nitroanilino)methylidene]-1,6-dihydro[1,2,3]triazolo[4,5-e]indol-7-one Prepared as a ~1:1 mixture of Z and E isomers in 70% yield from 8-dimethylaminomethylene-1-tert-butyloxycarbonyl-1,6-dihydro[1,2,3]triazolo[4,5-e]indol-7-one and 3-chloro-4-nitroaniline according to the procedure of Example 5. $^1$H NMR (DMSO-d$_6$): δ 7.06 (d, J=8.8 Hz, 0.5H); 7.20 (d, J=8.5 Hz, 0.5H); 7.3–7.66 (m, 1.5H); 7.80 (brd m, 0.5H); 7.85 (d, J=2.5 Hz, 0.5H); 7.91 (d, J=2.5 Hz, 0.5H); 8.23 (d, J=9.1 Hz, 1H); 8.32 (brd m, 0.5H); 8.63 (d, J=11.7 Hz, 0.5H); 10.5 (s 0.5H); 11.0 (s, 0.5H); 11.1 (d, J=11.7 Hz, 0.5H); 11.8 (brd, 0.5H). APCI-MS: m/z 355 (M–H)$^-$.

EXAMPLE 7

8-[(Z and E)-(3,5-Dimethyl-4-nitroanilino)methylidene]-1,6-dihydro[1,2,3,]triazolo[4,5-e]indol-7-one Prepared as a ~1:1 mixture of Z and E isomers in 74% yield from 8-dimethylaminomethylene-1-tert-butyloxycarbonyl-1,6-dihydro[1,2,3]triazolo[4,5-e]indol-7-one and 3,5-dimethyl-4-nitroaniline according to the procedure of Example 5. $^1$H NMR (DMSO-d$_6$): δ 2.36 (s, 6H); 7.07 (d, J=8.5 Hz, 0.5H); 7.17 (d, J=8.5 Hz, 0.5H); 7.37 (s, 2H); 7.57 (d, J=8.5 Hz, 0.5H); 7.76 (brd d, J=8.5 Hz, 0.5H); 8.24 (brd d, J=12 Hz, 0.5H); 8.69 (brd d, J=12 Hz, 0.5H); 10.44 (s, 0.5H); 10.97 (s, 0.5H); 11.07 (brd d, J=12 Hz, 0.5H); 11.6 (brd d, J=12 Hz, 0.5H). APCI-MS: m/z 349 (M–H)$^-$.

EXAMPLE 8

8-((Z and E)-{4-[2,2,2-Trifluoro-1-hydroxy-1-(trifluoromethyl)ethyl]anilino}methylidene)-1,6-dihydro[1,2,3,]triazolo[4,5-e]indol-7-one The title compound was prepared as a ~1:1 mixture of Z and E isomers in 54% yield from 8-dimethylaminomethylene-1-tert-butyloxycarbonyl-1,6-dihydro[1,2,3]triazolo[4,5-e]indol-7-one and 4-[2,2,2-trifluoro-1-hydroxy-1-(trifluoromethyl)ethyl]aniline according to the procedure of Example 5. $^1$H NMR (DMSO-d$_6$): δ 7.07 (d, J=8.7 Hz, 0.5H); 7.17 (d, J=8.7 Hz, 0.5H); 7.56 (d, J=8.7 Hz, 0.5H); 7.6 and 7.75 (2 overlapping Abq, 4H); 8.22 (d, J=13 Hz, 0.5H); 8.75 (m, 1H); 10.4 (s, 0.5H); 10.9 (s, 0.5H); 11.08 (d, J=13 Hz, 0.5H); 11.7 (brd d, J=13 Hz, 0.5H). APCI-MS: m/z 442 (M–H)$^-$.

EXAMPLE 9

8{(Z and E)-[4-(2-Hydroxyethyl)anilino]methylidene}-1,6-dihydro[1,2,3]triazolo[4,5-e]indol-7-one The acetate ester of the title compound was obtained as a ~1:1 mixture of Z and E isomers in 71% yield (26 mg) from 8-dimethylaminomethylene-1 tert-butyloxycarbonyl-1,6-dihydro[1,2,3]triazolo[4,5e]indol-7-one (25 mg) and 4-(2-hydroxyethyl)aniline (17 mg) in acetic acid according to the procedure of Example 5. The product was stirred in 4 ml methanol with 0.2 ml of 2M NaOH overnight at room temperature. The reaction solution was acidified with 0.2 ml of 2M sulfuric acid, and ethanol and diethyl ether were added. The resulting precipitate was collected by filtration and stirred in 3 ml of water for several hours to dissolve Na$_2$SO$_4$, then filtered and dried to give the title compound (16 mg dark green solid, 70%). $^1$H NMR (DMSO-d$_6$): δ 2.69 (t, J~6 Hz, 2H); 3.58 (m, 2H); 4.62 (m, 1H); 7.01 (d, J=8.5 Hz, 0.5H); 7.12 (d, J=8.5 Hz, 0.5H); 7.26 and 7.32 (overlapping Abq, 4H); 7.46 (d, J=8.5 Hz, 0.5H); 7.64 (brd, 0.5H); 8.13 (d, J=13 Hz, 0.5H); 10.3 (s, 0.5H); 10.8 (s, 0.5H); 11.0 (d, J=13 Hz, 0.5H); 11.45 (brd, 0.5H). APCI-MS: m/z 320 (M–H)$^-$.

EXAMPLE 10

8-{(Z)-[4-(Methylsulfanyl)anilino]methylidene}-6H-[1,3]thiazolo[5,4-e]indol-7-one This compound was prepared with 4-methylthioaniline according to Procedure G on a 0.5 mmol scale. The yield was 0.089 grams (53%) for $C_{17}H_{13}N_3O_1S_2$.

$^1$H NMR (400 MHz, DMSO-d$_6$) δ : 10.9(d, 1H), 10.78(s, 1H), 9.21(s, 1H), 7.9(d, 1H), 7.7(d, 1H), 7.25(d, 2H), 7.1(d, 1H), 6.8(d, 2H), 2.4(s, 3H). ESI-MS m/z 338(M–1).

EXAMPLE 11

8-[(Z)-(3,5-Dimethoxyanilino)methylidene]-6H-[1,3]thiazolo[5,4-e]indol-7-one

This compound was prepared 3,5-dimethoxyaniline according to Procedure G on a 0.5 mmol scale. The yield was 0.076 grams (43%) for $C_{18}H_{15}N_3O_3S_1$.

$^1$H NMR (400 MHz, DMSO-d$_6$) 67 : 10.9(d, 1H), 10.83(s, 1H), 9.21(s, 1H), 7.98(d, 1H), 7.77(d, 1H), 7.08(d, 1H), 6.59(s, 2H), 6.25(s, 1H), 3.77(s, 6H). ESI-MS m/z 352(M–1).

EXAMPLE 12

8[(Z)-(4-Hydroxyanilino)methylidene]-6H-[1,3]thiazolo[5,4-e]indol-7-one

This compound was prepared with 4-hydroxyaniline according to Procedure G on a 0.5 mmol scale. The yield was 0.081 grams (53%) for $C_{16}H_{11}N_3O_2S_1$.

$^1$H NMR (400 MHz, DMSO-d$_6$) δ : 10.95(d, 1H), 10.75(s, 1H), 9.42(s, 1H), 9.2(s, 1H), 7.91(d, 1H), 7.72(d, 1H), 7.23(d, 2H), 7.07(d, 1H), 6.79(d, 2H). ESI-MS m/z 308(M–1).

EXAMPLE 13

1-[(Z)-(3-Methoxyanilino)methylidene]-1,3-dihydro-2H-pyrrolo[3,2-f]quinolin-2-one Prepared from the dimethylaminomethylene derivative (Procedure E) of 1,3-dihydro-2H-pyrrolo[3,2-f]quinolin-2-one (Procedure C) with 3-methoxyaniline according to Procedure G to give the title compound in 63% yield. $^1$H NMR (DMSO-d$_6$) δ : 3.80 (s, 3H); 6.68 (dd, J=1.8, 8.2 Hz, 1H); 7.06 (brd d, J=8.0 Hz, 1H); 7.11 (brd s, 1H); 7.29 (t, J=8.1 Hz, 1H); 7.40 (d, J=8.8 Hz, 1H); 7.46 (dd, J=8.5, 4.1 Hz, 1H); 7.71 (d, J=8.8 Hz,1H); 8.70 (d, J=4.1 Hz, 1H); 8.8 (2 overlapping d, J=8.5, 12 Hz, 2H); 10.94 (s, 1H); 11.74 (d, J=12 Hz, 1H). ES-MS: m/z 316 (M–H)⁻.

EXAMPLE 14

3-{[(Z)-(2-Oxo-2,3-dihydro-1H-pyrrolo[3,2-f]quinolin-1-ylidene)methyl]amino}benzonitrile Prepared from the dimethylaminomethylene derivative (Procedure E) of 1,3-dihydro-2H-pyrrolo[3,2-f]quinolin-2-one (Procedure C) with 3-aminobenzonitrile according to Procedure G in acetic acid to give the title compound in 78% yield as the acetate salt. $^1$H NMR (DMSO-$d_6$) δ : 1.88 (s, 3H); 7.39 (d, J=8.5 Hz, 1H); 7.45–7.6 (m, 3H); 7.78 (m, 2H); 8.20 (s, 1H); 8.75 (d, J=4 Hz, 1H); 8.8–8.9 (m, 2H); 11.0 (s, 1H); 11.8 (d, J=12 Hz, 1H); 11.95 (s, 1H). ES-MS: m/z 313 (M+H)⁺.

EXAMPLE 15

1-[(Z)-4-Toluidinomethylidene]-1,3dihydro-2H-pyrrolo[3,2-f]quinolin-2-one

Prepared from the dimethylaminomethylene derivative (Procedure E) of 1,3-dihydro-2H-pyrrolo[3,2-f]quinolin-2-one (Procedure C) with p-toluidine according to Procedure G to give the title compound in 98% yield. $^1$H NMR (DMSO-$d_6$) δ : 2.25 (s, 3H); 7.2 (m, 2H); 7.35–7.5 (m, 4H); 7.70 (d, J=8.5 Hz, 1H); 8.70 (d, J=4.0 Hz, 1H); 7.8 (m, 2H); 10.9 (s, 1H); 11.8 (d, J=12 Hz, 1H). ES-MS: m/z 302 (M+H)⁺.

EXAMPLE 16

1-[(Z)-(4-Methoxyanilino)methylidene]-1,3-dihydro-2H-pyrrolo[3,2-f]quinolin-2-one Prepared from the dimethylaminomethylene derivative (Procedure E) of 1,3-dihydro-2H-pyrrolo[3,2-f]quinolin-2-one (Procedure C) with 4-methoxyaniline according to Procedure G in acetic acid to give the title compound in 54% yield as the acetate salt. $^1$H NMR (DMSO-$d_6$) δ : 1.88 (s, 3H); 3.75 (s, 3H); 6.97 (d, J=8.9 Hz, 2H); 7.39 (d, J=8.7 Hz, 1H); 7.43–7.5 (m, 3H); 7.68 (d, J=8.5 Hz, 1H); 8.70 (d, J=4.0 Hz, 1H); 8.75–8.82 (m, 2H); 10.9 (s, 1H); 11.75 (d, J=12 Hz, 1H); 11.9 (s, 1H). ES-MS: m/z 318 (M+H)⁺.

EXAMPLE 17

3-({[(Z and E)-7-Oxo-6,7-dihydro[1,2,3]triazolo[4,5-e]indol-8(1H)-ylidene]methyl}amino)benzonitrile Prepared as a ~3:2 mixture of geometrical isomers in 88% yield from 8-dimethylaminomethylene-1-tert-butyloxycarbonyl-1,6-dihydro[1,2,3]triazolo[4,5-e]indol-7-one and 3-aminobenzonitrile according to the procedure of Example 5. $^1$H NMR (DMSO-$d_6$): δ 6.88 and 7.02 (2 d, 3:2 ratio, J=8.7 Hz, 1H); 7.45–7.6 (m, ~2.6H); 7.65–7.8 (m, ~1.4H); 7.90 and 7.95 (2 s, 1H); 8.15 and 8.83 (2 s, 1H); 10.2 and 10.85 (2 s, 1H). ES-MS: m/z 303 (M+H)⁺.

EXAMPLE 18

8-[(Z and E)-4-Toluidinomethylidene]-1,6-dihydro[1,2,3,]triazolo[4,5-e]indol-7-one Prepared as a ~1:1 mixture Z and E isomers in 78% yield from 8-dimethylaminomethylene-1-tert-butyloxycarbonyl-1,6-dihydro[1,2,3]triazolo[4,5-e]indol-7-one and p-toluidine according to the procedure of Example 5. $^1$H NMR (DMSO-$d_6$): δ 2.28 (s, 3H); 7.01 and 7.11 (2 d, 1:1 ratio, J=8.4 Hz, 1H); 7.22 and 7.32 (2 overlapping ABq, 4H); 7.45 and 7.64 (2 d, 1:1 ratio, J=8.4 Hz, 1H); 8.11 and 8.68 (2 d, 1:1 ratio, J=13 Hz, 1H); 10.3 and 10.8 (2 s, 1:1 ratio, 1H); 11.0 and 11.45 (2 d, 1:1 ratio, J=13 Hz, 1H). ES-MS: m/z 292 (M+H)⁺.

EXAMPLE 19

8-[(Z and E)-(4-Methoxyanilino)methylidene]-1,6-dihydro[1,2,3,]triazolo[4,5-e]indol-7-one Prepared as a ~1:1 mixture Z and E isomers in 88% yield from 8-dimethylaminomethylene-1-tert-butyloxycarbonyl-1,6-dihydro[1,2,3]triazolo[4,5-e]indol-7-one and 4-methoxyaniline according to the procedure of Example 5. $^1$H NMR (DMSO-$d_6$): δ 3.78 (s, 3H); 6.95–7.1 (m, 3H); 7.3–7.45 (m, 2.5H); 7.60 (d, J=8.5 Hz, 0.5H); 8.05 and 8.65 (2 d, J=12 Hz, 1H), 10.2 and 10.75 (2 s, 1H); 10.95 and 11.55 (2 brd d, J=12 Hz, 1H). ES-MS: m/z 308 (M+H)⁺.

EXAMPLE 20

8-{(Z)-[4-(4-Morpholinyl)anilino]methylidene}-6H-[1,3]thiazolo[5,4-e]indol-7-one Prepared according to Procedure G with 4-(4-morpholino)aniline in 78% yield. $^1$H NMR (DMSO-$d_6$): δ 10.96 (d, 1H, J=12.6 Hz), 10.76 (s, 1H), 9.20 (s, 1H), 7.95 (d, 1H, J=12.5 Hz), 7.74 (d, 1H, J=8.4Hz), 7.31 (d, 2H, J=8.8 Hz), 7.08 (d, 1H, J=8.4 Hz), 6.99 (d, 2H, J=9.0 Hz), 3.72 (t, 4H, J=4.7 Hz), 3.07 (t, 4H, J=4.8 Hz); ES-MS m/z 379 (M+H).

EXAMPLE 21

N-(4-{[(Z)-(7-Oxo-6,7-dihydro-8H-[1,3]thiazolo[5,4-e]indol-8-ylidene)methyl]amino}phenyl)acetamide Prepared according to Procedure G with N-(4-aminophenyl)acetamide in 87% yield. $^1$H NMR (DMSO-$d_6$): δ 11.01 (d, 1H, J=12.5 Hz), 10.80 (s, 1H), 9.95 (s, 1H), 9.22 (s, 1H), 7.99 (d, 1H, J=12.5 Hz), 7.75 (d, 1H, J=8.4 Hz), 7.60(d, 2H, J=8.8 Hz), 7.35 (d, 2H, J=8.8 Hz), 7.09 (d, 1H, J=8.4 Hz), 2.01 (s, 3H).

EXAMPLE 22

8-{(Z)-[4-(2-Hydroxyethyl)anilino]methylidene}-6H-[1,3]thiazolo[5,4-e]indol-7-one Prepared according to Procedure G with 4-(2-hydroxyethyl)aniline in 41% yield. $^1$H NMR (DMSO-$d_6$): δ 10.98 (d, 1H, J=12.5 Hz), 10.81 (s, 1H), 9.22 (s,1H), 8.00 (d, 1H, J=12.5 Hz), 7.76 (d, 1H, J=8.4 Hz), 7.31 (d, 2H, J=8.4 Hz), 7.24 (d, 2H, J=8.4 Hz), 7.09 (d, 1H, J=8.4 Hz), 4.62 (t, 1H, J=5.1 Hz), 3.59–3.54 (m, 2H), 2.69 (t, 2H, J=7.0 Hz); ES-MS m/z 338 (M+H).

EXAMPLE 23

8-{(Z)-[4-(4-Pyridinylmethyl)anilino]methylidene}-6H-[1,3]thiazolo[5,4-e]indol-7-one Prepared according to Procedure G with 4-(4-pyridylmethyl)aniline in 66% yield. $^1$H NMR (DMSO-$d_6$): δ 10.99 (d, 1H, J=12.5 Hz), 10.84 (s, 1H), 9.23 (s, 1H), 8.74 (d, 2H, J=6.4 Hz), 8.00 (d, 1H, J=12.3 Hz), 7.82 (d, 2H, J=6.2Hz), 7.77 (d,1H, J=8.4 Hz), 7.40 (d,2H, J=8.6 Hz), 7.35 (d, 2H, J=8.4 Hz) 7.09 (s,1H), 4.20 (s, 2H); ES-MS m/z 384 (M+H).

EXAMPLE 24

4-{[(Z)-(7-Oxo-6,7-dihydro-8H-[1,3]thiazolo[5,4-e]indol-8-ylidene)methyl]amino}benzamide Prepared according to Procedure G with 4-aminobenzamide in 73% yield. $^1$H NMR (DMSO-d$_6$): δ 11.14 (d, 1H, J=12.3 Hz), 10.90 (s, 1H), 9.27 (s, 1H), 8.10 (d,1H, J=12.3 Hz), 7.93 (d, 3H, J=8.4 Hz), 7.82 (d, 1H, J=8.4 Hz), 7.49 (d, 2H, J=8.6 Hz), 7.30 (s, 1H), 7.12 (d, 1H, J=8.4 Hz); ES-MS m/z 337 (M+H).

EXAMPLE 25

6-Bromo-3{(Z and E)-[4-(4-morpholinyl)anilino]methylidene}-1,3-dihydro-2H-indol-2-one Prepared according to Example 1 in 87% yield to give ~4:1 isomer mixture. Principal isomer: $^1$H NMR (DMSO-d$_6$): δ 10.67 (d, 1H, J=12.5 Hz), 10.56(s,1H), 8.57 (d,1H, J=12.8 Hz), 7.48 (d,1H, J=7.9 Hz), 7.35–7.29 (m,2H), 7.11–7.04 (m, 3H), 6.93 (s,1H), 3.76 (s, 4H), 3.15 (s,4H); ES-MS m/z 400, 402 (M+1).

EXAMPLE 26

4-{[(Z)-(6-Bromo-2-oxo-1,2-dihydro-3H-indol-3-ylidene)methyl]amino}benzamide

Prepared according to Example 1 with 4-aminobenzamide in 70% yield. $^1$H NMR (DMSO-d$_6$): δ 10.75 (d,1H, J=12.5 Hz), 10.65 (s,1H), 8.69 (d,1H, J=12.5 Hz), 7.87 (d,3H, J=8.6 Hz), 7.54 (d,1H, J=7.9Hz), 7.44 (d, 2H, J=8.6 Hz), 7.24 (s,1H), 7.09 (d,1H, J=8.2 Hz), 6.95 (d,1H, J=1.4 Hz); ES-MS m/z 356,358 (M−1).

EXAMPLE 27

N-(4-{[(Z and E)-(6-Bromo-2-oxo-1,2-dihydro-3H-indol-3-ylidene)methyl]amino}phenyl)acetamide Prepared according to Example 1 with N-(4-aminophenyl)acetamide in 79% yield to give ~9:1 isomer mixture. Principal isomer: $^1$H NMR (DMSO-d$_6$): δ 10.75 (d,1H, J=12.5 Hz), 10.65 (s,1H), 8.69 (d,1H, J=12.5 Hz), 7.87 (d,3H, J=8.6 Hz), 7.54 (d,1H, J=7.9 Hz), 7.44 (d,2H, J=8.6 Hz), 7.24 (s,1H), 7.09 (d,1H, J=8.2 Hz), 6.95 (d,1H, J=1.4 Hz); ES-MS m/z 370, 372 (M−1).

EXAMPLE 28

6-Bromo-3-{(Z)-[4-(2-hydroxyethyl)anilino]methylidene}-1,3-dihydro-2H-indol-2-one Prepared according to Example 1 with 4-(2-hydroxyethyl)aniline in 85% yield. $^1$H NMR (DMSO-d$_6$): δ 10.67 (d,1H, J=12.8 Hz), 10.58 (s, 1H), 8.61 (d,1H, J=12.6 Hz), 7.50 (d,1H, J=8.2 Hz), 7.29 (d,2H, J=8.4 Hz), 7.19 (d,2H, J=8.2 Hz), 7.06 (d,1H, J=8.1 Hz ), 6.93 (d,1H, J=1.5 Hz), 4.60 (t, 1H,J=5.1 Hz), 3.55 (m,2H), 2.66 (t,2H, J=7.0 Hz); MS-ES m/z 357, 359 (M−1).

EXAMPLE 29

1-{(Z)-[4-(4-Morpholinyl)anilino]methylidene}-1,3-dihydro-2H-pyrrolo[3,2-f]quinolin-2-one Prepared according to Example 13 with 4-(4-morpholino)aniline in 65% yield. $^1$H NMR (DMSO-d$_6$): δ 11.77 (d,1H, J=12.3 Hz), 10.88 (s,1H), 8.77 (m,2H), 8.69 (d,1H, J=4.0 Hz), 7.67 (d, 1H, J=8.6 Hz), 7.5–7.4 (m, 4H), 6.98 (d,2H, J=8.8 Hz), 3.72 (t,4H, J=4.5 Hz), 3.07 (t, 4H, J=4.6 Hz); ES-MS m/z 373 (M+H).

EXAMPLE 30

1-{(Z)-[4-(4-Pyridinylmethyl)anilino]methylidene}-1,3-dihydro-2H-pyrrolo[3,2-f]quinolin-2-one Prepared according to Example 13 with 4-(4-pyridylmethyl)aniline in 59% yield. $^1$H NMR (DMSO-d$_6$): δ 11.74 (d,1H, J=12.1 Hz), 10.93 (s,1H), 8.80–8.75 (m,2H), 8.70 (d,1H, J=3.9 Hz), 8.44 (d,2H, J=5.3 Hz), 7.70 (d, 1H, J=8.6 Hz), 7.47–7.43 (m,3H), 7.39 (d,1H, J=8.8 Hz), 7.28 (d,2H, J=8.1 Hz), 7.24 (d,2H, J=5.1 Hz), 3.95 (s,2H); ES-MS m/z 379 (M+H).

EXAMPLE 31

N-(4-{[(Z)-(2-Oxo-2,3-dihydro-1H-pyrrolo[3,2-f]quinolin-1-ylidene)methyl]amino}phenyl)acetamide Prepared according to Example 13 with N-(4-aminophenyl)acetamide in 72% yield. $^1$H NMR (DMSO-d$_6$): δ 11.77 (d,1H, J=12.1 Hz), 10.92 (s, 1H), 9.95 (s,1H), 8.8–8.77 (m,2H), 8.70 (d,1H, J=3.5 Hz), 7.69 (d,1H, J=8.8 Hz), 7.60 (d,2H, J=9.0 Hz), 7.5–7.43 (m,3H), 7.39 (d,1H, J=8.6 Hz), 2.01 (s,3H) ES-MS m/z 345 (M+H).

EXAMPLE 32

1-{(Z)-[4-(2-Hydroxyethyl)anilino]methylidene}-(1,3-dihydro-2H-pyrrolo[3,2-f]quinolin-2-one Prepared according to Example 13 with 4-(2-hydroxyethyl)aniline in 75% yield. $^1$H NMR (DMSO-d$_6$): δ 11.75 (d,1H, J=12.1 Hz), 10.92 (s, 1H), 8.82–8.79 (m,2H), 8.70 (d,1H, J=3.9 Hz), 7.70 (d,1H, J=8.6 Hz), 7.5–7.4 (m 4H), 7.23 (d,2H, J=8.2 Hz), 4.62 (t,1H, J=5.1 Hz), 3.6–3.55 (m,2H), 2.70 (t,2H, J=7.0 Hz); ES-MS m/z 332 (M+H).

EXAMPLE 33

4-{[(Z)-(2-Oxo-2,3-dihydro-1H-pyrrolo[3,2-f]quinolin-1-ylidene)methyl]amino}benzamide Prepared according to Example 13 with 4-aminobenzamide in 54% yield. $^1$H NMR (DMSO-d$_6$): δ 11.90 (d,1H, J=11.9 Hz), 11.03 (s, 1H), 8.87–8.83 (m,2H), 8.76 (d,1H, J=4.0 Hz), 7.93–7.89 (m,3H), 7.78 (d,1H,J=8.8 Hz), 7.61 (d,2H, J=8.6 Hz), 7.52 (dd,1H, J=4.1,8.5 Hz), 7.45 (d,1H,J=8.8 Hz), 7.3 (s, 1H); ES-MS m/z 331 (M+H).

EXAMPLE 34

1-[(Z)-(4-Hydroxyanilino)methylidene]-1,3-dihydro-2H-pyrrolo[3,2-f]quinolin-2-one Prepared according to Example 13 with 4-hydroxyaniline in 84% yield. $^1$H NMR (DMSO-d$_6$): δ 11.76 (d,1H, J=12.3 Hz), 10.90 (s, 1H), 9.44 (s, 1H), 8.77–8.68 (m,3H), 7.71 (d, 1H,J=8.8 Hz), 7.44–7.33 (m,4H), 6.83 (d,2H, J=8.6 Hz); ES-MS m/z 304 (M+H).

EXAMPLE 35

6-(2-Furyl)-3-{(Z)-[4-(4-morpholinyl)anilino]methylidene}-1,3-dihydro-2H-indol-2-one Prepared from the dimethylaminomethylene derivative (Procedure E) of 6-(2-furyl)oxindole (prepared according to Procedure I) with 4-(4-morpholino)aniline according to Procedure G in 90% yield. ¹H NMR (DMSO-d₆): δ 10.66 (d,1H, J=12.6 Hz), 10.51 (s,1H), 8.51 (d, 1H, J=12.8 Hz), 7.65 (s,1H), 7.56 (d,1H, J=7.9 Hz), 7.29–7.25 (m,3H), 7.1 (s,1H), 6.95 (d,2H, J=8.8 Hz), 6.77 (d,1H, J=2.9 Hz), 6.52 (s,1H), 3.71 (s,4H), 3.05 (s,4H); ES-MS m/z 388 (M+H).

EXAMPLE 36

N-[4-({(Z and E)-[6-(2-Furyl)-2-oxo-1,2-dihydro-3H-indol-3-ylidene]methyl}amino)phenyl]acetamide Prepared according to Example 35 with N-(4-aminophenyl)acetamide in 29% yield. ¹H NMR (DMSO-d₆): δ 10.68 (d,1H, J=12.6 Hz), 10.55 (s,1H), 9.91 (s,1H), 8.53 (d,1H, J=12.6 Hz), 7.66 (s,1H), 7.57 –7.54 (m,3H), 7.32–7.27 (m,3H), 7.10 (s,1H), 6.78 (d,1H, J=2.9 Hz), 6.53 (s,1H), 2.00 (s,3H); ES-MS m/z 358 (M–H).

EXAMPLE 37

6-(2-Furyl)-3-{(Z)-[4-(2-hydroxyethyl)anilino]methylidene}-1,3-dihydro-2H-indol-2one Prepared according to Example 35 with 4-(2-hydroxyethyl)aniline in 63% yield. ¹H NMR (DMSO-d₆): δ 10.68 (d,1H, J=12.5 Hz), 10.56 (s,1H), 8.57 (d,1H, J=12.6 Hz), 7.66 (s,1H), 7.58 (d,1H, J=7.9 Hz), 7.28 (br s,3H), 7.19 (d,2H, J=8.1 Hz), 7.11 (s,1H), 6.78 (s,1H), 6.53 (s,1H), 4.61 (t,1H, J=4.9 Hz), 3.58 –3.55 (m, 2H), 2.67 (t, 2H, J=6.9 Hz); ES-MS m/z 345 (M–H).

EXAMPLE 38

3-{(Z)-[4-(4-Morpholinyl)anilino]methylidene}-6-vinyl-1,3-dihydro-2H-indol-2-one Prepared according to Procedure G with the dimethylaminomethylene derivative (Procedure E) of 6-vinyloxindole (Procedure I) and 4-(4-morpholino)aniline in 75% yield. ¹H NMR (DMSO-d₆): δ 10.65 (d,1H, J=2.8 Hz), 10.43 (s,1H), 8.48 (d,1H, J=12.5 Hz), 7.48 (d,1H, J=7.9 Hz), 7.27 (d,2H, J=8.9 Hz), 7.00 (d,1H, J=7.9 Hz), 6.95 (d,2H, J=8.9 Hz), 6.89 (s,1H), 6.87–6.62 (m,1H), 5.64 (d,1H, J=17.84 Hz), 5.08 (d,1H, J=11.1 Hz), 3.71 (t,4H, J=4.6 Hz), 3,05 (t,4H, J=4.6 Hz); ES-MS m/z 346 (M–H).

EXAMPLE 39

3-{(Z)-[4-(4-Pyridinylmethyl)anilino]methylidene}-vinyl-1,3-dihydro-2H-indol-2-one Prepared according to Example 38 with 4-(4-pyridylmethyl)aniline in 51% yield. ¹H NMR (DMSO-d₆): δ 10.66 (d,1H, J=12.5 Hz), 10.49 (s,1H), 8,53 (d,1H, J=12.5 Hz), 8.43 (d,2H, J=5 Hz), 7.50 (d,1H, J=7.9 Hz), 7.32 (d,2H, J=8.6 Hz), 7.24–7.21 (m,4H), 7.01 (d,1H, J=7.9 Hz), 6,89 (s,1H), 6.70–6.63 (m,1H), 5.65 (d,1H, J=17.5 Hz), 5.10 (d,1H, J=11.1 Hz), 3.91 (s,2H); ES-MS m/z 352 (M–H).

EXAMPLE 40

N-(4-{(Z)-[(2Oxo-6-vinyl-1,2-dihydro-3H-indol-3-ylidene)methyl]amino}phenyl)acetamide Prepared according to Example 38 with N-(4-aminophenyl)acetamide in 42% yield. ¹H NMR (DMSO-d₆): δ 10.67 (d,1H, J=12.5 Hz), 10.47 (s,1H), 9.90 (s,1H), 8.50 (d,1H, J=12.5 Hz), 7.55 (d,2H, J=8.6 Hz), 7.49 (d,1H, J=7.85 Hz), 7.30 (d,2H, J=8.9 Hz), 7.01 (d,1H, J=7.9 Hz), 6.89 (s,1H), 6.70–6.63 (m,1H), 5.65 (d,1H, J=17.5 Hz), 5.09 (d,1H, J=11.1 Hz), 2.00 (s,3H); ES-MS m/z 318 (M–H).

EXAMPLE 41

3-{(Z)-[4-(2-Hydroxyethyl)anilino]methylidene}-6-vinyl-1,3-dihydro-2H-indol-2-one Prepared according to Example 38 with 4-(2-hydroxyethyl)aniline in 55% yield. ¹H NMR (DMSO-d₆): δ 10.66 (d,1H,J=12.5 Hz), 10.48 (s,1H), 8.54 (d,1H, J=12.5 Hz), 7.51 (d,1H, J=7.9 Hz), 7.28 (d,2H, J=8.2 Hz), 7.19 (d,2H, J=8.2 Hz), 7.01 (d,1H, J=7.9 Hz), 6.9 (s,1H), 6.88–6.63 (m,1H), 5.65 (d,1H, J=17.5 Hz), 5.09 (d,1H, J=11.1 Hz), 4.60 (t,1H, J=5.0 Hz), 3.58–3.53 (m,2H), 2.66 (t,2H, J=7.0 Hz); ES-MS m/z 305 (M–H).

EXAMPLE 42

6-(2-Furyl)-3-{(Z)-[4(4-pyridinylmethyl)anilino]methylidene}-1,3-dihydro-2H-indol-2-one Prepared according to Example 35 with 4-(4-pyridylmethyl)aniline in 42% yield. ¹H NMR (DMSO-d₆): δ 10.67 (d,1H, J=112.6 Hz), 10.56 (s,1H), 8.56 (d,1H, J=12.6 Hz), 8.43 (d,2H, J=5.3 Hz), 7.66 (s,1H), 7.57 (d,1H, J=8.1 Hz), 7.34–7.22 (m,7H), 7.10 (s,1H), 6.79 (d,1H, J=3.3 Hz), 6.53 (s, 1H), 3.91 (s,2H); ES-MS m/z 391 (M–H).

EXAMPLE 43

6-(2-Furyl)-3-[(Z)-(4-hydroxyanilino)methylidene]-1,3-dihydro-2H-indol-2-one

Prepared according to Example 35 with 4-hydroxyaniline in 44% yield. ¹H NMR (DMSO-d₆): δ 10.63 (d,1H, J=12.8 Hz), 10.49 (s,1H), 9.32 (s,1H), 8.46 (d,1H, J=12.8 Hz), 7.65 (s,1H), 7.54 (d,1H, J=7.9 Hz), 7.26 (d,1H, J=7.9 Hz), 7.21 (d,2H, J=8.8 Hz), 7.01 (s,1H), 6.77–6.74 (m,3H), 6.52 (s,1H); ES-MS m/z 317 (M–H).

EXAMPLE 44

3-{(Z)-[4-(4-Morpholinyl)anilino]methylidene}-6-(2-thienyl)-1,3-dihydro-2H-indol-2-one Prepared from the dimethylaminomethylene derivative (Procedure E) of 6-(2-thienyl)oxindole (prepared according to Procedure I) with 4-(4-morpholino)aniline according to Procedure G in 47% yield. ¹H NMR (DMSO-d₆): δ 10.67 (d,1H, J=12.9 Hz), 10.65 (s,1H), 8.52 (d,1H, J=12.8 Hz), 7.55 (d,1H, J=7.9 Hz), 7.42 (d,1H,J=5.1 Hz), 7.36 (d,1H, J=3.3 Hz) 7.29 (2H, 8.8 Hz),7.22 (d,1H, J=7.9 Hz), 7.08–7.07 (m,1H), 7.04 (s,1H), 6.95 (d,2H, J=9.0 Hz), 3.71 (t,4H, J=4.5 Hz), 3.05 (t,4H, J=4.6 Hz).

EXAMPLE 45

N-[4-({(Z)-[2-Oxo-6-(2-thienyl)-1,2-dihydro-3H-indol-3-ylidene]methyl}amino)phenyl]acetamide Prepared according to Example 44 with N-(4-aminophenyl)acetamide in 33% yield. ¹H NMR (DMSO-d₆): δ 10.68 (d,1H, J=12.6 Hz), 10.52 (s,1H), 9.91 (s,1H), 8.53 (d,1H, J=12.6 Hz), 7.55 (d,3H, J=8.4 Hz), 7.43 (d,1H, J=5.1 Hz), 7.37 (d,1H, J=3.1 Hz), 7.32 (d,2H, J=8.8 Hz), 7.23 (d,1H, J=9.2 Hz), 7.07 (t,1H, J=4.3 Hz), 7.04 (s,1H), 2.00 (s,3H); ES-MS m/z 374 (M–H).

EXAMPLE 46

6-Bromo-3-{(Z)-[3-(hydroxymethyl)anilino]methylidene}-1,3-dihydro-2H-indol-2-one Prepared according to Example 1 with 3-(hydroxymethyl)aniline in 54% yield. ¹H NMR (DMSO-d₆): δ 10.74 (d,1H, J=12.8 Hz), 10.60 (s,1H), 8.67 (d,1H, J=12.8 Hz), 7.53 (d,1H, J=8.2 Hz), 7.30 (d,2H, J=7.3 Hz), 7.24 (d,1H, J=8.2 Hz), 7.07 (d,1H, J=9.3 Hz), 7.02 (d,1H, 7.3 Hz), 6.94 (s,1H), 5.23 (t,1H, J=5.7 Hz), 4.48 (d,2H, J=5.7 Hz); ES-MS m/z 343, 345 (M−1).

EXAMPLE 47

6-Bromo-3-{(Z and E)-[4-(5-methyl-3-oxo-2,3-dihydro-1H-pyrazol-1-yl)anilino]methylidene}-1,3-dihydro-2H-indol-2-one Prepared according to Example 1 with 2-(4-aminophenyl)-3-methyl-pyrazoline-5-one in 45% yield as ~9:1 isomer mixture. Major isomer: $^1$H NMR (DMSO-d$_6$): δ 10.73 (d,1H, J=12.6 Hz), 10.60(s,1H), 9.82 (s,1H), 8.65 (d,1H, J=12.6 Hz), 7.52 (d,1H, J=8.1 Hz), 7.47 (d,2H, J=8.8 Hz), 7.42 (d,2H, J=8.8 Hz), 7.08 (d,1H, J=8.1 Hz), 6.94 (s,1H), 5.54 (s, 1H), 2.23 (s,3H); ES-MS m/z 411, 413 (M+1).

EXAMPLE 48

3-Ethyl-3-(4-{(Z)-[(7-oxo-6,7-dihydro-8H-[1,3]thiazolo[5,4-e]indol-8-ylidene)methyl]amino}phenyl)-2,6-piperidinedione A mixture of 8-dimethylamino-methylene-6,8-dihydro-1-thia-3,6-diaza-as-indacen-7-one (Procedure E, 0.040 g, 0.163 mmol), DL-aminoglutethimide (0.055 g, 0.237 mmol) in absolute ethanol (5 ml) was heated with stirring at 90° C. for 16 h. The reaction was diluted with ethanol and diethyl ether and the product collected by filtration to yield 0.038 g (54%) of the title compound. $^1$H NMR (DMSO-d$_6$): δ 11.00 (d,1H, J=12.5 Hz), 10.88 (s,1H), 10.83 (s,1H), 9.23 (s, H), 8.02 (d,1H, J=12.5 Hz), 7.77 (d,1H, J=8. 6 Hz), 7.42 (d,2H, J=8.9 Hz), 7.31 (d,2H, J=8.9 Hz), 7.09 (d,1H, J=8.2 Hz), 2.44–2.34 (m,2H), 2.15–2.13 (m,2H), 1.86–1.02 (m,2H), 0.75 (t,3H, J=7.3 Hz); ES-MS m/z 431 (M−H).

EXAMPLE 49

8-[(Z)-(4-Phenoxyanilino)methylidene]-6H-[1,3]thiazolo[5,4-e]indol-7-one

Prepared according to Procedure G with 4-phenoxyaniline in 86% yield. $^1$H NMR (DMSO-d$_6$): δ 11.02 (d,1H, J=12.5 Hz), 10.81 (s,1H), 9.22 (s,1H), 7.99 (d,1H, J=12.3 Hz), 7.76 (d,1H, J=8.42 Hz), 7.46 (d,2H, J=9.0 Hz) 7.37 (t,2H, J=7.9 Hz), 7.12–7.06 (m,4H), 6.98 (d,2H, J=8.1 Hz); ES-MS m/z 384 (M−H).

EXAMPLE 50

8{(Z)-[4-(Benzyloxy)anilino]methylidene}-6H-[1,3]thiazolo[5,4e]indol-7-one

Prepared according to Procedure G with 4-(benzyloxy)aniline in 90% yield. $^1$H NMR (DMSO-d$_6$): δ 10.96 (d,1H, J=12.5 Hz), 10.77 (s,1H), 9.21 (s,1H), 7.95 (d,1H, J=12.5 Hz), 7.74 (d,1H, J=8.4 Hz), 7.43 (d,2H, J=7.1 Hz), 7.39–7.35 (m,4H), 7.32–7.30 (m,1H), 7.09–7.04 (m,3H), 5.09 (s,2H); ES-MS m/z 398 (M−H).

EXAMPLE 51

Methyl 4-(4-{[((Z)-7-oxo-6,7-dihydro-8H-[1,3]thiazolo[5,4-e]indol-8-ylidene)methyl]amino}phenoxy)benzoate Prepared according to Procedure G with methyl 4-(4-aminophenoxy)benzoate in 35% yield. $^1$H NMR (DMSO-d$_6$): δ 11.05 (d,1H, J=12.3 Hz), 10.83 (s,1H), 9.22 (s,1H), 8.01 (d,1H, 12.3 Hz), 7.95–7.93 (m,2H), 7.77 (d,1H, J=8.4 Hz), 7.52 (d,2H, J=9.0 Hz), 7.19 (d,2H, J=8.8 Hz), 7.10 (d,1H, J=8.4 Hz), 7.03 (d,2H, J=8.8 Hz), 3.80 (s,3H); ES-MS m/z 442 (M−H).

EXAMPLE 52

Methyl 3-(4-{(Z)-[(7-oxo-4,7-dihydro-8H-[1,3]thiazolo[5,4-e]indol-8-ylidene)methyl]amino}phenoxy)benzoate Prepared according to Procedure G with methyl 3-(4-aminophenoxy)benzoate in 71% yield. $^1$H NMR (DMSO-d$_6$): δ 11.05 (d,1H, J=12.5 Hz), 10.82 (s,1H), 9.22 (s,1H), 8.01 (d,1H, J=12.3 Hz), 7.77(d,1H, J=8.4 Hz), 7.68 (d,1H, J=7.9 Hz), 7.55–7.49 (m,3H), 7.41 (s,1H), 7.31 (dd,1H, J=2.3,8.2 Hz), 7.14 (d,2H, J=8.8 Hz), 7.09 (d,1H, J=8.4 Hz), 3.08 (s,3H); ES-MS m/z 442 (M−H).

EXAMPLE 53

8-{(Z)-[3-(Hydroxymethyl)anilino]methylidene}-6H-[1,3]thiazolo[5,4-e]indol-7-one Prepared according to Procedure G with 3-(hydroxymethyl)aniline in 83% yield. $^1$H NMR (DMSO-d$_6$): δ 11.05 (d,1H, J=12. 5 Hz), 10.84 (s,1H), 9.23 (s,1H), 8.05 (d,1H, 12.3 Hz), 7.77 (d, 1H, J=8.4 Hz), 7.37–7.26 (m,3H), 7.10 (d,1H, J=8.4 Hz), 7.06 (d,1H, J=7.5 Hz), 5.27 (t,1H,J=5.7 Hz), 4.52 (d,2H, J=5.9 Hz); ES-MS m/z 322 (M−H).

EXAMPLE 54

3-{(Z)-[(7-Oxo-6,7-dihydro-8H-[1,3]thiazolo[5,4-e]indol-8-ylidene)methyl]amino}benzamide Prepared according to Procedure G with 3-aminobenzamide in 84% yield. $^1$H NMR (DMSO-d$_6$): δ 11.13 (d,1H, J=12.3 Hz), 10.87 (s,1H), 9.23 (s,1H), 8.12–8.07 (m,2H), 7.84 (s,1H), 7.78 (d,1H, J=8.4 Hz), 7.58 (t,2H, J=7.7 Hz), 7.47 (t,2H, J=7.8 Hz), 7.10 (d,1H, J=8.4 Hz); ES-MS m/z 335 (M−H).

EXAMPLE 55

8-{(Z)-[4-(5-Methyl-3-oxo-2,3-dihydro-1H-pyrazol-1-yl)anilino]methylidene}-6H-[1,3]thiazolo[5,4-e]indol-7-one A mixture of 8-dimethylamino-methylene-6,8-dihydro-1-thia-3,6-diaza-as-indacen-7-one (Procedure E, 0.040 g, 0.163 mmol), 2-(4-aminophenyl)-3-methyl-pyrazoline-5-one (0.047 g, 0.248 mmol) in absolute ethanol (5 ml) was heated with stirring at 90° C. for 16 h. The reaction was diluted with ethanol and diethyl ether and the product collected by filtration to yield 0.052 (83%) of the title compound. $^1$H NMR (DMSO-d$_6$): δ 11.08 (d,1H, J=12.3 Hz), 10.84 (s,1H), 9.85 (s,1H), 9.23 (s,1H), 8.05 (d,1H, J=12.1 Hz), 7.78 (d,1H, J=8.2 Hz), 7.51–7.45 (m,4H), 7.10 (d,1H, J=8.4Hz), 5.55 (s,1H), 2.25 (s,3H); ES-MS m/z 388 (M−H).

EXAMPLE 56

Methyl 4-{(Z)-[(7-oxo-6,7-dihydro-8H-[1,3]thiazolo[5,4-e]indol-8-ylidene)methyl]amino}benzoate Prepared according to Procedure G methyl 4-aminobenzoate in 47% yield. $^1$H NMR (DMSO-d$_6$): δ

11.17 (d,1H, J=12.1 Hz), 10.91 (s,1H), 9.25 (s,1H), 8.07 (d,1H, 12.1 Hz), 7.95 (d,2H, J=8.6 Hz), 7.81 (d,1H, J=8.2 Hz), 7.51(d,2H, J=8.6 Hz), 7.10 (d,1H, J=8.4 Hz), 3.81 (s,3H);ES-MS m/z 350 (M–H).

EXAMPLE 57

4-{(Z)-[(7-Oxo-6,7-dihydro-8H-[1,3]thiazolo[5,4-e]indol-8-ylidene)methyl]amino}benzonitrile Prepared according to Procedure G with 4-aminobenzonitrile in 71% yield. $^1$H NMR (DMSO-d$_6$): δ 11.14 (d,1H, J=11.9 Hz), 10.92 (s,1H), 9.25 (s,1H), 8.04 (d,1H, J=11.9 Hz), 7.82 (dd,3H, J=2.4, 8.7 Hz), 7.59 (d,2H, J=8.8 Hz), 7.10 (d,1 H, J=8.4 Hz); ES-MS m/z 317 (M–H).

EXAMPLE 58

N-Methyl-N-(4-{(Z)-[(7-oxo-6,7-dihydro-8H-[1,3]thiazolo[5,4-e]indol-8-ylidene)methyl]amino}phenyl)acetamide A mixture of 8-dimethylamino-methylene-6,8dihydro-1-thia-3,6-diaza-as-indacen-7-one (Procedure E, 0.040 g, 0.163 mmol), 4-amino-N-methylacetanilide (0.040 g, 0.244 mmol) in absolute ethanol (5 ml) was heated with stirring at 90° C. for 16 h. The reaction was diluted with ethanol and diethyl ether and the product collected by filtration to yield 0.038 g (64%) of the title compound. $^1$H NMR (DMSO-d$_6$): δ 11.03 (d,1 H, J=12.3 Hz), 10.84 (s,1H), 9.23 (s,1H), 8.02 (d,1H, J=12.3 Hz), 7.78 (d,1H, J=8.4 Hz), 7.48 (d,2H, J=8.2 Hz), 7.35 (d,2H, J=8.2 Hz), 7.09 (d,1H, J=8.4 Hz), 3.11 (s,3H), 1.76 (s, 3H); ES-MS m/z 363 (M–H).

EXAMPLE 59

1-[(Z)-(4-Phenoxyanilino)methylidene]-1,3-dihydro-2H-pyrrolo[3,2-f]quinolin-2-one Prepared according to Example 13 with 4-phenoxyaniline in 79% yield. $^1$H NMR (DMSO-d$_6$): δ 11.78 (d,1H, J=12.1 Hz), 10.93 (s,1H), 8.81–8.78 (m2H), 8.70 (d,1H, J=4.0 Hz), 7.70 (d,1H, J=8.6 Hz), 7.56 (d,2H, J=8.8 Hz), 7.45 (dd,1H, J=4.1, 8.5 Hz), 7.41–7.35 (m, 3H), 7.12–7.05 (m, 3H), 6.98 (d,2H, J=8.2 Hz); ES-MS m/z 378 (M–H).

Example 60

1-{(Z)-[4-(Benzyloxy)anilino]methylidene}-1,3-dihydro-2H-pyrrolo[3,2-f]quinolin-2-one Prepared according to Example 13 with 4-(benzyloxy)aniline in 59% yield. $^1$H NMR (DMSO-d$_6$): δ 11.80 (d,1H, J=12.3 Hz), 10.99 (s,1H), 8.95 (d,1H, J=8.1 Hz), 8.82–8.77 (m,2H), 7.73 (d,1H, J=8.8 Hz), 7.54 (dd,1H, J=4.1,8.3 Hz), 7.49–7.30 (m,8H), 7.05 (d,2H, J=9.0 Hz), 5.11 (s,2H), ES-MS m/z 394 (M+H).

EXAMPLE 61

Methyl 4-(4{(Z)-[(2-oxo-2,3-dihydro-1H-pyrrolo[3,2-f]quinolin-4-ylidene)methyl]amino}phenoxy)benzoate Prepared according to Example 13 with methyl 4-(4-aminophenoxy)benzoate in 69% yield. $^1$H NMR (DMSO-d$_6$): δ 11.80 (d,1H, J=12.1 Hz), 10.94 (s,1H), 8.83–8.80 (m,2H), 8.70 (d,1H, J=3.9 Hz), 7.95 (d,2H, J=8.8 Hz), 7.71 (d,1H, J=8.8 Hz), 7.62 (d,2H, J=9.0 Hz), 7.45 (dd,1H, J=4.1, 8.5 Hz), 7.41 (d, 1H, J=8.8 Hz), 7.18 (d,2H, J=8.8 Hz), 7.03 (d,2H, J=8.8 Hz), 3.80 (s,3H); ES-MS m/z 436 (M–H).

EXAMPLE 62

Methyl 3-(4{(Z)-[(2-oxo-2,3dihydro-1H-pyrrolo[3,2-f]quinolin-1-ylidene)methyl]amino}phenoxy)benzoate Prepared according to Example 13 with methyl 3-(4-aminophenoxy)benzoate in 45% yield. $^1$H NMR (DMSO-d$_6$): δ 11.96 (d,1H, J=12.1 Hz), 11.33 (s,1H), 9.44 (d,1H, J=8.2 Hz), 9.01–8.98 (m,2H), 7.95 (d,1H, J=8.8 Hz), 7.85 (dd,1H, J=4.9, 8.4 Hz), 7.72–7.66 (m,4H), 7.54 (t,1H, J=8.0 Hz), 7.42 (s,1H), 7.33 (d,1H, J=8.2 Hz), 7.17 (d,2H, J=8.6 Hz), 3.80 (s,3H); ES-MS m/z 438 (M+H).

EXAMPLE 63

3-Ethyl-3-(4-{(Z)-[(2-oxo-2,3-dihydro-1H-pyrrolo[3,2-f]quinolin-1-ylidene)methyl]amino}phenyl)-2,6-piperidinedione Prepared according to Example 13 with DL-aminoglutethimide in 81% yield. $^1$H NMR (DMSO-d$_6$): δ 11.72 (d,1H, J=11.7 Hz), 10.93 (s,1H), 10.88 (s,1H), 8.82–8.77 (m,2H), 8.70 (d,1H, J=2.9 Hz), 7.71 (d,1H, J=8.8 Hz), 7.52 (d,2H, J=8.8 Hz), 7.45 (dd,1H, J=4.1,8.5 Hz), 7.40 (d, 1H, J=8.8 Hz), 7.30 (d,2H, J=8.6 Hz), 2.36–2.16 (m,2H), 2.15–2.12 (m,2H), 1.90–1.77 (m,2H 0.76 (t,3H, J=7.3 Hz); ES-MS m/z 425 (M–H).

EXAMPLE 64

1-[(Z)-(4-Benzoylanilino)methylidene]-1,3-dihydro-2H-pyrrolo[3,2-f]quinolin-2-one Prepared according to Example 13 with 4-benzoylaniline in 76% yield. $^1$H NMR (DMSO-d$_6$): δ 11.92 (d,1H, J=11.7 Hz), 11.04 (s,1H), 8.88 (d,1H, J=11.7 Hz), 8.84 (d,1H, J=8.6 Hz), 8.73 (d,1H, J=3.1 Hz), 7.80–7.53 (m,10H), 7.49 (dd, 1H, J=4.1, 8.5 Hz), 7.42 (d,1H, J=8.8 Hz); ES-MS m/z 390 (M–H).

Example 65

1-{(Z)-[3-(Hydroxymethyl)anilino]methylidene}-1,3-dihydro-2H-pyrrolo[3,2-f]quinolin-2-one Prepared according to Example 13 with 3-(hydroxymethyl)aniline in 78% yield. $^1$H NMR (DMSO-d$_6$): δ 11.84 (d,1H, J=12.1 Hz), 10.36 (s,1H), 8.86–8.80 (m,2H), 8.72 (d,1H, J=4.0 Hz), 7.72 (d,1H, J=8.7 Hz), 7.48 (dd,1H, J=4.1,8.5 Hz), 7.43–7.33 (m,4H), 7.07 (d,1H, J=7.5 Hz), 5.25 (s,1H), 4.53 (dd,2H, J=4.5 Hz); ES-MS m/z 316 (M–H).

EXAMPLE 66

1-{(Z)-[4-(5-Methyl-3-oxo-2,3-dihydro-1H-pyrazol-1-yl)anilino]methylidene}-1H-pyrrolo[3,2-f]quinolin-2(3H)-one Prepared according to Example 13 with 2-(4-aminophenyl)-3-methyl-pyrazoline-5-one in 69% yield. $^1$H NMR (DMSO-d$_6$): δ 11.83 (d,1H, J=11.9 Hz), 10.05 (s,1H), 9.84 (s,1H), 8.86–8.82 (m,2H), 8.71 (d,$_1$H, J=2.9 Hz), 7.72 (d,1H, J=8.8 Hz), 7.60 (d,2H, J=8.8 Hz), 7.48–7.44 (m,3H), 7.41 (d,1H, J=8.8 Hz), 5.55 (s,1H), 2.25 (s,3H); ES-MS m/z 382 (M–H).

EXAMPLE 67

1-((E)-{4-[(E)-2-(4-Hydroxyphenyl)ethenyl]anilino}-methylidene)-1,3-dihydro-2H-pyrrolo[3,2-f]quinolin-2-one Prepared according to Example 13 with 2-(4-hydroxyphenyl)ethenyl]aniline in 90% yield. $^1$H NMR (DMSO-d$_6$): δ 11.86 (d,1H, J=11.9 Hz), 10.95 (s,1H), 9.53 (s,1H), 8.86–8.83 (m,2H), 8.71 (d,1H, J=3.3 Hz), 7.71 (d,1H, J=8.6 Hz), 7.58–7.45 (m,5H), 7.42–7.38 (m,3H), 7.12–6.98 (m,2H), 6.74 (d,2H, J=8.6 Hz); ES-MS m/z 404 (M–H).

Example 68

3{(Z)-[(2-Oxo-2,3-dihydro-1H-pyrrolo[3,2-f]quinolin-1-ylidene)methyl]amino}benzamide Prepared according to Example 13 with 3-aminobenzamide in 66% yield. $^1$H NMR (DMSO-d$_6$): δ 11.86 (d,1H, J=11.9 Hz), 10.98 (s,1H), 8.89–8.80 (m,2H), 8.72 (d,1H, J=2.9 Hz), 8.06 (s,1H), 7.88 (s,1H) 7.74–7.69 (m,2H), 7.59 (d,1H, J=7.7 Hz), 7.51–7.45 (m,3H), 7.41 (d,1H, J=8.8 Hz); ES-MS m/z 329 (M–H).

EXAMPLE 69

4-{(Z)-[(2-Oxo-2,3-dihydro-1H-pyrrolo[3,2-f]quinolin-1-ylidene)methyl]amino}benzonitrile Prepared according to Example 13 with 4-aminobenzonitrile in 82% yield. $^1$H NMR (DMSO-d$_6$): δ 11.84 (d,1H, J=11.7 Hz), 11.03 (s,1H), 8.84–8.73 (m,2H), 8.72 (dd,1H, J=1.2,4.1 Hz), 7.82 (d, 2H, J=8.6 Hz), 7.76 (d,1H, J=8.8 Hz), 7.69 (d,2H, J=8.8 Hz), 7.48 (dd,1H, J=4.1,8.5 Hz), 7.41 (d,1H, J=8.6 Hz); ES-MS m/z 311 (M–H).

EXAMPLE 70

Methyl 4-{(Z)-[(2-oxo-2,3dihydro-1H-pyrrolo[3,2-f]quinolin-1-ylidene)methyl]amino}benzoate Prepared according to Example 13 with methyl 4-aminobenzoate in 44% yield. $^1$H NMR (DMSO-d$_6$): δ 11.91 (d,1H, J=11.8 Hz), 11.03 (s,1H), 8.88–8.83 (m,2H), 8.72 (dd,1H,J=1.3,4.1 Hz), 7.95 (d,2H, J=8.6 Hz), 7.75 (d,1H, J=8.9 Hz), 7.63 (d,2H, J=8.6 Hz), 7.49 (dd,1H, J=3.9,8.6 Hz), 7.41 (d,1H, J=8.6 Hz), 3.82 (s,3H); ES-MS m/z 344 (M–H).

Example 71

8-[(Z)-(4-{[2-(Diethylamino)ethyl]sulfonyl}anilino)methylidene]-6H-[1,3]thiazolo[5,4-e]indol-7one Prepared according to Procedure G with 4-[2-(diethylamino)ethylsulfonyl]aniline in 18% yield. $^1$H NMR (DMSO-d$_6$): δ 11.20 (d,1H, J=11.9 Hz), 10.93 (s,1H), 9.26 (s1H), 8.08 (d,1H, J=11.9 Hz), 7.87 (d,2H, J=8.6 Hz), 7.82 (d,1H, J=8.42 Hz), 7.63 (d,2H, J=8.6 Hz), 7.11 (d,1H, J=8.24Hz), 3.46–3.38 (m,2H), 2.8–2.7 (m,2H), 2.3–2.2 (m,4H), 0.80 (t,6H, J=7.0 Hz); ES-MS m/z 455 (M–H).

EXAMPLE 72

1-[(Z)-(4-{[2-(Diethylamino)ethyl]sulfonyl}anilino)methylidene]-1H-pyrrolo[3,2-f]quinolin-2(3H)-one Prepared according to Example 13 with 4-[2-(diethylamino)ethylsulfonyl]aniline in 64% yield. $^1$H NMR (DMSO-d$_6$): δ 11.91 (d,1H, J=11.5 Hz), 11.04 (s,1H), 8.88–8.84 (m,2H), 8.73 (d, 1H, J=3.3 Hz), 7.87 (d,2H, J=8.6 Hz), 7.78–7.72 (m, 3H), 7.50 (dd,1H, J=4.1,8.5 Hz), 7.41 (d,1H, J=8.6 Hz), 3.45–3.38 (m,2H), 2.71–2.67 (m,2H), 2.32 (q,4H, J=7.0 Hz), 0.80 (t,6H, J=7.1 Hz); ES-MS m/z449 (M–H).

EXAMPLES 73–88

Are Described in Procedure J (vide infra)

EXAMPLE 89

3,6-Dihydro[1,2,3]triazolo[4,5e]indole-7,8-dione 8-[N-(4-methoxyphenyl)hydrazone]

See Procedure H.

EXAMPLE 90

3,6-Dihydro[1,2,3]triazolo[4,5-e]indole-7,8-dione 8-{N-4-(1,3-oxazol-5-yl)phenyl]hydrazone}

Prepared according to Procedure H with 4-(1,3-oxazol-5-yl)phenylhydrazine hydrochloride in 61% yield as ~2:1 mixture of geometric isomers. $^1$H NMR (DMSO-d$_6$): δ 7.09 and 7.26 (2 d, 1:2 ratio, J=8.6 Hz, 1H); 7.55 and 7.85 (ABq, J=8.7 Hz, 4H); 7.65 (s, 1H); 7.85 and 7.98 (2 d, 2:1 ratio, partially obscured by ABq, J=8.6 Hz, 1H); 8.45 (s, 1H); 10.87 and 11.33 (2 s, ~2:1 ratio, 1H). 12.95 (brd, 1H). APCI-MS m/z 344 (M–H)$^-$.

Example 91

3,6-Dihydro[1,2,3]triazolo[4,5-e]indole-7,8-dione 8-[N-(4-methylphenyl)hydrazone]

Prepared according to Procedure H with 4-methylphenylhydrazine hydrochloride in 18% yield as ~1:1 mixture of E and Z isomers. $^1$H NMR (DMSO-d$_6$): δ 2.28 (s, 3H); 7.19 (d, J=8.4 Hz, 0.5H); 7.15–7.35 (m, 3.5H); 7.62 (d, J=8.4 Hz, 1H); 7.76 (d, J=8.4 Hz, 0.5H); 7.93 (d, J=8.4 Hz, 0.5H); 10.7 (s, 0.5H); 11.2 (s, 1H); 12.3 and 12.35 2 s, 1H). APCI-MS m/z 291 (M–H)$^-$.

Example 92

3,6-Dihydro[1,2,3]triazolo[4,5-e]indole-7,8-dione 8-(N-{4-[(E)-2-(2-pyridinyl)ethenyl]phenyl}hydrazone)

Prepared according to Procedure H with 4'-hydrazino-2-stilbazole dihydrochloride (TCI, Inc.) in 89% yield as ~1:1 mixture of E and Z isomers as the hydrochloride salt. $^1$H NMR (DMSO-d$_6$): δ 7.10 and 7.26 (2 d, J=8.6 Hz, 1H); 7.37 and 7.41 (2 d, J=16 Hz, 1H); 7.55 (d, J=8.6 Hz, 1H); 7.68 (m, 1H); 7.74–7.9 (m, 3.5H); 7.99 (d, J=16 Hz, 1H); 7.99 (d, J=8.6 Hz, 0.5H); 8.16 (t, J=8.6 Hz, 1H); 8.34 (m, 1H); 8.74 (d, J=5.5 Hz, 1H); 10.9 and 11.4 (2 s, 1H); 13.0 (s, 1H). APCI-MS m/z 380 (M–H)$^-$.

EXAMPLE 93

6H-[1,3]Thiazolo[5,4-e]indole-7,8dione 8-[N-(3-methoxyphenyl)hydrazone]

Prepared according to Procedure H using 6H-[1,3]thiazolo[5,4-e]indole-7,8-dione (Procedure A) and 3-methoxyphenylhydrazine hydrochloride in 44% yield. APCI-MS m/z 323 (M–H)$^-$.

EXAMPLE 94

5-Hydroxy-4,6-dimethyl-1H-indole-2,3-dione 3-[N-(4-methylphenyl)hydrazone]

5-Hydroxy-4,6-dimethyl-1H-indole-2,3-dione was prepared from 3,5-dimethyl-4-hydroxyaniline according to Procedure A: $^1$H NMR (DMSO-d$_6$): δ 2.17 (s, 3H), 2.30 (s, 3H), 6.45 (s, 1H), 8.29 (s, 1H), 10.65 (s, 1H); ESI-MS m/z 190 (M−H)$^-$. The isatin was combined with 4-methylphenylhydrazine hydrochloride according to Procedure H to provide the title compound in 41% yield. $^1$H NMR (DMSO-d6): δ 2.15 (s, 3H), 2.24 (s, 3H), 2.43 (s, 3H), 6.46 (s, 1H), 7.16 (m, 4H), 7.88 (s, 1H), 10.64 (s, 1H 12.85 (s, 1H). APCI-MS m/z 294 (M−H, 45%).

Example 95

(Z)-3,6-Dihydro[1,2,3]triazolo[4,5-e]indole-7,8-dione 8-{N-[4-(trifluoromethyl)phenyl]hydrazone}

Prepared according to Procedure H with 4-trifluoromethylphenylhydrazine hydrochloride in 32% yield. $^1$H NMR (DMSO-d$_6$): δ 7.26 (d, J=8.7 Hz, 1H); 7.59 and 7.83 (ABq, J=8.4 Hz, 4H); 7.89 (brd d, J=8.7 Hz, 1H); 10.9 (s, 1H); 13.0 (s, 1H). APCI-MS m/z 345 (M−H)$^-$.

EXAMPLE 96

6H-[1,3]Thiazolo[5,4-e]indole-7,8dione 8-[N-(3-fluorophenyl)hydrazone](Z-isomer)

6H-1-Thia-3,6-diaza-as-indacen-7,8-dione (Procedure A, 50 mg, 0.25 mmol) was combined with 3-fluorophenylhydrazine hydrochloride (50 mg, 0.3 mmol) in 2 ml of ethanol and heated at 70° C. for 6 hrs. The product was collected by filtration of the hot solution, washing with ethanol and diethyl ether, to give 47 mg (60%) of the title compound as a brown solid. $^1$H NMR (DMSO-d$_6$): δ 6.82 (t, J=8.7 Hz, 1H); 7.10 (d, J=8.6 Hz, 1H); 7.37 (m, 2H); 7.41 (dd, 1H); 7.97 (d, J=8.6 Hz, 1H); 9.25 (s, 1H); 11.2 (s, 1H). ES-MS m/z 311 (M−1)$^-$.

EXAMPLE 97

(Z)-6H-[1,3]Thiazolo[5,4-e]indole-7,8-dione 8-[N-(4-fluorophenyl)hydrazone]

Prepared according to Example 96 with 6H-1-thia-3,6-diaza-as-indacen-7,8-dione (Procedure A) and 4-fluorophenylhydrazine hydrochloride in 49% yield. $^1$H NMR (DMSO-d$_6$): δ 7.11 (d, J=8.6 Hz, 1H); 7.25 (t, J=8.8 Hz, 2H); 7.52 (dd, J=4.8, 8.8 Hz, 2H); 7.94 (d, J=8.6 Hz, 1H); 9.27 (s, 1H); 11.2 (s, 1H); 12.6 (s, 1H). ES-MS m/z 311 (M−1)$^-$.

EXAMPLE 98

(Z)-6H-[1,3]Thiazolo[5,4-e]indole-7,8-dione 8-[N-(4-bromophenyl)hydrazone]

Prepared according to Example 96 with 6H-1-thia-3,6-diaza-as-indacen-7,8-dione (Procedure A) and 4-bromophenylhydrazine hydrochloride in 62% yield. $^1$H NMR (DMSO-d$_6$): δ 7.16 (d, J=8.5 Hz, 1H); 7.50 and 7.62 (Abq, J=8.8 Hz, 4H); 8.02 (d, J=8.5 Hz, 1H); 9.33 (s, 1H); 11.3 (s, 1H); 12.6 (s, 1H). ES-MS m/z 371, 373 (M−1)$^-$.

Procedure J—Method for preparation of a solution phase library containing compounds of the invention Set forth below are a selected number of synthesis examples that illustrate the solution library techniques that can be used to obtain the compounds of the invention. It is believed that One of ordinary skill in the art can follow this procedure or modify it accordingly without undue experimentation in order to obtain the substitutions disclosed above. The following examples are illustrative examples of the solution phase synthesis, not intended to limit the scope of the invention in any way.

Synthesis of Intermediates

5-Bromo-7-azaoxindole a) 3,3,5 Tribromooxindole

A solution of 3,3-dibromo-7-azaoxindole (5.0 g, 13.4 mmol) in tert-BuOH (100 mL) and water (100 mL) is stirred at room temperature and bromine (5.5 g, 34.3 mmol) is added dropwise over 20 min. A saturated aqueous solution of sodium bicarbonate (approx. 15 mL) is added dropwise over 30 min to raise the pH of the solution to 6.5. The yellow solid formed is collected by filtration. The filtrate is condensed to approx. 100 mL and extracted with CHCl$_3$ (2×50 mL). The combined organic extracts are dried over anhydrous magnesium sulfate and the solvent is evaporated under reduced pressure to leave a yellow solid. The solids are combined and dried under vacuum to give 3,3,5 tribromooxindole as a yellow solid, 6.25 g (98%). $^1$H NMR (CDCl$_3$) δ 9.4 (br s, 1H), 8.28 (d, 1H, J=2 Hz), 7.95 (d, 1H, J=2 Hz).

b) 5-Bromo-7-azaoxindole

A solution of 3,3,5-tribromooxindole (5.0 g, 13.4 mmol) in fresh THF (100 mL) is stirred at room temperature and a saturated aqueous solution of ammonium chloride (100 mL) is added. The flask is placed in a water bath and activated zinc dust (15.0 g, 230 mmol) is added. The mixture is stirred for 20 min and the zinc is removed by filtration through a pad of diatomaceous earth. The organic layer is separated and the aqueous layer is extracted with THF (20 mL). The combined organic layers were washed with saturated brine solution, dried over anhydrous magnesium sulfate and the solvent removed under reduced pressure. The brown residue is triturated with water (20 mL) and the tan solid is collected by filtration and dried under vacuum to give 5-bromo-7-azaoxindole as a tan solid, 2.02 g (71%). $^1$H NMR (DMSO-d$_6$) δ 11.13 (s, 1H), 8.15 (s, 1H), 8.76 (s, 1H), 3.57 (s, 2H). MS (AP −ve) 211 (100) (M−H).

5-Phenyl-7-azaoxindole

To a stirred mixture of 5-bromo-7-azaoxindole (213 mg, 1 mmol) and phenylboronic acid (183 mg, 1.5 mmol) in toluene (6 ml) and ethanol (6 ml) were added 1 M sodium carbonate solution (2.5 ml, 2.5 mmol), lithium chloride (127 mg, 3 mmol) and dichlorobis(triphenylphosphine)palladium (II) (35 mg, 0.05 mmol) under N$_2$ atmosphere. The reaction mixture was heated to reflux at 95° C. for 18 hours. The reaction mixture was diluted with chloroform (50 ml) and washed with brine (20 ml). The aqueous layer was thoroughly extracted with chloroform. The combined organic layers were dried over anhydrous MgSO$_4$, filtered and evaporated under vacuum to give crude product. Trituation of the crude product with diethyl ether yielded 5-phenyl-7-azaoxindole as a yellow solid (108 mg, 51.4%). $^1$H NMR (DMSO-d$_6$): δ 11.04 (s, 1H), 8.32 (s, 1H), 7.83 (s, 1H), 7.60 (d, 2H, J=7.4 Hz), 7.44 (t, 2H, J=7.4 Hz), 7.32 (t, 1H, J=7.4 Hz), 3.58 (s, 2H). MS (−ve APCI): 210 (48, M$^+$), 209 (100, M−H).

5-(Furan-2-yl)-7-aza-oxindole

5-Bromo-7-azaoxindole (0.75 g, 3.52 mmol), 2-tributyltinfuran (1.26 g, 3.52 mmol), tetraethylammonium chloride hydrate (1.94 g, 10.6 mmol) were combined and dissolved in acetonitrile (10 mL) at room temperature under an atmosphere of nitrogen. Bistriphenylphosphine dichloropalladium (II) (0.25 g, 0.35 mmol) was added and the reaction was warmed to 85° C. for 16 h. The reaction was cooled to room temperature and diluted with aqueous KF (10%, 60 mL). This was stirred for 20 minutes and then diluted with EtOAc (60 mL). The biphasic system was passed through celite, the layers separated, and the volatiles removed in vacuo. The resulting residue was triturated with diethyl ether and the solids were collected by filtration to afford a light yelow solid (0.28 g, 36% yield). 1H NMR 300 MHz (DMSO-d$_6$) δ 11.18 (bs, 1H); 8.45 (s, 1H); 7.92 (s, 1H); 7.79 (s, 1H); 6.95 (d, 1H); 6.60 (d, 1H); 3.64 (s, 2H). APCI m/z 201 (M+1).

5-(3-Thienyl)-7-aza-oxindole

5-Bromo-7-azaoxindole (0.20 g, 0.94 mmol), 3-tributyltinthiophene (0.42 g, 1.12 mmol), tetraethylammonium chloride hydrate (0.16 g, 0.94 mmol) were combined and dissolved in acetonitrile (10 mL) at room temperature under nitrogen. Bistriphenylphosphine dichloropalladium (II) (0.033 g, 0.047 mmol) was added and the reaction was warmed to 85° C. for 20 h. Fresh catalyst was added to the reaction mixture, Bistriphenylphosphine dichloropalladium (II) (0.033 g, 0.047 mmol) and the reaction continued to stir at 85° C. for 24 h. The reaction was cooled to room temperature and diluted with water (20 mL) and EtOAc (20 ml). The biphasic system was passed through celite and the layers were separated. he organic layer was washed with brine (10 mL) and dried over sodium sulfate. The volatiles ere removed in vacuo. The resulting residue was triturated with diethyl ether and collected by filtration (0.16 g, 80% yield).). 1H NMR 400 MHz (DMSO-d$_6$) δ 11.03 (bs, 1H); 8.43 (s, 1H); 7.92 (s, 1H); 7.84 (s, 1H); 7.60 (m, 1H); 7.53 (d, 1H); 3.58 (s, 2H).

5-Carboethoxy-7-azaoxindole

To a mixture of 5-bromo-7-azaoxindole (213 mg, 1 mmol) in dimethylsulfoxide (1 ml) and ethanol (5 ml) in Parr bomb were added triethylamine (0.31 ml, 2.25 mmol), palladium acetate (33.7 mg, 0.15 mmol), and 1,3-(bisdiphenylphosphino)propane (61.9 mg, 0.15 mmol). Carbon monoxide gas (40 atm) was applied and the reaction mixture was heated at 95° C. for 18 hours with vigorously stirring. The reaction mixture was diluted with diethyl ether (50 ml) and washed with water (10 ml). The aqueous layer was thoroughly extracted with diethyl ether. The combined organic layers were dried over anhydrous MgSO$_4$, filtered and evaporated under vacuum to give crude product. Trituation of the crude product with methanol yielded 5-(carboethoxy)-7-azaoxindole as a tan solid (53 mg, 25.7%). $^1$H NMR (DMSO-d$_6$): δ 11.39 (s, 1H), 8.62 (s, 1H), 7.95 (s, 1H), 4.27 (q, 2H, J=7 Hz), 3.59 (s, 2H), 1.28 (t, 3H, J=7 Hz). MS (−ve APCI): 205 (4, M−H).

6-Chloro-7-azaoxindole a) 6-Chloro-7-aza-3,3-dibromooxindole

6-Chloro-7-azaindole was prepared according to the procedure of Minakata et al; Synthesis, 1992, 661–663. To a stirred solution of 1.32 g (8.7 mmol) of 6-chloro-7-azaindole in tert-butanol (80 mL) was added 9.9 g (28 mmol) of 90% pyridine hydrobromide perbromide reulting in a thick yellow precipitate forming immediately. The reaction was concentrated and the crude chromatographed on silica gel eluting with hexane to 90% hexane/10% EtOAc gradient to give 2.36 g of the title compound as a white solid, containing about 30% of 5-bromo-6-chloro-7-aza-3,3-dibromooxindole as an inseparable impurity. $^1$H NMR (CDCl$_3$) δ 7.16 (d, J=8.0 Hz, 1H), 7.81 (d, J=8.0 Hz, 1H), 9.0 (bs, 1H). (5-Bromo-6-chloro-7-aza-3,3- dibromooxindole, 8.05 (s, 1H), 9.0 (bs, 1H).

b) 6-Chloro-7-azaoxindole

A solution of 2.36 g (7.26 mmol) of the mixture of 6-chloro-7-aza-3,3-dibromooxindole and 5-bromo-6-chloro-7-aza-3,3-dibromooxindole in THF (70 mL) and saturated ammonium chloride solution (70 mL) was treated with 6 g (92 mmol) of powdered zinc. After stirring for 2 h another 6 g (92 mmol) portion of zinc was added and stirring continued another 2 h. The zinc was filtered off and washed with ether. Ether phase separated and the aqueous phase washed twice with a 1:1 mixture of THF/ether. Combined ether fractions were dried over magnesium sulfate, filtered and concentrated. The crude was loaded onto 7.5 g of silica gel and chromatographed on silica gel eluting with 90% hexane/10% ethyl acetate to a 66% hexane/33% ethyl acetate gradient to give 0.647 g of the title compound, plus 0.243 g of 5-bromo-6-chloro-7-azaoxindole. $^1$H NMR (DMSO-d$_6$): δ 3.57 (s, 2H), 7.04 (d, J=7.6 Hz, 1H), 7.61 (d, J=7.6 Hz, 1H), 11.2 (bs, 1H).

7-Azaoxindole a) 3,3-Dibromo-7-azaoxindole

A solution of 7-azaindole (4.0 g, 34 mmol) in tert-BuOH (200 mL) is stirred at room temperature and pyridinium perbromide (32.5 g, 0.1 mol) is added in portions over 30 min. and the reaction mixture is stirred for 3 h. Pyridinium perbromide (10.8 g, 33 mmol) is added and the mixture is stirred for a further 2 h. The tert-BuOH is evaporated under educed pressure and the residue is partitioned between water (300 mL) and EtOAc (300 mL). The organic layer is separated and the aqueous layer is extracted with EtOAc. The combined organic layers are washed with water (2×50 mL), and brine. The organic layer is dried over anhydrous MgSO$_4$, filtered and the solvent evaporated. Trituration of the residue with CH2Cl2 gives a white solid which is collected by filtration and dried under vacuum to give 3,3-dibromo-7-azaoxindole, 8.35 g. $^1$H-NMR (DMSO-d$_6$) δ 11.99 (s, 1H), 8.21 (dd, 1H, J=5.1, 1.5 Hz), 8.00 (dd, 1H, J=7.5, 1.5 Hz), 7.17 (dd, 1H, J=7.5, 5.1 Hz). MS (+ve ES) 293 (28), (M+H), 147 (100).

b) 7-Azaoxindole

A solution of 3,3-dibromo-7-azaoxindole (2.0 g, 7.2 mmol) in THF (50 mL) is stirred at room temperature and a saturated aqueous solution of NH$_4$Cl is added. Activated zinc powder is added and the reaction mixture is stirred for 2 h. The zinc is removed by filtration through a pad of diatomaceous earth and the organic layer is separated. The aqueous layer is extracted with THF (10 mL) and the combined organic layers are dried over anhydrous MgSO$_4$, filtered and evaporated. The residue is slurried in 10:1 CHCl3:MeOH (15 mL) and filtered through a pad of silica gel and the filtrate is evaporated. The residue is triturated with water and the solid is collected by filtration and dried under vacuum to give 7-azaoxindole, 0.668 g (70%). $^1$H NMR (DMSO-d$_6$) δ 10.94 (s, 1H), 8.02 (d, 1H, J=5.2 Hz), 7.52 (d, 1H, J=6.8 Hz), 6.90 (dd, 1H, J=6.8, 5.2 Hz), 3.53 (s, 2H). MS(AP−ve) 133 (100) (M−H)

4-Aza-oxindole a) Diethyl (3-nitropyridin-2-yl)-malonate

Sodium hydride (60% dispersion in oil, 5.57 g, 0.14 mol) was carefully washed with hexanes under nitrogen before the addition of DMSO (115 mL). Diethyl malonate (22.3 g, 0.14 mol) was added dropwise over 20 min and the mixture was stirred for an additional 30 min at room temperature. 2-Chloro-3-nitropyridine (10 g, 0.06 mol) was added to the reaction and the reaction was placed in a pre-heated oil bath set to 100° C. for 15 min. The reaction was cooled to room temperature and poured into aqueous ammonium chloride (saturated solution, 150 mL). The aqueous solution was extracted with EtOAc:Hexanes (1:1) four times (200 mL each) and the organic layers were combined. The organics were concentrated to afford a solid that was recrystallized from a minimal amount of EtOAc:Hexanes (1:1) (12.5 g, 70% yield). APCI MS m/z 281 (M−1).

b) Ethyl 2-(3-nitro-pyridin-2-yl)-acetate

Diethyl (3-nitropyridin-2-yl)-malonate (12.5 g, 0.044 mol) was dissolved in DMSO (150 mL) and water (0.79 mL, 0.044 mol) and lithium chloride (4.65 g, 0.11 mol) were added at room temperature under nitrogen. The reaction was warmed to 100° C. 12 h and more lithium chloride (1 g) was added to the reaction. The reaction was heated for another 5 hours and cooled to room temperature. Brine (150 mL) was added to the reaction before extracting with EtOAc (3×, 275 mL each). The organics were combined and dried over sodium sulfate, then concentrated in vacuo. The resulting residue was triturated with diethyl ether and collected by filtration (8.6 g, 92% yield). 1H NMR 400 MHz (DMSO-d6) δ 8.83 (m, 1H); 8.53 (m, 1H); 7.65 (m, 1H); 4.23 (s, 2H); 4.07 (m, 2H); 1.16 (m, 3H).

c) Ethyl 2-(3-amino-pyridin-2-yl)-acetate

Under an atmosphere of nitrogen, Pd/C (10%, 1.36 g) was charged to a round bottome flask. Ethyl 2-(3-nitro-pyridin-2-yl)-acetate (8.6 g, 0.41 mol) was dissolved in ethanol (200 mL) and added to the reaction vessel. The reaction was placed under an atmosphere of hydrogen and stirred at room temperature for 30 min. The reaction was filtered through celite and the filtrate was concentrated in vacuo to afford the product as a tan solid (6.94 g, 94% yield).

d) 4-Azaoxindole

Ethyl 2-(3-amino-pyridin-2-yl)-acetate (6.94 g, 0.038 mol) was dissolved in diethyl ether (100 mL) at room temperature. Hydrochloric acid (2M, 35 mL) was added and the reaction was stirred for 30 minutes. The volatiles were removed to afford a brown solid that was re-crystallized from ethanol and diethyl ether (4.0 g, 62% yield). 1H NMR 400 MHz (DMSO-d$_6$) δ 12.35 (s, 1H); 8.12 (m, 1H); 7.90 (m, 1H); 7.14 (m, 1H); 5.75 (s, 2H). Electrospray MS m/z 135 (M+1).

6-(Furan-2-yl)oxindole

6-Bromo-oxindole (0.40 g, 1.88 mmol), 2-tributyltinfuran (0.71 mL, 2.26 mmol), and tetraethylammonium chloride hydrate (0.31 g, 1.88 mmol) were combined and dissolved in acetonitrile (15 mL). The palladium catalyst, bistriphenylphosphinedichloropalladium (II) (0.66 g, 0.09 mmol) was added and the reaction was warmed to 85° C. under nitrogen for 20 h. The reaction was cooled to room temperature and diluted with water (15 mL) before passing the mixture through celite. The pad of celite was washed with EtOAc and the filtrates were combined and separated. The aqueous layer was washed with EtOAc (2×20 mL each). The combined organic phases were washed with brine and dried over sodium sulfate. The volatiles ere removed in vacuo. The resulting residue was triturated with diethyl ether and the solid was collected by filtration (0.13 g, 34%). $^1$H NMR 300 MHz (DMSO-d6) δ 10.5 (s, 1H); 7.75 (s, 1H); 7.30 (m, 2H); 7.11 (s, 1H); 6.91 (m, 1H); 6.60 (m, 1H); 3.52 (s, 2H).

Synthesis of Monomers

Monomer 6: 5-Carboethoxy-3-ethoxymethylene-7-azaoxindole (Procedure J-1)

5-Carboethoxy-7-azaoxindole (0.040 g, 0.19 mmol) and diethoxymethylacetate (0.16 mL, 0.97 mmol) were combined and dissolved in acetic acid (1 mL). The reaction was warmed to 110° C. and stirred at this temperature for 1 h. The reaction was cooled to room temperature and diethyl ether was added to precipitate a beige solid that was collected by filtration (35 mg, 69% yield). $^1$H NMR 400 MHz (DMSO-d6) δ 11.30 (s, 1H); 8.58 (s, 1H); 8.05 (s, 1H); 7.93 (s, 1H); 4.44 (m, 2H); 4.28 (m, 2H); 1.35 (m, 3H); 1.28 (m, 3H).

Monomer 7: 3-Dimethylaminomethylene-6-phenyloxindole (Procedure J-2)

6-Phenyloxindole (0.053 mg, 0.25 mmol) and dimethylformamide di-t-butylacetal (0.08 mL, 0.32 mmol) were combined and dissolved in DMF. The reaction mixture was stirred at room temperature for 4 hours. The volatiles were removed in vacuo and the resulting residue was triturated with diethyl ether. The solids were collected by filtration (50 mg, 75% yield). ). $^1$H NMR 400 MHz (DMSO-d6) mixture of E and Z isomers: δ 10.09 (s, 1H); 10.02 (s, 1H); 7.59–7.51 (m, 4H); 7.45–7.22 (m, 10H); 7.10–7.05 (m, 2H); 6.98 (s, 1H); 6.91 (s, 1H); 3.29 (s, 12H).

Monomer 1: 3-Ethoxymethylene-5-phenyl-7-azaoxindole

Synthesized according to Procedure J-1. $^1$H NMR 400 MHz (DMSO-d6) δ 10.93 (s, 1H); 8.24 (s, 1H); 7.86–7.82 (m, 2H); 7.62–7.56 (m, 2H); 7.44 (m, 2H); 7.34 (m, 1H); 4.40 (m, 2H); 1.35 (m, 3H).

Monomer 2: 3-Ethoxymethylene-5-(2-furanyl)-7-azaoxindole

Synthesized according to Procedure J-1. $^1$H NMR 400 MHz (DMSO-d6) δ 10.96 (s, 1H); 8.36 (s, 1H); 7.87–7.84 (m, 2H); 7.72 (s, 1H); 6.87 (d, 1H); 6.56 (m, 1H); 4.42 (m, 2H); 1.36 (m, 3H).

Monomer 3: 3-Ethoxymethylene-5-(3-thienyl)-7-azaoxindole

Synthesized according to Procedure J-1. $^1$H NMR 400 MHz (DMSO-d6) δ 10.89 (s, 1H); 8.33 (s, 1H); 7.88 (s, 1H); 7.84 (s, 1H); 7.79 (s, 1H); 7.62 (m, 1H); 7.49 (d, 1H); 4.40 (m, 2H); 1.36 (m, 3H).

Monomer 4: 5-Bromo-3-ethoxymethylene-7-azaoxindole

Synthesized according to Procedure J-1. $^1$H NMR 400 MHz (DMSO-d6) δ 11.02 (s, 1H); 8.07 (s, 1H); 7.88 (s, 1H); 7.71 (s, 1H); 4.40 (m, 2H); 1.34 (m, 3H).

Monomer 5: 6-Chloro-3-ethoxymethylene-7-azaoxindole

Synthesized according to Procedure J-1. $^1$H NMR 400 MHz (DMSO-d6) δ 11.06 (s, 1H); 7.84 (s, 1H); 7.63 (d, 1H); 6.98 (d, 1H); 4.39 (m, 2H); 1.32 (m, 3H).

Monomer 8: 3-Dimethylaminomethylene-6-(2-furanyl)oxindole

Synthesized according to Procedure J-2. $^1$H NMR 400 MHz (DMSO-d6) mixture of E and Z isomers: δ 10.10 (s, 1H); 10.03 (s, 1H); 7.64 (s, 1H); 7.61 (s, 1H); 7.56 (s, 1H); 7.38 (s, 1H); 7.37 (d, 1H); 7.26 (d, 1H); 7.14 (s, 1H); 7.12 (s, 1H); 7.03 (s, 1H); 6.96 (s, 1H); 6.72 (d, 1H); 6.67 (d, 1H); 6.52 (s, 1H); 6.49 (s, 1H); 3.29 (s, 12H)

Monomer 9: 3-Dimethylaminomethylene-7-azaoxindole

This monomer was generated in situ (during library synthesis) from 7-aza-oxindole and dimethylformamide di-t-butylacetal in DMF.

Monomer 10: 3-Dimethylaminomethylene4-azaoxindole

This monomer was generated in situ (during library synthesis) from 4-aza-oxindole and dimethylformamide di-t-butylacetal in DMF.

Representative Amine Monomers are shown in Table 6.

| Monomer Code | Structure |
|---|---|
| A | 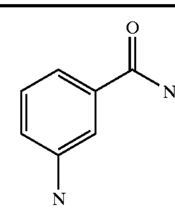 |

| Monomer Code | Structure |
|---|---|
| B | 4-aminobenzenesulfonamide |
| C | 5-amino-3-phenyl-1-methylpyrazole |
| D | diethyl 4-aminobenzylphosphonate |
| E | 3-aminobenzonitrile |
| F | 4-amino-1-naphthol |
| G | 2-(2-aminophenyl)ethanol |
| H | (3-aminophenyl)methanol |
| I | 1-ethyl-5-amino-pyrazole |
| J | 6-aminoquinoline |
| K | 2-methoxyaniline |
| L | 2-aminobenzimidazole |
| M | 6-aminoindazole |
| N | 3-methyl-1-(4-aminophenyl)-5-pyrazolone |
| O | 5-amino-2-morpholinopyridine |
| P | 4-iodoaniline |

Solution Phase Library Synthesis

Stock solutions (0.037M) were prepared for each set of monomers. For example, 35 mg of Monomer 1 was dissolved in 3.5 mL of ethanol. Each monomer was prepared in a separate solution and carefully labeled 1 through 8. For the amine set, a slight excess of stock solution was prepared. For example, 20.4 mg was dissolved in 4.0 mL of methanol. Each amine as prepared in a separate solution and carefully labeled A through P.

Monomer 9 and Monomer 10 were generated in situ by preparing stock solutions of the corresponding aza-oxindole. For example, 20.1 mg of 4-aza-oxindole was dissolved in 4.0 mL of ethanol. Both of the precursors for monomers 9 and 10 were transferred (0.20 ml/well) to a 96-well dry heating block (vwrBRAND Dry Block Heater, cat #13259-066) according to the map below where M represents the monomer and A represents the amine. The ethanol was evaporated off at 50° C. until it was clear that there was no solvent remaining. DMF (0.20 mL) was added followed by the addition of dimethylformamide di-t-butylacetal (0.003 mL) and this remained at room temperature for 1 h.

Monomers 1 through 8 (0.20 mL/well) were transferred to the appropriate wells in the dry block heater according to the plate map below. After the in situ conversion of monomer 9 and 10 was complete, the aniline set (0.20 mL/well) was transferred to the appropriate wells according to the plate map below. The plates were heated to 70° C. for 4 h and then the reaction was cooled to 40° C. and heating was continued for another 16 h. Ethanol was added as necessary to keep a constant reaction volume in the wells.

| Plate 1 | | | | | | | | | |
|---|---|---|---|---|---|---|---|---|---|
| M1-AA | M1-AI | M2-AA | M2-AI | M3-AA | M3-AI | M4-AA | M4-AI | M5-AA | M5-AI |
| M1-AB | M1-AJ | M2-AB | M2-AJ | M3-AB | M3-AJ | M4-AB | M4-AJ | M5-AB | M5-AJ |
| M1-AC | M1-AK | M2-AC | M2-AK | M3-AC | M3-AK | M4-AC | M4-AK | M5-AC | M5-AK |
| M1-AD | M1-AL | M2-AD | M2-AL | M3-AD | M3-AL | M4-AD | M4-AL | M5-AD | M5-AL |
| M1-AE | M1-AM | M2-AE | M2-AM | M3-AE | M3-AM | M4-AE | M4-AM | M5-AE | M5-AM |
| M1-AF | M1-AN | M2-AF | M2-AN | M3-AF | M3-AN | M4-AF | M4-AN | M5-AF | M5-AN |
| M1-AG | M1-AO | M2-AG | M2-AO | M3-AG | M3-AO | M4-AG | M4-AO | M5-AG | M5-AO |
| M1-AH | M1-AP | M2-AH | M2-AP | M3-AH | M3-AP | M4-AH | M4-AP | M5-AH | M5-AP |

| Plate 2 | | | | | | | | | |
|---|---|---|---|---|---|---|---|---|---|
| M6-AA | M6-AI | M7-AA | M-7AI | M8-AA | M8-AI | M9-AA | M9-AI | M10-AA | M10-AI |
| M6-AB | M6-AJ | M7-AB | M7-AJ | M8-AB | M8-AJ | M9-AB | M9-AJ | M10-AB | M10-AJ |
| M6-AC | M6-AK | M7-AC | M7-AK | M8-AC | M8-AK | M9AC | M9-AK | M10-AC | M10-AK |
| M6-AD | M6-AL | M7-AD | M7-AL | M8-AD | M8-AL | M9-AD | M9-AL | M10-AD | M10-AL |
| M6-AE | M6-AM | M7-AE | M7-AM | M8-AE | M8-AM | M9-AE | M9-AM | M10-AE | M10-AM |
| M6-AF | M6-AN | M7-AF | M7-AN | M8-AF | M8-AN | M9-AF | M9-AN | M10-AF | M10-AN |
| M6-AG | M6-AO | M7-AG | M7-AO | M8-AG | M8-AO | M9-AG | M9-AO | M10-AG | M10-AO |
| M6-AH | M6-AP | M7-AH | M7-AP | M8-AH | M8-AP | M9-AH | M9-AP | M10-AH | M10-AP |

Upon completion of the reaction, methanol (1.0 mL) was added to each well. Using a multi-pipettor, the contents of the reaction wells were transferred to the appropriate wells of a 96-well (Beckmann) plate. The volatiles were removed using a nitrogen flow to substantially reduce the volume of solvent, followed by placing the plates in a vacuum drying oven at 70° C. under 15 mmHg of pressure. The average weight of product determined for plate 1 was 1.91 mg/well (70% conversion). The average weight of product determined for plate 2 was 1.78 mg/mL (70% conversion). All of the wells were analysed by LC-MS.

A Micromass Platform II mass spectrometer equipped with an electrospray ion source was used to acquire low resolution LC-MS data for the samples. The system software runs on a PC computer with the Microsoft operating system, and consists of Masslynx v3.1 and Openlynx v3.1 software packages. The mass spectrometer inlet system was comprised of a Hewlett Packard 1100 HPLC Chromatograph, a Gilson 215 autosampler, and a Hewlett Packard 1100 photo-diode array detector. A Supelco ABZ+ 5 cm column was used to provide separations prior to electrospray ionization. The HPLC was programmed as follows:

| Time | % A | % B | Flow Rate |
|---|---|---|---|
| 0.0 min | 85 | 15 | 0.6 ml/min |
| 3.0 min | 25 | 75 | 0.6 ml/min |
| 4.0 min | 0 | 100 | 0.6 ml/min |
| 5.0 min | 0 | 100 | 0.6 ml/min |

The data were processed automatically using standard peak detection parameters provided by the Openlynx software.

A Micromass LCT bench-top mass spectrometer equipped with an electrospray ionization source was used to obtain accurate mass (high resolution) data. The LCT utilizes two hexapole RF lenses to transfer ions from the source to an orthogonal acceleration time-of-flight (TOF) analyser. The ions emerging from the analyser are detected using a dual microchannel plate detector and ion counting system. The system software runs on a PC computer with the Microsoft operating system, and consists of Masslynx v3.2 and Openlynx v3.2 software packages. The mass spectrometer inlet system is comprised of a Waters Alliance 2690 Separations Module, Waters 2700 autosampler, Waters 996 photo-diode array detector and Valco column switching device. A mobile phase flow rate of 1 ml/min exits the Alliance 2690 and is reduced to a mass spectrometer flow rate of 20 ul/min using an Acurate flow splitter. A lock mass solution at a flow rate of 4 ul/min is added to the spectrometer flow via a Harvard syringe pump and a tee piece placed immediately before the electrospray probe. The instrument resolution was determined by acquiring a spectrum and measuring the full peak width t half peak height (FWHH). The instrument was tuned to provide a resolution of 4600 to 5000 (FWHH). The instrument was calibrated using the ions of polyethylene glycol (PEG) as reference standards. The lock mass used [3,5-Dil-Tyr, Ala,N-Me-Phe, Gly-0I] Enkephalin (MH+$C_{26}H_{34}I_2N_5O_6$=766.0599) at a concentration of 5 ng/$\mu$l.

Following are examples of the invention prepared in the solution phase library with accompanying high resolution or low resolution mass spectral data.

EXAMPLE 73

3-{[(Z and E)-(2-Oxo-6-phenyl-1,2-dihydro-3H-indol-3-ylidene)methyl]amino}benzamide. Accurate mass M+H=356.1388 (mmu error 1.0)

EXAMPLE 74

Diethyl 4-{[(Z and E)-(2-oxo-6-phenyl-1,2-dihydro-3H-indol-3-ylidene)methyl]amino}benzylphosphonate. Accurate mass M+H= 463.1952 (mmu error 3.4)

EXAMPLE 75

3-{[(Z and E)-(2-Oxo-6-phenyl-1,2-dihydro-3H-indol-3-ylidene)methyl]amino}benzonitrile. Accurate mass M+H=338.1289 (mmu error 0.3)

EXAMPLE 76

3-{(Z and E)-[2-(2-Hydroxyethyl)anilino]methylidene}-6-phenyl-1,3-dihydro-2H-indol-2-one. Accurate mass M+H 357.1595 (mmu error 0.7)

EXAMPLE 77

3-{(Z and E)-[3-(Hydroxymethyl)anilino]methylidene}-6-phenyl-1,3-dihydro-2H-indol-2-one. Accurate mass M+H=343.1438 (mmu error 0.7)

EXAMPLE 78

3-[(Z and E)-(2-Methoxyanilino)methylidene]-6-phenyl-1,3-dihydro-2H-indol-2-one. Accurate mass M+H=343.1442 (mmu error 0.3)

EXAMPLE 79

3-{(Z and E)-[4-(5-Methyl-3-oxo-2,3-dihydro-1H-pyrazol-1-yl)anilino]methylidene}-6-phenyl-1H-indol-2-one. Accurate mass M+H=409.1645 (mmu error 1.9)

EXAMPLE 80

3-[(Z and E)-(4-Iodoanilino)methylidene]-6-phenyl-1H-indol-2-one. Accurate mass M+H=439.0246 (mmu error 1.9)

EXAMPLE 81

3-({(Z and E)-6-(2-Furyl)-2-oxo-1,2-dihydro-3H-indol-3-ylidene]methyl}amino)benzamide. Accurate mass M+H=346.1188 (mmu error 0.2)

EXAMPLE 82

Diethyl 4-({(Z and E)-[6-(2-furyl)-2-oxo-1,2-dihydro-3H-indol-3-ylidene]methyl}amino)benzylphosphonate. Accurate mass M+H=453.1755 (mmu error 2.3)

EXAMPLE 83

3-({(Z and E)-[6-(2-Furyl)-2-oxo-1,2-dihydro-3H-indol-3-ylidene]methyl}amino)benzonitrile. LC-ES-MS (M+H)=328

EXAMPLE 84

6-(2-Furyl)-3-{(Z and E)-[2-(2-hydroxyethyl)anilino]methylidene}-1,3-dihydro-2H-indol-2-one. Accurate mass M+H=347.1377 (mmu error 1.7)

EXAMPLE 85

6-(2-Furyl)-3-{(Z and E)-[3-(hydroxymethyl)anilino]methylidene)-1,3-dihydro-2H-indol-2-one. Accurate mass M+H=333.1227 (mmu error 1.0)

EXAMPLE 86

6-(2-Furyl)-3-[(Z and E)-(2-methoxyanilino)methylidene]-1,3-dihydro-2H-indol-2-one. Accurate mass M+H=333.1234 (mmu error 0.4)

EXAMPLE 87

6-(2-Furyl)-3-{(Z and E)-[4-(5-methyl-3-oxo-2,3-dihydro-1H-pyrazol-1-yl)anilino]methylidene}-1H-indol-2-one. Accurate mass M+H=399.1444 (mmu error 1.1)

EXAMPLE 88

6-(2-Furyl)-3-[(Z and E)-(4-iodoanilino)methylidene]-1H-indol-2-one. Accurate mass M+H=429.0031 (mmu error 2.7)

EXAMPLE 99

3-{[(2-Oxo-5-phenyl-1,2-dihydro-3H-pyrrolo[2,3-b]pyridin-3-ylidene)methyl]amino}benzamide. Accurate mass M+H=357.1339 (mmu error 1.2)

EXAMPLE 100

Diethyl 4-{[(2-oxo-5-phenyl-1,2-dihydro-3H-pyrrolo[2,3-b]pyridin-3-ylidene)methyl]amino}benzylphosphonate. Accurate mass M+H=464.1918 (mmu error 2.0)

EXAMPLE 101

3-{[(2-Oxo-5-phenyl-1,2-dihydro-3H-pyrrolo[2,3-b]pyridin-3-ylidene)methyl]amino}benzonitrile. Accurate mass M+H=339.1237 (mmu error 0.8)

Example 102

3-{[2-(2-Hydroxyethyl)anilino]methylidene}-5-phenyl-1,3-dihydro-2H-pyrrolo[2,3-b]pyridin-2-one. Accurate mass M+H=358.1534 (mmu error 2.1)

EXAMPLE 103

3-{[3-(Hydroxymethyl)anilino]methylidene}-5-phenyl-1,3-dihydro-2H-pyrrolo[2,3-b]pyridin-2-one. Accurate mass M+H=344.1377 (mmu error 2.1)

EXAMPLE 104

3-[(2-Methoxyanilino)methylidene]-5-phenyl-1,3-dihydro-2H-pyrrolo[2,3-b]pyridin-2-one. Accurate mass M+H=344.1386 (mmu error 1.2)

EXAMPLE 105

3-{[4-(5-Methyl-3-oxo-2,3-dihydro-1H-pyrazol-1-yl)anilino]methylidene}-5-phenyl-1H-pyrrolo[2,3-b]pyridin-2-one. Accurate mass M+H=410.1597 (mmu error 1.9)

EXAMPLE 106

3-[(4-Iodoanilino)methylidene]-5-phenyl-1H-pyrrolo[2,3b]pyridin-2-one. Accurate mass M+H=440.0218 (mmu error 0.0)

EXAMPLE 107

3-({[5-(2-Furyl)-2-oxo-1,2-dihydro-3H-pyrrolo[2,3-b]pyridin-3-ylidene]methyl}amino)benzamide. Accurate mass M+H=347.1135 (mmu error 0.8)

EXAMPLE 108

Diethyl 4-({[5-(2-furyl)-2-oxo-1,2-dihydro-3H-pyrrolo[2,3-b]pyridin-3-ylidene]methyl}amino)benzylphosphonate. Accurate mass M+H 454.1724 (mmu error 0.7)

EXAMPLE 109

3-({[5-(2-Furyl-2-oxo-1,2-dihydro-3H-pyrrolo[2,3-b]pyridin-3-ylidene]methyl}amino)benzonitrile. Accurate mass M+H=329.1017 (mmu error2.1)

EXAMPLE 110

5-(2-Furyl)-3-{[2-(2-hydroxyethyl)anilino]methylidene}-1,3-dihydro-2H-pyrrolo[2,3-b]pyridin-2-one. Accurate mass M+H=348.1333 (mmu error 1.4)

EXAMPLE 111

5-(2-Furyl)-3-{[3-(hydroxymethyl)anilino]methylidene}-1,3-dihydro-2H-pyrrolo[2,3-b]pyridin-2one. Accurate mass M+H=334.1168 (mmu error 2.3)

EXAMPLE 112

5-(2-Furyl)-3-[(2-methoxyanilino)methylidene]-1,3-dihydro-2H-pyrrolo[2,3-b]pyridin-2-one. Accurate mass M+H=334.1177 (mmu error 1.4)

EXAMPLE 113

5-(2-Furyl)-3-{[4-(5-methyl-3-oxo-2,3-dihydro-1H-pyrazol-1-yl)anilino]methylidene}-1H-pyrrolo[2,3-b]pyridin-2-one. Accurate mass M+H=400.1394 (mmu error 1.5)

EXAMPLE 114

5-(2-Furyl)-3-[(4-iodoanilino)methylidene]-1H-pyrrolo[2,3-b]pyridin-2-one. Accurate mass M+H= 430.0008 (mmu error 0.3)

EXAMPLE 115

3-({[2-Oxo-5-(3-thienyl)-1,2-dihydro-3H-pyrrolo[2,3-b]pyridin-3-ylidene]methyl}amino)benzamide. Accurate mass M+H=363.0903 (mmu error 1.2)

EXAMPLE 116

Diethyl 4-({[2-oxo-5-(3-thienyl)-1,2-dihydro-3H-pyrrolo[2,3-b]pyridin-3-ylidene]methyl}amino)benzylphosphonate. Accurate mass M+H=470.1497 (mmu error 0.6)

EXAMPLE 117

3-({[2-Oxo-5-(3-thienyl)-1,2-dihydro-3H-pyrrolo[2,3-b]pyridin-3-ylidene]methyl}amino)benzonitrile. Accurate mass M+H=345.0800 (mmu error 0.9)

EXAMPLE 118

3-[{2-(2-Hydroxyethyl)anilino]methylidene}-5-(3-thienyl)-1,3-dihydro-2H-pyrrolo[2,3-b]pyridin-2-one. Accurate mass M+H=364.1098 (mmu error 2.1)

EXAMPLE 119

3-[{3-(Hydroxymethyl)anilino]methylidene}-5-(3-thienyl)-1,3-dihydro2H-pyrrolo[2,3-b]pyridin-2-one. Accurate mass M+H=350.0959 (mmu error 0.4)

EXAMPLE 120

3-[(2-Methoxyanilino)methylidene]-5-(3-thienyl)-1,3-dihydro-2H-pyrrolo[2,3-b]pyridin-2-one. Accurate mass M+H=350.0946 (mmu error 1.7)

EXAMPLE 121

3-{[4-(5-Methyl-3-oxo-2,3-dihydro-1H-pyrazol-1-yl)anilino]methylidene}-5-(3-thienyl)-1,3-dihydro-2H-pyrrolo[2,3-b]pyridin-2-one. Accurate mass M+H=416.1172 (mmu error 0.8)

EXAMPLE 122

3-[(4-Iodoanilino)methylidene]-5-(3-thienyl)-1H-pyrrolo[2,3-b]pyridin-2-one. Accurate mass M+H= 445.9771 (mmu error 1.2)

EXAMPLE 123

3-{[(5-Bromo-2-oxo-1,2-dihydro-3H-pyrrolo[2,3-b]pyridin-3-ylidene)methyl]amino}benzamide. Accurate mass M+H=359.0134 (mmu error 0.9)

EXAMPLE 124

Diethyl 4-{[(5-Bromo-2-oxo-1,2-dihydro-3H-pyrrolo[2,3-b]pyridin-3-ylidene)methyl]amino}benzylphosphonate. Accurate mass M+H= 466.0730 (mmu error 0.0)

EXAMPLE 125

3-{[(5-Bromo-2-oxo-1,2-dihydro-3H-pyrrolo[2,3-b]
pyridin-3-ylidene)methyl]amino}benzonitrile.
Accurate mass M+H=341.0033 (mmu error 0.4)

EXAMPLE 126

5-Bromo-3-{[2-(2-hydroxyethyl)anilino]
methylidene}-1,3-dihydro-2H-pyrrolo[2,3-b]pyridin-
2-one. Accurate mass M+H=360.0337 (mmu error
1.0)

EXAMPLE 127

5-Bromo-3-{[3-(hydroxymethyl)anilino]
methylidene}-1,3-dihydro-2H-pyrrolo[2,3-b]pyridin-
2-one. Accurate mass M+H=346.0176 (mmu error
1.4)

EXAMPLE 128

5-Bromo-3-[(2-methoxyanilino)methylidene]-1,3-
dihydro-2H-pyrrolo[2,3-b]pyridin-2-one. Accurate
mass M+H=346.0169 (mmu error 2.1)

EXAMPLE 129

5-Bromo-3-{[4-(5-methyl-3-oxo-2,3-dihydro-1H-
pyrazol-1-yl)anilino]methylidene}-1,3-dihydro-2H-
pyrrolo[2,3-b]pyridin-2-one. Accurate mass M+H=
412.0388 (mmu error 2.0)

EXAMPLE 130

5-Bromo-3-[(4-iodoanilino)methylidene]-1H-pyrrolo
[2,3-b]pyridin-2-one. Accurate mass M+H=
441.9002 (mmu error 0.8)

EXAMPLE 131

3-{[(6-Chloro-2-oxo-1,2-dihydro-3H-pyrrolo[2,3-b]
pyridin-3-ylidene)methyl]amino}benzamide.
Accurate mass M+H=315.0633 (mmu error 1.5)

EXAMPLE 132

Diethyl 4-{[(6-chloro-2-oxo-1,2-dihydro-3H-pyrrolo
[2,3-b]pyridin-3-ylidene)methyl]
amino}benzylphosphonate. Accurate mass M+H=
422.1234 (mmu error 0.2)

EXAMPLE 133

3-{[(6-Chloro-2-oxo-1,2-dihydro-3H-pyrrolo[2,3-b]
pyridin-3-ylidene)methyl]amino}benzonitrile.
Accurate mass M+H=297.0532 (mmu error 1.0)

EXAMPLE 134

6-Chloro-3-{[2-(2-hydroxyethyl)anilino]
methylidene}-1,3-dihydro-2H-pyrrolo[2,3-b]pyridin-
2-one. Accurate mass M+H=316.0836 (mmu error
1.6)

EXAMPLE 135

6-Chloro-3-{[3-(hydroxymethyl)anilino]
methylidene}-1,3-dihydro-2H-pyrrolo[2,3-b]pyridin-
2-one. Accurate mass M+H=302.0683 (mmu error
1.3)

EXAMPLE 136

6-Chloro-3-[(2-methoxyanilino)methylidene]-1,3-
dihydro-2H-pyrrolo[2,3-b)pyridin-2-one. Accurate
mass M+H=302.0667 (mmu error 2.9)

EXAMPLE 137

6-Chloro-3-{[4-(5-methyl-3-oxo-2,3-dihydro-1H-
pyrazol-1-yl)anilino]methylidene}-1,3-dihydro-2H-
pyrrolo[2,3-b]pyridin-2-one. Accurate mass M+H=
368.0894 (mmu error 1.9)

EXAMPLE 138

6-Chloro-3-[(4-iodoanilino)methylidene]-1H-pyrrolo
[2,3-b]pyridin-2-one. Accurate mass M+H=
397.9504 (mmu error 1.2)

EXAMPLE 139

Ethyl 3-{[3-(aminocarbonyl)anilino]methylidene}-
2-oxo-2,3-dihydro-1H-pyrrolo[2,3-b]pyridine-5-
carboxylate. Accurate mass M+H=353.1242 (mmu
error 0.7)

EXAMPLE 140

Ethyl 3-({4-[(diethoxyphosphoryl)methyl]
anilino}methylidene)-2-oxo-1,2-dihydro-3H-pyrrolo
[2,3-b]pyridine-5-carboxylate. Accurate mass M+
H=460.1826 (mmu error 1.0)

EXAMPLE 141

Ethyl 3-[(3-cyanoanilino)methylidene]-2-oxo-2,3-
dihydro-1H-pyrrolo[2,3-b]pyridine-5-carboxylate.
Accurate mass M+H=335.1127 (mmu error 1.6)

EXAMPLE 142

Ethyl 3-[2-(2-hydroxyethyl)anilino]methylidene)-2-
oxo-2,3-dihydro-1H-pyrrolo[2,3-b]pyridine-5-
carboxylate. Accurate mass M+H=354.1434 (mmu
error 1.9)

EXAMPLE 143

Ethyl 3-{[3-(hydroxymethyl)anilino]methylidene}-
2-oxo-2,3-dihydro-1H-pyrrolo[2,3-b]pyridine-5-
carboxylate. Accurate mass M+H=340.1287 (mmu
error 0.9)

EXAMPLE 144

Ethyl 3-[(2-methoxyanilino)methylidene]-2-oxo-2,3-
dihydro-1H-pyrrolo[2,3-b]pyridine-5-carboxylate.
Accurate mass M+H=340.1285 (mmu error 1.1)

EXAMPLE 145

Ethyl 3-{[4-(5-methyl-3-oxo-2,3-dihydro-1H-pyrazol-1-yl)anilino]methylidene}-2-oxo-1,2-dihydro-3H-pyrrolo[2,3-b]pyridine-5-carboxylate. Accurate mass M+H=406.1499 (mmu error 1.5)

EXAMPLE 146

Ethyl 3-[(4-iodoanilino)methylidene]-2-oxo-1,2-dihydro-3H-pyrrolo[2,3-b]pyridine-5-carboxylate. Accurate mass M+H=436.0103 (mmu error 1.3)

EXAMPLE 147

3-{[(2-Oxo-1,2-dihydro-3H-pyrrolo[2,3-b]pyridin-3-ylidene)methyl]amino}benzamide. Accurate mass M+H=281.1024 (mmu error 1.4)

EXAMPLE 148

Diethyl 4-{[(2-oxo-1,2-dihydro-3H-pyrrolo[2,3-b]pyridin-3-ylidene)methyl]amino}benzylphosphonate. Accurate mass M+H= 388.1607(mmu error 1.8)

EXAMPLE 149

3-{[(2-Oxo-1,2-dihydro-3H-pyrrolo[2,3-b]pyridin-3-ylidene)methyl]amino}benzonitrile. Accurate mass M+H=263.0923 (mmu error 0.9)

EXAMPLE 150

3-{[2-(2-Hydroxyethyl)anilino]methylidene}-1,3-dihydro-2H-pyrrolo[2,3-b]pyridin-2-one. Accurate mass M+H=282.1229 (mmu error 1.2)

EXAMPLE 151

3-{[3-(Hydroxymethyl)anilino]methylidene}-1,3-dihydro-2H-pyrrolo[2,3-b]pyridin-2-one. Accurate mass M+H=268.1082 (mmu error 0.3)

EXAMPLE 152

3-[(2-Methoxyanilino)methylidene]-1,3-dihydro-2H-pyrrolo[2,3-b]pyridin-2-one. Accurate mass M+H= 268.1082 (mmu error 0.3)

EXAMPLE 153

3-{[4-(5-Methyl-3-oxo-2,3-dihydro-1H-pyrazol-1-yl)anilino]methylidene}-1H-pyrrolo[2,3-b]pyridin-2-one. Accurate mass M+H=334.1301 (mmu error 0.2)

EXAMPLE 154

3-[(4-Iodoanilino)methylidene]-1H-pyrrolo[2,3-b]pyridin-2-one. Accurate mass M+H=363.9898 (mmu error 0.7)

EXAMPLE 155

3-{[(2-Oxo-1,2-dihydro-3H-pyrrolo[3,2-b]pyridin-3-ylidene)methyl]amino}benzamide. Accurate mass M+H=281.1035 (mmu error 0.3)

EXAMPLE 156

Diethyl 4-{[(2-oxo-1,2dihydro-3H-pyrrolo[3,2-b]pyridin-3-ylidene)methyl]amino}benzylphosphonate. LC-ES-MS (M+H)=388

EXAMPLE 157

3-{[(2-Oxo-1,2-dihydro-3H-pyrrolo[3,2-b]pyridin-3-ylidene)methyl]amino}benzonitrile. Accurate mass M+H=263.0912 (mmu error 2.0)

EXAMPLE 158

3-{[2-(2-Hydroxyethyl)anilino]methylidene}-1,3-dihydro-2H-pyrrolo[3,2-b]pyridin-2-one. Accurate mass M+H=282.1241 (mmu error 0.0)

EXAMPLE 159

3-{[3-(Hydroxymethyl)anilino]methylidene}-1,3-dihydro-2H-pyrrolo[3,2-b]pyridin-2-one. Accurate mass M+H=268.1079 (mmu error 0.6)

EXAMPLE 160

3-[(2-Methoxyanilino)methylidene]-1,3-dihydro-2H-pyrrolo[3,2-b]pyridin-2-one. Accurate mass M+H= 268.1083 (mmu error 0.2)

EXAMPLE 161

3-{[4-(5-Methyl-3-oxo-2,3-dihydro-1H-pyrazol-1-yl)anilino]methylidene}-1H-pyrrolo[3,2-b]pyridin-2-one. Accurate mass M+H=334.1301 (mmu error 0.2)

EXAMPLE 162

3-[(4-Iodoanilino)methylidene]-1H-pyrrolo[3,2-b]pyridin-2-one. Accurate mass M+H=363.9896 (mmu error 0.9)

EXAMPLE 163

3-{(Z and E)-[(1-methyl-3-phenyl-1H-pyrazol-5-yl)amino]methylidene}-5-phenyl-1,3dihydro-2H-pyrrolo[2,3-b]pyridin-2one. Accurate mass M+H= 394.1645 (mmu error 2.2)

EXAMPLE 164

3{(Z and E)-[(4-Hydroxy-1-naphthyl)amino]methylidene}-5-phenyl-1,3-dihydro-2H-pyrrolo[2,3-b]pyridin-2one. Accurate mass M+H=380.1388 (mmu error 1.0)

EXAMPLE 165

3-{(Z and E)-[(1-Ethyl-1H-pyrazol-5-yl)amino]methylidene}-5-phenyl-1,3-dihydro-2H-pyrrolo[2,3-b]pyridin-2-one. Accurate mass M+H=332.1508 (mmu error 0.3)

EXAMPLE 166

3-[(Z and E)-(1H-Benzimidazol-2-ylamino)methylidene]-5-phenyl-1H-pyrrolo[2,3-b]pyridin-2-one. Accurate mass M+H=354.1336 (mmu error 1.8)

EXAMPLE 167

3-((Z and E)-{[6-(4-Morpholinyl)-3-pyridinyl]amino}methylidene)-5-phenyl-1,3-dihydro-2H-pyrrolo[2,3-b]pyridin-2-one. Accurate mass M+H=400.1754 (mmu error 1.9)

EXAMPLE 168

5-(2-Furyl)-3{(Z and E)-[(1-methyl-3-phenyl-1H-pyrazol-5-yl)amino]methylidene}-1,3-dihydro-2H-pyrrolo[2,3-b]pyridin-2-one. Accurate mass M+H=384.1455 (mmu error 0.5)

EXAMPLE 169

5-(2-Furyl)-3-{(Z and E)-[(4-hydroxy-1-naphthyl)amino]methylidene}-1,3-dihydro-2H-pyrrolo[2,3-b]pyridin-2-one. Accurate mass M+H=370.1189 (mmu error 0.2)

EXAMPLE 170

3-{(Z and E)-[(1-Ethyl-1H-pyrazol-5-yl)amino]methylidene}-5-(2-furyl)-1,3-dihydro-2H-pyrrolo[2,3-b]pyridin-2-one. Accurate mass M+H=322.1297 (mmu error 0.6)

EXAMPLE 171

3-[(Z and E)-(1H-Benzimidazol-2-ylamino)methylidene]-5-(2-furyl)-1H-pyrrolo[2,3-b]pyridin-2-one. LC-ES-MS (M+H)=344.

EXAMPLE 172

5-(2-Furyl)-3-((Z and E)-{[6-(4-morpholinyl)-3-pyridinyl]amino}methylidene)-1,3-dihydro-2H-pyrrolo[2,3-b]pyridin-2-one. Accurate mass M+H=390.1556 (mmu error 0.9)

EXAMPLE 173

3-{(Z and E)-[(1-Methyl-3-phenyl-1H-pyrazol-5-yl)amino]methylidene}-5-(3-thienyl)-1,3-dihydro-2H-pyrrolo[2,3-b]pyridin-2-one. Accurate mass M+H=400.1231 (mmu error 0.0)

EXAMPLE 174

3{(Z and E)-[(4-Hydroxy-1-naphthyl)amino]methylidene}-5-(3-thienyl)-1,3-dihydro-2H-pyrrolo[2,3-b]pyridin-2-one. Accurate mass M+H=386.0960 (mmu error 0.3)

EXAMPLE 175

3-{(Z and E)-[(1-Ethyl-1H-pyrazol-5-yl)amino]methylidene}-5-(3-thienyl)-1,3-dihydro-2H-pyrrolo[2,3-b]pyridin-2-one. Accurate mass M+H=338.1060 (mmu error 1.5)

EXAMPLE 176

3-[(Z and E)-(1H-Benzimidazol-2-ylamino)methylidene]-5-(3-thienyl)-1,3-dihydro-2H-pyrrolo[2,3-b]pyridin-2-one. Accurate mass M+H=360.0915 (mmu error 0.3)

EXAMPLE 177

3-((Z and E)-{[6-(4-Morpholinyl)-3-pyridinyl]amino}methylidene)-5-(3-thienyl)-1,3-dihydro-2H-pyrrolo[2,3-b]pyridin-2-one. Accurate mass M+H=406.1321 (mmu error 1.6)

EXAMPLE 178

5-Bromo-3-{(Z and E)-[(1-methyl-3-phenyl-1H-pyrazol-5-yl)amino]methylidene}-1,3-dihydro-2H-pyrrolo[2,3-b]pyridin-2-one. Accurate mass M+H=396.0442 (mmu error 1.7)

EXAMPLE 179

5-Bromo-3-{(Z and E)-[(4-hydroxy-1-naphthyl)amino]methylidene}-1,3-dihydro-2H-pyrrolo[2,3-b]pyridin-2-one. Accurate mass M+H=382.0187 (mmu error 0.3)

EXAMPLE 180

5-Bromo-3-{(Z and E)-[(1-ethyl-1H-pyrazol-5-yl)amino]methylidene}-1,3-dihydro-2H-pyrrolo[2,3-b]pyridin-2-one. Accurate mass M+H=334.0297 (mmu error 0.5)

EXAMPLE 181

3-[(Z and E)-(1H-Benzimidazol-2-ylamino)methylidene]-5-bromo-1,3-dihydro-2H-pyrrolo[2,3-b]pyridin-2-one. Accurate mass M+H=356.0134 (mmu error 1.2)

EXAMPLE 182

5-Bromo-3-((Z and E)-{[6-(4-morpholinyl)-3-pyridinyl]amino}methylidene)-1,3-dihydro-2H-pyrrolo[2,3-b]pyridin-2-one. Accurate mass M+H=402.0556 (mmu error 0.8)

EXAMPLE 183

6-Chloro-3-{(Z and E)-[(1-methyl-3-phenyl-1H-pyrazol-5-yl)amino]methylidene}-1,3-dihydro-2H-pyrrolo[2,3-b]pyridin-2-one. Accurate mass M+H= 352.0957 (mmu error 0.7)

EXAMPLE 184

6-Chloro-3-{(Z and E)-[(4-hydroxy-1-naphthyl)amino]methylidene}-1,3-dihydro-2H-pyrrolo[2,3-b]pyridin-2-one. Accurate mass M+H=338.0669 (mmu error 2.7)

EXAMPLE 185

6-Chloro-3-{(Z and E)-[(1-ethyl-1H-pyrazol-5-yl)amino]methylidene}-1,3-dihydro-2H-pyrrolo[2,3-b]pyridin-2-one. Accurate mass M+H=290.0808 (mmu error 0.0)

EXAMPLE 186

3-[(Z and E)-(1H-Benzimidazol-2-ylamino)methylidene]-6-chloro-1,3-dihydro-2H-pyrrolo[2,3-b]pyridin-2-one. Accurate mass M+H=312.0633 (mmu error 1.8)

EXAMPLE 187

6-Chloro-3-((Z and E)-{[6-(4-morpholinyl)-3-pyridinyl]amino}methylidene)-1,3-dihydro-2H-pyrrolo[2,3-b]pyridin-2-one. Accurate mass M+H= 358.1053 (mmu error 1.7)

EXAMPLE 188

Ethyl 3-{(Z and E)-[(1-methyl-3-phenyl-1H-pyrazol-5-yl)amino]methylidene}-2-oxo-2,3-dihydro-1H-pyrrolo[2,3-b]pyridine-5-carboxylate. Accurate mass M+H=390.1556 (mmu error 0.9)

EXAMPLE 189

Ethyl 3-{(Z and E)-[(4-hydroxy-1-naphthyl)amino]methylidene}-2-oxo-2,3-dihydro-1H-pyrrolo[2,3-b]pyridine-5-carboxylate. Accurate mass M+H= 376.1289 (mmu error 0.7)

EXAMPLE 190

Ethyl 3-{(Z and E)-[(1-ethyl-1H-pyrazol-5-yl)amino]methylidene}-2-oxo-2,3-dihydro-1H-pyrrolo[2,3-b]pyridine-5-carboxylate. Accurate mass M+H=328.1403 (mmu error 0.5)

EXAMPLE 191

Ethyl 3-[(Z and E)-(1H-benzimidazol-2-ylamino)methylidene]-2-oxo-1,2-dihydro-3H-pyrrolo[2,3-b]pyridine-5-carboxylate. Accurate mass M+H= 350.1241 (mmu error 1.1)

EXAMPLE 192

Ethyl 3-((Z and E)-{[6-(4-morpholinyl)-3-pyridinyl]amino}methylidene)-2-oxo-2,3dihydro-1H-pyrrolo[2,3-b]pyridine-5-carboxylate. Accurate mass M+H=396.1655 (mmu error 1.6)

EXAMPLE 193

3-{(Z and E)-[(1-Methyl-3-phenyl-1H-pyrazol-5-yl)amino]methylidene}-6-phenyl-1,3-dihydro-2H-indol-2-one. Accurate mass M+H=393.1691 (mmu error 2.3)

EXAMPLE 194

3-{(Z and E)-[(4-Hydroxy-1-naphthyl)amino]methylidene}-6-phenyl-1,3-dihydro-2H-indol-2-one. Accurate mass M+H=379.1430 (mmu error 1.5)

EXAMPLE 195

3-{(Z and E)-[(1-Ethyl-1H-pyrazol-5-yl)amino]methylidene}-6-phenyl-1,3-dihydro-2H-indol-2-one. Accurate mass M+H=331.1552 (mmu error 0.6)

EXAMPLE 196

3-[(Z and E)-(1H-Benzimidazol-2-ylamino)methylidene]-6-phenyl-1H-indol-2-one. Accurate mass M+H=353.1388 (mmu error 1.4)

EXAMPLE 197

3-((Z and E)-{[6-(4-Morpholinyl)-3-pyridinyl]amino}methylidene)-6-phenyl-1,3-dihydro-2H-indol-2-one. Accurate mass M+H=399.1809 (mmu error 1.1)

EXAMPLE 198

6-(2-Furyl-3-{(Z and E)-(1-methyl-3-phenyl-1H-pyrazol-5-yl)amino]methylidene}-1,3-dihydro-2H-indol-2-one. Accurate mass M+H=383.1498 (mmu error 0.9)

EXAMPLE 199

6-(2-Furyl)-3-{(Z and E)-[(4-hydroxy-1-naphthyl)amino]methylidene}-1,3-dihydro-2H-indol-2-one

EXAMPLE 200

3-{(Z and E)-[(1-Ethyl-1H-pyrazol-5-yl)amino]methylidene}-6-(2-furyl)-1,3-dihydro-2H-indol-2-one. Accurate mass M+H=321.1342 (mmu error 0.8)

EXAMPLE 201

3-[(Z and E)-(1H-Benzimidazol-2-ylamino)methylidene]-6-(2-furyl)-1H-indol-2-one. Accurate mass M+H=343.1192 (mmu error 0.2)

EXAMPLE 202

6-(2-Furyl)-3-((Z and E)-{[6-(4-morpholinyl)-3-pyridinyl]amino}methylidene)-1,3-dihydro-2H-indol-2-one. Accurate mass M+H=389.1604 (mmu error 0.8)

EXAMPLE 203

3-{(Z and E)-[(1-Methyl-3-phenyl-1H-pyrazol-5-yl)amino]methylidene}-1,3-dihydro-2H-pyrrolo[2,3-b]pyridin-2-one. Accurate mass M+H=318.1347 (mmu error 0.6)

EXAMPLE 204

3-{(Z and E)-[(4-Hydroxy-1-naphthyl)amino]methylidene}-1,3-dihydro-2H-pyrrolo[2,3-b]pyridin-2-one

EXAMPLE 205

3-{(Z and E)-[(1-Ethyl-1H-pyrazol-5-yl)amino]methylidene}-1,3-dihydro-2H-pyrrolo[2,3-b]pyridin-2-one. Accurate mass M+H=256.1195 (mmu error 0.2)

EXAMPLE 206

3-[(Z and E)-(1H-Benzimidazol-2-ylamino)methylidene]-1H-pyrrolo[2,3-b]pyridin-2-one

EXAMPLE 207

3-((Z and E)-{-[6-(4-Morpholinyl)-3-pyridinyl]amino}methylidene)-1,3-dihydro-2H-pyrrolo[2,3-b]pyridin-2-one. A ccurate mass M+H=324.1453 (mmu error 0.7)

EXAMPLE 208

3-{(Z and E)-[(1-Methyl-3-phenyl-1H-pyrazol-5-yl)amino]methylidene}-1,3-dihydro-2H-pyrrolo[3,2-b]pyridin-2-one. Accurate mass M+H=318.1347 (mmu error 0.7)

EXAMPLE 209

3-{(Z and E)-[(4-Hydroxy-1-naphthyl)amino]methylidene}-1,3-dihydro-2H-pyrrolo[(3,2-b]pyridin-2-one

EXAMPLE 210

3-{(Z and E)-[(1-Ethyl-1H-pyrazol-5-yl)amino]methylidene}-1,3-dihydro-2H-pyrrolo[3,2-b]pyridin-2-one. Accurate mass M+H=256.1178 (mmu error 1.9)

EXAMPLE 211

3-[(Z and E)-(1H-Benzimidazol-2-ylamino)methylidene]-1H-pyrrolo[3,2-b]pyridin-2one

EXAMPLE 212

3-((Z and E)-{[6-(4-Morpholinyl)-3-pyridinyl]amino}methylidene)-1,3-dihydro-2H-pyrrolo[3,2-b]pyridin-2-one. Accurate mass M+H=324.1449 (mmu error 1.0)

Pharmaceutical Formulation and Doses

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, optic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to about 100 mg/kg of body weight per day, and particularly about 1 to 10 mg/kg of body weight per day. Oral dosage units will generally be administered in the range of from 1 to about 250 mg and more preferably from about 25 to about 250 mg. The daily dosage for a 70 kg mammal will generally be in the range of about 70 mg to 7 grams of a compound of formula I or II.

The dosage to be administered is based on the usual conditions such as the physical condition of the patient, age, body weight, past medical history, route of administrations, severity of the conditions and the like. Oral administration is generally preferred for administration to a human. In some cases, a relatively lower dose is sufficient and, in some cases, a relatively higher dose or increased number of doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. The compounds of the invention can be prepared in a range of concentrations for topical use of about 0.5 to about 5 mg/ml of suitable solvent. A preferred volume for application to the scalp is about 2 ml, resulting in an effective dosage delivered to the patient of about 1 to about 10 mg.

For treatment of chemotherapy-induced alopecia, administration 1 to 2 times prior to chemotherapy administration is preferred, with additional applications administered as needed. A similar regimen can be pursued for treatment of alopecia induced by radiation therapy. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for Example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing about 0.01 to about 99.5%, more particularly, about 0.5 to about 90% of a compound of the formula (II) in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for Example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of a compound of the invention and a suitable powder base such as lactose or starch.

The preferred pharmaceutical compositions are those in a form suitable for oral administration, such as tablets and liquids and the like and topical formulations.

Biological Data

The compounds of the present invention have valuable pharmacologic properties. Different compounds from this class are particularly effective at inhibiting the VEGF-R2 receptor kinase enzyme at concentrations which range from 0.0001 to 1 $\mu$M and additionally show selectivity relative to other kinases. Substrate phosphorylation assays were carried out as follows:

VEGFR-2

The peptide substrate used in the VEGFR-2 assay was biotin-aminohexyl-EEEEYFELVAKKKK-NH$_2$. The kinase domain of the enzyme was purified to homogeneity from a baculovirus expression system. The enzyme was preactivated on ice for 15 min in the presence of 100 $\mu$M ATP and 20 mM MgCl$_2$, and stored at –80° C. until needed for assay. The activated enzyme was diluted to 0.4 nM into a 60 $\mu$l reaction containing 100 mM HEPES, pH 7.5, 5 $\mu$M ATP, 10 mM MgCl$_2$, 5 $\mu$M peptide, 0.1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by the addition of EDTA to 60 mM in 210 $\mu$l. The quenched samples (190 $\mu$l) were transferred to a neutravidin-coated plate (Pierce) and incubated at room temperature for 40 min to allow biotinylated peptide to bind to the neutravidin. The unbound components of the reaction were removed by washing with a plate washer, then 200 $\mu$l HRP-PY20 anti-phosphotyrosine antibody conjugate was added to each well. After incubation for 40 min, the plate was washed to remove any unbound anitbody. A HRP substrate, K-blue (Neogen) was added and the reaction was quenched with Red Stop (Neogen) after 20 min. The absorbance of the wells was read at A$_{650}$ in a plate reader. IC$_{50}$ values were obtained by fitting raw data to A$_{650}$=V$_{MAX}$*(1–[I]/IC$_{50}$+[I])))+b, where b is background.

CDK1 and CDK2

Cyclin dependent protein kinase assays utilized the peptides Biotin-aminohexyl-MKAKKTPKKAKK and Biotin-aminohexyl-ARRPMSPKKKA-NH$_2$ as phosphoryl group acceptors. CDK1 and CDK2 were both expressed utilizing a baculovirus expression system and were partially purified to comprise 20–80% of total protein, with no detectable competing reactions present. Typically, assays were performed by incubating either enzyme (0.2–10 nM), with and without inhibitor, one of the two peptide substrates (1–10 nM), [$\gamma$-$^{32}$P]ATP (1–20 nM), and 10–20 mM Mg$^{2+}$ for periods of time generally within the range 10–120 min. Reactions were terminated with 0.2–2 volumes of either 20% acetic acid or 50–100 mM EDTA buffered to pH 7 (substrate consumption <20%). The buffer employed in enzyme assays was either 30 mM HEPES 7.4 containing 0.15 M NaCl and 5% DMSO, the buffer 50 mM MOPS 7.0 containing 0.15 M NaCl and 5% DMSO, or the buffer 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=V$_{max}$*(1–([I]/(K+[I])))+nsb, or pIC50s were determined by a fit to the equation CPM=nsb+(V$_{max}$–nsb)/(1+(x/10$^x$–pIC50)), where nsb are the background counts.

Tie-2

The peptide substrate used in the Tie-2 assay was biotin-aminohexyl-LEAREYRWLGGKKKamide. The kinase domain of the enzyme was purified to homogeneity from a baculovirus expression system. The enzyme was diluted to 10 nM into a 60 $\mu$l reaction containing 100 mM HEPES, pH 7.5, 500 $\mu$M ATP, 10 mM MgCl$_2$, 2 $\mu$M peptide, 1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by stopped by 80 $\mu$l of 0.15 M EDTA. The quenched samples (125 $\mu$l) were transferred to a Neutravidin plates #15128 and incubated at room temperature for 30–60 minutes, allowing the biotinylated peptide to bind to the neutravidin on the plates. The neutravidin plates were then washed with water for 5 times. Europium conjugated anti-phosphotyrosine antibody, (EG & G Wallac, #CR04-100) (1 mg/ml) was diluted 1:10,000 in 1% BSA-0.05% Tween 20-TBS, and 150 $\mu$l of the diluted antibody was added to each well of the neutravidin plate, so the phosphorylated peptide was bound with the Europium labelled antibody. After another 30–60 min incubation at room temperature, the plates were washed again with water for 5 times. 150 ul of Enhancemant solution was then added to each well, dissociating Eu$^{3+}$ rom solid phase bound antibodies to form a homogeneous and highly fluorescent Eu-(2-NTA)$_3$(TOPO)$_{2-3}$ micellar chelate solution. The plates were incubated for 10 minutes at room temperature to allow the above process, and fluorescent signal for each well was determined in a Wallac 1420 Victor Multilabel Counter with "Europium" protocol.

The kinase activity of all wells was calculated as %S, the percentage of the fluorescent counts vs. positive controls after substraction of negative controls, as in eq. 1.

$$\% S = 100 * \frac{Counts_{sample} - Counts_{negative}}{Counts_{positive} - Counts_{negative}} \quad (1)$$

Plots of compound concentration versus %S were constructed. IC50s (K, expressed in units of molarity), the compound concentration at which the enzyme activity was inhibited by 50%, were determined from nonlinear least squares fits of the data to the simple competitive binding model of eq. 2.

$$\%S = \%S_{max} * (1 - (X/(K+X))) + Y2 \quad (2)$$

Where %S is the experimentally observed count rate at sample compound concentration X, $\%S_{max}$ is the best fit value for the maximum amplitude of the concentration-response curve, $Y_2$ is the count rate observed at infinitely high inhibitor concentration.

c-Fms c-fms protein kinase assays utilized the peptide substrate, biotin-EAIYMPFAKKK-NH$_2$, as the phosphoryl group acceptor. The c-fms intracellular domain was expressed from a baculovirus expression system, as an amino-terminal GST fusion protein, and purified to homogeneity using Glutathione agarose from Sigma Chemical Co. Maximum activation of the enzyme was achieved by preactivation at room temperature for 120 min in the presence of 100 $\mu$M ATP and 15 mM MgCl$_2$. This enzyme stock was diluted to 150 nM prior to using in the assay. Typically assays were performed in white, opaque, 96-well plates in a 45 ul assay volume including 15 ul 6% DMSO, with or without compounds, 15 ul of the preactivated, diluted enzyme, and 15 ul of a substrate mixture. Reactions contained 50 mM HEPES, pH 7.5, 1.7 $\mu$M ATP, 15 mM MgCl$_2$, 3 $\mu$M peptide, 2.5 mM DTT, 50 mM NaCl and 0.15 uCi/assay [$^{32}$P]ATP. The controls were reactions in the presence (negative controls) or absence (positive controls) of 50 mM EDTA. Reactions were allowed to proceed for 90 min at room temperature. The reaction products were quantified using Scintillation Proximity technolgy. The reactions were quenched by the addition of 200 ul of a solution containing 0.3 mg streptavidin SPA beads from Amersham, 50 mM EDTA, 0.1% TX-100, 50 uM ATP, in PBS, pH7.2 (phosphate buffered solution). Plates were sealed and counted in a Packard Topcount scintillation counter. IC50 values were obtained by fitting raw data to the equation y-Vmax*(1-(x/(k+x))).

The results shown in Table 7 summarise representative data: Table 7 illustrates the inhibitory activity of compounds of the present invention against several different kinases (VEGFR2, CDK2, Tie-2, and c-fms).

TABLE 7

Kinase inhibition data of representative compounds

| Compound | VEGFR2 | CDK2 | Tie-2 | c-fms |
|---|---|---|---|---|
| Example 24 | +++ | ++ | + | + |
| Example 29 | +++ | + | + | + |
| Example 30 | +++ | +++ | + | + |

TABLE 7-continued

Kinase inhibition data of representative compounds

| Compound | VEGFR2 | CDK2 | Tie-2 | c-fms |
|---|---|---|---|---|
| Example 32 | +++ | ++ | + | + |
| Example 48 | ++++ | +++ | + | + |
| Example 55 | ++++ | +++ | + | + |
| Example 58 | +++ | +++ | + | |
| Example 63 | ++++ | | + | |
| Example 66 | ++++ | | + | |
| Example 71 | +++ | | + | |
| Example 72 | ++++ | | + | |

Key (IC$_{50}$, nM)
1–10: ++++
11–50: +++
51–100: ++
>100: +

VEGF-R2 receptor kinase mediates intracellular signal transduction produced by extracellular receptor binding of Vascular Endothelial Growth Factor (VEGF) in the endothelial cells involved in angiogenesis. An inhibitor of VEGF-R2 receptor kinase can therefore block mitogenesis in endothelial cells, and will show selectivity (greater inhibition) compared to effects of other growth factors. An assay to measure this effect involves measurement of the inhibition of bromo-deoxy uridine (BrdU) incorporation (evidence of DNA synthesis) in human umbilical vein endothelial cells (HUVECs). Selectivity is demonstrated by comparison to the inhibition of BrdU incorporation prompted by basic Fibroblast Growth Factor (bFGF). These assays are described below.

HUVEC BrdU incorporation

Materials

HUVEC cells and EGM (Endothelial cell growth medium) were purchased from Clonetics (San Diego, Calif.). VEGF and bFGF were purchased from Genzyme. M199 medium (Gibco BRL) with BSA (Sigma) was used for cell culture in Type I collagen coated plates (Becton Dickinson). The degree of BrdU incorporation was measured using a commercial colorimetric ELISA assay from Boehringer Mannheim.

Method

HUVECs were plated at a density of 2500 cells per well in M199 medium containing 5% FBS (Hyclone) in a Type-I Collagen coated plate. The plate was incubated at 37° C. overnight. The medium was removed by aspiration, and test compounds were added to each well in a volume of 0.1 ml per well in serum-free M199 medium. Compound concentrations ranged from 0.15 nM to 3.0 micromolar. The plate was incubated for 30 min at 37° C. Another 0.1 ml of serum-free M199 medium containing BSA and VEGF (or bFGF) was added to give a final concentration of 0.1% BSA and 20 ng/ml VEGF (0.3 ng/ml bFGF). The plate was incubated at 37° C. for 72 hrs. BrdU was added to each well after the first 48 hrs to give a concentration of 10 micomolar. The calorimetric ELISA assay was performed according to manufacturer's instructions, with detection by absorbance reading at 450 nm. Results were plotted as concentration of test compound vs. absorbance to give an IC$_{50}$ value for inhibition of BrdU incorporation.

Values of IC$_{50}$ inhibition for VEGF and bFGF by representative compounds are given in Table 8.

TABLE 8

Inhibition of BrdU incorporation in HUVEC cells

| Compound | VEGF stimulation | BFGF Stimulation |
| --- | --- | --- |
| Example 24 | ++++ | + |
| Example 29 | ++++ | + |
| Example 30 | ++++ | ++ |
| Example 32 | ++++ | ++ |
| Example 48 | ++++ | +++ |
| Example 55 | ++ | + |
| Example 58 | ++++ | ++ |
| Example 63 | ++++ | +++ |
| Example 66 | +++ | + |
| Example 71 | ++++ | ++++ |
| Example 72 | ++++ | ++++ |

Key (IC$_{50}$, μM)
0.01–0.5: ++++
0.6–1.0: +++
1.1–5.0: ++
>5.0: +

UTILITY OF INVENTION

Inhibitors of VEGF-R2 kinase have utility as agents in the treatment of a wide variety of disorders which have a proliferative component dependent upon angiogenesis. These include, for example, cancers, arthritis, diabetic retinopathy, macular degeneration, and psoriasis.

The tumour inhibitory activity of the compounds of the present invention can be demonstrated in vivo, using Swiss Nu/Nu female mice in which mouse or human tumor cell lines have been implanted subcutaneously. Typical tumor types are the murine Lewis lung tumor and the human HT-29 colon carcinoma. In this assay, the compounds induce a marked reduction in the average tumour volume compared to vehicle treated controls.

The present invention demonstrates methodologies by which the process of angiogenesis induced by abnormal release of Vascular Endothelial Growth Factor (VEGF) may be inhibited by treatment with inhibitors of VEGF-R2 receptor tyrosine kinase. Proliferative disorders and other disorders involving abnormal angiogenesis can therefore be treated.

When the compounds of the present invention are used in conjunction with chemotherapeutic agents or radiation therapy for cancer treatment, they provide a secondary means of suppressing tumor growth either when administered simultaneously with chemotherapeutic agents, or in an alternating regimen to suppress tumor growth between chemotherapeutic or radiation treatments.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

The application of which this description and claim(s) forms part may be used as a basis for priority in respect of any subsequent application. The claims of such subsequent application may be directed to any feature or combination of features described herein. They may take the form of product, formulation, process or use claims and may include, by way of example and without limitation, one or more of the following claim(s).

What is claimed is:

1. A compound of the formula (I):

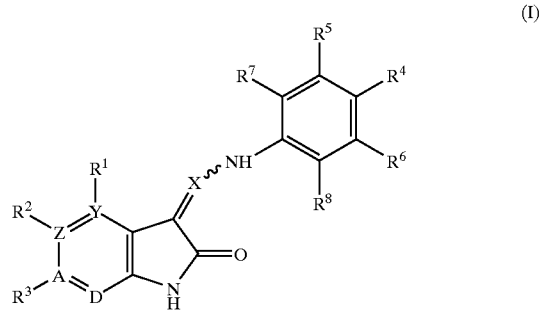

wherein
Y, Z, A, and D are carbon;
X is N;
R$^1$ is selected from the group consisting of: hydrogen, C$_{1-12}$ aliphatic, thiol, hydroxy, hydroxy-C$_{1-12}$ aliphatic, Aryl, Aryl-C$_{1-12}$ aliphatic, R$^9$-Aryl-C$_{1-12}$ aliphatic, Cyc, Cyc-C$_{1-6}$ aliphatic, Het, Het-C1-2aliphatic, C$_{1-12}$alkoxy, Aryloxy, amino, C$_{1-12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, fluoro, bromo, iodo, cyano, sulfonamide, or nitro, where R$^9$, Aryl, Cyc and Het are as defined below;
R$^2$ is selected from the group consisting of: hydrogen, C$_{1-12}$ aliphatic, N-hydroxyimino-C$_{1-12}$ aliphatic, C$_{1-12}$ alkoxy, hydroxy-C$_{1-12}$ aliphatic, C$_{1-12}$ alkoxycarbonyl, carboxyl C$_{1-12}$ aliphatic, Aryl, R$^9$-Aryl-oxycarbonyl, R$^9$-oxycarbonyl-Aryl, Het, aminocarbonyl, C$_{1-12}$ aliphatic-aminocarbonyl, Aryl-C$_{1-12}$ aliphatic-aminocarbonyl, R$^9$-Aryl-C$_{1-12}$ aliphatic-aminocarbonyl, Het-C$_{1-12}$ aliphatic-aminocarbonyl, hydroxy-C$_{1-12}$ aliphatic-aminocarbonyl, C$_{1-12}$-alkoxy-C$_{1-12}$ aliphatic-aminocarbonyl, C$_{1-12}$ alkoxy-C$_{1-12}$ aliphatic-amino, di-C$_{1-12}$ aliphatic amino, di-C$_{1-12}$ aliphatic aminocarbonyl, di-C$_{1-12}$ aliphatic aminosulfonyl, hydroxy, C$_{1-12}$ aliphatic-sulfonyl, aminosulfonyl, and C$_{1-12}$ aliphatic-aminosulfonyl, where R$^9$, Aryl and Het are as defined below, where R$^2$ is not 3,6-dihydro-6-methyl-2-oxo-2H-1,3,4-thiadiazin-5-yl;
R$^1$ and R$^2$ are optionally joined to form a fused ring selected from the group as defined for Het below, and said fused ring is optionally substituted by a substituent selected from the group consisting of: C$_{1-12}$ aliphatic, halogen, nitro, cyano, C$_{1-12}$ alkoxy, amino, hydroxyl, (R$^{10}$, R$^{11}$)-amino, and oxo;
R$^3$ is selected from the group consisting of: hydrogen, C$_{1-12}$ aliphatic, hydroxy, hydroxy C$_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, or Het-oxy, where Aryl and Het are as defined below;

$R^2$ and $R^3$ are optionally joined to form a fused ring selected from the group as defined for Het below, and said fused ring is optionally substituted by $C_{1-6}$ aliphatic or $C_{1-6}$ aliphatic-carbonyl; with the proviso that $R^1$, $R^2$, and $R^3$ cannot simultaneously be hydrogen;

$R^4$, $R^5$ and $R^6$ may be the same or different and are independently selected from the group consisting of: hydrogen, $C_{1-12}$ aliphatic, thiol, $C_{1-6}$aliphatic-thio, di(trifluoromethyl)hydroxymethyl, carboxamide, mono-$C_{1-2}$aliphatic aminocarbonyl, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, ($R^{10}$, $R^{11}$)-amino-$C_{1-12}$ aliphatic aminocarbonyl, ($R^{10}$,$R^{11}$)-amino-$C_{1-12}$ aliphatic alkoxycarbonyl, ($R^{10}$,$R^{11}$)-amino-$C_{1-12}$ aliphatic aminocarbonylamino, ($R^{10}$, $R^{11}$)-amino-$C_{1-6}$ aliphatic alkoxycarbonylamino, ($R^{10}$, $R^{11}$)-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{1-6}$ alkoxycarbonyl, $C_{1-6}$ aliphatic carbonylamino, ($C_{1-6}$ aliphatic carbonyl)($C_{1-6}$ aliphatic)amino, ($R^{10}$,$R^{11}$)-amino-$C_{1-6}$ aliphatic carbonylamino, [($R^{10}$,$R^{11}$)-amino-$C_{1-6}$ aliphatic carbonyl][$C_{1-6}$ aliphatic]amino, ($R^{10}$,$R^{11}$)-amino-$C_{1-6}$ aliphatic sulfonylamino, [($R^{10}$, $R^{11}$)-amino-$C_{1-6}$ aliphaticsulfonyl][$C_{1-6}$ aliphatic] amino, halogen, cyano, diethoxyphosphorylmethyl, trifluromethyl, and trifluoromethoxy, where $R^9$, $R^{10}$, $R^{11}$, Aryl, Cyc and Het are as defined below;

$R^7$ and $R^8$ may be the same or different and are independently selected from the group consisting of: hydrogen, halogen, $C_{1-2}$ alkoxy, hydroxy, and $C_{1-3}$ aliphatic; with the proviso that $R^4$, $R^5$, $R^6$, $R^7$, and $R^8$ cannot simultaneously be hydrogen; wherein $R^7$ may additionally be optionally fused to $R^5$ so as to form a fused benzo ring from the $R^5$ to the $R^7$ positions;

$R^9$ is selected from the group consisting of: $C_{1-12}$ aliphatic, hydroxy, $C_{1-12}$ alkoxy and halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of: $C_{1-12}$ aliphatic, hydroxy, $C_{1-12}$ alkoxy, ($R^{10}$,$R^{11}$)-amino, ($R^{10}$,$R^{11}$)-amino-$C_{1-12}$ aliphatic, ($R^{10}$,$R^{11}$)-amino-$C_{1-12}$ aliphatic amino, oxo and dioxo; and the pharmaceutically acceptable salts or solvates thereof in either crystalline or amorphous form.

2. A compound as claimed in claim 1 in the form of a substantially pure E geometric isomer.

3. A compound as claimed in claim 1 in the form of a substantially pure Z geometric isomer.

4. A compound as claimed in claim 1 in the form of a mixture of E geometric isomer and Z geometric isomer in any proportions of said geometric isomers.

5. A compound as claimed in claim 1, wherein $R^1$ is hydrogen, fluoro, bromo, iodo, lower alkyl, cyano or nitro.

6. A compound as claimed in claim 1, wherein $R^2$ is hydrogen, lower alkyl, lower alkoxy, hydroxy lower alkyl, $C_{1-12}$ alkoxycarbonyl, Aryl, Het, aminocarbonyl, lower alkyl aminocarbonyl, halogen or hydroxy.

7. A compound as claimed in claim 1, wherein $R^1$ is joined with $R^2$ to form a fused ring structure selected from the group consisting of: thiazole, imidazole, triazole and pyridine.

8. A compound as claimed in claim 1, wherein $R^4$ is hydrogen, lower alkyl, hydroxy, hydroxy-lower alkyl, carboxamide, mono-lower alkyl aminocarbonyl, substituted Aryl-lower alkyl, Het, Het-lower alkyl, lower alkoxy, Aryloxy, Het-oxy, amino, mono- or di-lower alkyl-amino lower alkyl aminocarbonyl, mono- or di-lower alkyl-amino lower alkoxycarbonyl, mono- or di-lower alkyl-amino lower alkyl aminocarbonylamino, mono- or di-lower alkyl-amino lower alkoxycarbonylamino, lower alkyl carbonylamino, (lower alkyl carbonyl)(lower alkyl)amino, mono- or di-lower alkyl-amino lower alkyl carbonylamino, (mono- or di-lower alkyl-amino lower alkyl carbonyl)(lower alkyl) amino, mono- or di-lower alkyl-amino lower alkyl sulfonylamino, (mono- or di-lower alkyl-amino lower alkyl sulfonyl)(lower alkyl)amino, mono- or di-lower alkyl-amino lower alkyl sulfonyl, Het lower alkyl aminocarbonyl, Het lower alkyl aminocarbonylamino, Het lower alkoxycarbonylamino, Het lower alkyl carbonyl, Het lower alkoxycarbonyl, lower alkyl sulfonyl lower alkyl aminoalkyl, lower alkyl sulfonyl-lower alkyl-aminoalkyl-Het-, lower alkoxycarbonyl, halogen, cyano, diethoxyphosphorylmethyl, trifluromethyl or trifluoromethoxy.

9. A compound as claimed in claim 1, wherein $R^5$ is hydrogen, lower alkyl, hydroxy, hydroxy-lower alkyl, carboxamide, mono-lower alkyl aminocarbonyl, substituted Aryl-lower alkyl, Het, Het-lower alkyl, lower alkoxy, Aryloxy, Het-oxy, amino, mono- or di-lower alkyl-amino lower alkyl aminocarbonyl, mono- or di-lower alkyl-amino lower alkoxycarbonyl, mono- or di-lower alkyl-amino lower alkyl aminocarbonylamino, mono- or di-lower alkyl-amino lower alkoxycarbonylamino, lower alkyl carbonylamino, (lower alkyl carbonyl)(lower alkyl)amino, mono- or di-lower alkyl-amino lower alkyl carbonylamino, (mono- or di-lower alkyl-amino lower alkyl carbonyl)(lower alkyl) amino, mono- or di-lower alkyl-amino lower alkyl sulfonylamino, (mono- or di-lower alkyl-amino lower alkyl sulfonyl][lower alkyl)amino, mono- or di-lower alkyl-amino lower alkyl sulfonyl, Het lower alkyl aminocarbonyl, Het lower alkyl aminocarbonylamino, Het lower alkoxycarbonylamino, Het lower alkyl carbonyl, Het lower alkoxycarbonyl, lower alkyl sulfonyl lower alkyl aminoalkyl, lower alkyl sulfonyl-lower alkyl-aminoalkyl- Het-, lower alkoxycarbonyl, halogen, cyano, diethoxyphosphorylmethyl, trifluromethyl or trifluoromethoxy, onyl, Het lower alkyl aminocarbonyl, Het lower alkyl carbonyl, lower alkyl sulfonyl lower alkyl aminoalkyl, lower alkyl sulfonyl-lower alkyl-aminoalkyl-Het-, halogen, cyano and trifluromethyl. Most highly preferred are hydroxymethyl, hydroxyethyl, 4-pyridylmethyl, 4-morpholino, acetamido, N-methylacetamido, carboxamide, diethylaminoethylsulfonyl, 5-methyl-3-pyrazolon-1-yl and 3-ethyl-piperidine-2,6-dion-3-yl.

10. A compound as claimed in claim 1, wherein $R^6$ is hydrogen.

11. A compound as claimed in claim 1, wherein $R^7$ is hydrogen, halogen or methyl.

12. A compound as claimed in claim 1, wherein $R^8$ is hydrogen, halogen or methyl.

13. A compound as claimed in claim 1, in Z, E or Z and E form, selected from the group consisting of:

3,6-Dihydro[1,2,3]triazolo[4,5-e]indole-7,8-dione8-[N-(4-methoxyphenyl)hydrazone];

3,6-Dihydro[1,2,3]triazolo[4,5-e]indole-7,8-dione8-{N-[4-(1,3-oxazol-5-yl)phenyl]hydrazone};

3,6-Dihydro[1,2,3]triazolo[4,5-e]indole-7,8-dione8-[N-(4-methylphenyl)hydrazone];

3,6-Dihydro[1,2,3]triazolo[4,5-e]indole-7,8-dione8-(N-{4-[(E)-2-(2-pyridinyl)ethenyl]phenyl}hydrazone);

6H-[1,3]Thiazolo[5,4-e]indole-7,8-dione8-[N-(3-methoxyphenyl)hydrazone];

5-Hydroxy-4,6-dimethyl-1H-indole-2,3-dione3-[N-(4-methylphenyl)hydrazone];

3,6-Dihydro[1,2,3]triazolo[4,5-e]indole-7,8-dione8-{N-[4-(trifluoromethyl)phenyl]hydrazone};

6H-[1,3]Thiazolo[5,4-e]indole-7,8-dione8-[N-(3-fluorophenyl)hydrazone];

6H-[1,3]Thiazolo[5,4-e]indole-7,8-dione8-[N-(4-fluorophenyl)hydrazone]; or

6H-[1,3]Thiazolo[5,4-e]indole-7,8-dione8-[N-(4-bromophenyl)hydrazone];

and pharmaceutically active salts or solvates thereof.

14. A pharmaceutical composition comprising a compound as claimed in claim 1 and one or more pharmaceutically acceptable carriers, diluents or excipients.

15. A pharmaceutical composition comprising a compound as claimed in claim 13 and one or more pharmaceutically acceptable carriers, diluents or excipients.

16. A compound as claimed in claim 1, wherein $R^3$ is hydrogen or lower alkyl.

17. A method of treating a susceptible cancer by inhibition of angiogenesis in a mammal, comprising administering to said mammal a therapeutically effective amount of a compound as claimed in claim 1.

* * * * *